US008802927B2

(12) United States Patent
De Block et al.

(10) Patent No.: US 8,802,927 B2

(45) Date of Patent: Aug. 12, 2014

(54) STRESS RESISTANT PLANTS

(75) Inventors: Marc De Block, Merelbeke (BE); Michael Metzlaff, Tervuren (BE); Veronique Gossele, Ghent (BE)

(73) Assignee: Bayer CropScience N.V., Diegem (BE)

( * ) Notice: Subject to any disclaimer, the term of this patent is extended or adjusted under 35 U.S.C. 154(b) by 957 days.

(21) Appl. No.: 12/916,180

(22) Filed: Oct. 29, 2010

(65) Prior Publication Data

US 2011/0131672 A1 Jun. 2, 2011

Related U.S. Application Data

(62) Division of application No. 11/663,657, filed as application No. PCT/EP2005/010168 on Sep. 16, 2005, now Pat. No. 7,851,675.

(60) Provisional application No. 60/628,826, filed on Nov. 17, 2004.

(30) Foreign Application Priority Data

Sep. 24, 2004 (EP) .................................... 04077624

(51) Int. Cl.

*A01H 5/00* (2006.01)
*A01H 5/10* (2006.01)
*C12N 15/82* (2006.01)

(52) U.S. Cl.

USPC ........ 800/289; 800/288; 800/298; 435/320.1; 435/419

(58) Field of Classification Search

None

See application file for complete search history.

(56) References Cited

U.S. PATENT DOCUMENTS

| | | | | |
|---|---|---|---|---|
| 5,792,921 | A | 8/1998 | Londesborough et al. | |
| 7,977,049 | B2 * | 7/2011 | Sinclair et al. | 435/6.11 |
| 2005/0267023 | A1 | 12/2005 | Sinclair et al. | |

FOREIGN PATENT DOCUMENTS

| | | |
|---|---|---|
| JP | 2004-261136 | 9/2004 |
| WO | WO 89/03887 | 5/1989 |
| WO | WO 89/10396 | 11/1989 |
| WO | WO 92/13956 | 8/1992 |
| WO | WO 96/06932 | 3/1996 |
| WO | WO 97/13865 | 4/1997 |
| WO | WO 00/04173 | 1/2000 |
| WO | WO 2004/016726 | 2/2004 |
| WO | WO 2004/090140 | 10/2004 |

OTHER PUBLICATIONS

An, et al., "Conserved Expression of the Arabidopsis ACT1 and ACT3 Actin Subclass on Organ Primordia and Mature Pollen", The Plant Cell, vol. 8, pp. 15-30 (1996).

Anderson, et al., "Nicotinamide and PNC1 Govern Lifespan extension by Calorie Restriction in *Saccharomyces cerevisiae*", Nature, vol. 423, p. 181-185 (2003).

EMBL BT002920 *Arabidopsis thalian* clone RAFL14-96410 (R20098) unknown protein (At5g23220) mRNA, complete cds (2003).

EMBL AY093004 *Arabidopsis thaliana* unknown protein (At4g36940) mRNA, complete cds (2002).

EMBL AY114544 *Arabidopsis thaliana* unknown protein (At5g55810) mRNA, complete cds (2002).

EMBL BT010741 *Arabidopsis thaliana* At1g55090 gene, complete cds (2003).

De Block, et al., "A simple and robust in vitro assay to quantify the vigour of oilseed rape lines and hybrids", Plant Physiol. Biochem., vol. 40, pp. 845-852 (2002).

Gallo, et al., "Nicotinamide Clearance by Pnc1 Directly Regulates Sir2-Mediated Silencing and Longevity", Molecular and Cellular Biology, vol. 24, No. 3, pp. 1301-1312 (2004).

Harpster, et al., "Relative Stengths of the 35S Califlower Mosiac Virus, 1', 2', and nopaline synthase promoters in transformed tobacco sugarbeet and oilseed rape callus tissue", Mol. Gen. Genet., vol. 212, pp. 182-190 (1988).

Hudspeth, et al., "Structure and Expression of the Maize gene encoding the phosphoenolpyruvate carboxylase isozyme involved in $C_4$ photosynthesis", Plant Molecular Biology, vol. 12, pp. 579-589 (1989).

Hunt, et al., NAD—new roles in signalling and gene regulation in plants, New Phytologist, vol. 163, pp. 31-44 (2004).

Keil, et al., "Both Wound-inducible and tuber-specific expression are mediated by the promoter of a single member of the potato protinase II gene family,"The EMBO Journal, vol. 8, No. 5, pp. 1323-1330 (1989).

Keller, et al., "Glycine-rich cell wall proteins in bean: gene structure and association of the protein with the vascular system", The EMBO Journal, vol. 7, No. 12, p. 3625-3633, 1988.

Keller, et al., "Specific Expression of a Novel cell Wall hydroxyproline-rich glycoprotein gene in lateral root initiation", Genes & Development, vol. 3, p. 1639-1646 (1989).

Nakamura, et al., "Quantitation of intracellular NAD(P)H can monitor an imbalance of DNA single strand break repair in base excision repair deficient cells in real time", Nucleic Acids Research, vol. 31, No. 17, e104, 7 pages (2003).

Peleman, et al., "Structure and expression analyses of the S-adenosylmethionine synthetase gene family in *Arabidopsis thaliana*", Gene, vol. 84, p. 359-369 (1989).

Uchimiya, et al., "Transgenic rice plants conferring increased tolerance to rice blast and multiple environmental stresses", Molecular Breeding, vol. 9, p. 25-31 (2002).

(Continued)

*Primary Examiner* — Cynthia Collins

(74) *Attorney, Agent, or Firm* — Hunton & Williams LLP

(57) ABSTRACT

Stress tolerance in plants and plant cells is achieved by using nucleotide sequences encoding enzymes involved in the NAD salvage synthesis pathway and/or the NAD de novo synthesis pathway e.g. for overexpression in plants.

14 Claims, 11 Drawing Sheets

(56) References Cited

OTHER PUBLICATIONS

Uchimiya, et al., "Metabolic activation of NAD pathway down-regulated cell death leading to biotic and abiotic stress resistance", Poster Abstracts, Programmed Cell Death Development, p. 61, (2003).

Wagner, et al., "The Pyridine-Nucleotide Cycle in Tobacco: Enzyme Activities for the Recycling of NAD," Planta, vol. 167, pp. 226-232 (1986).

Wang, et al., "Plant responses to drought, salinity and extreme temperatures: towards genetic engineering for stress tolerance", Planta, vol. 218, pp. 1-14 (2003).

Yan et al., The NAD+ precursors, Nicotinic acid and Nicotinamide Upregulate glyceraldehyde-3-phosphate Dehydrogenase and Glucose-6-phosphate dehydrogenase mRNA in Jurkat Cells Biochem Biophys Res Commun., vol. 255, No. 1, pp. 133-136 (1999).

International Search Report for International Application No. PCT/EP2005/010168, mailed Apr. 5, 2006.

* cited by examiner

NaMN: nicotinic acid mononucleotide
NaAD: desamino-NAD+

*PNC1*: nicotinamidase
*NPT1*: nicotinate phosphoribosyl transferase
*NMA*: NAD+ pyrophosphorylase
*QNS1*: NAD+ synthetase

STRESS RESISTANT PLANTS

CROSS-REFERENCE TO RELATED APPLICATIONS

This application is a divisional application of U.S. application Ser. No. 11/663,657 filed on Mar. 23, 2007 now U.S. Pat. No. 7,851,675, which is the U.S. national stage application of International Application No. PCT/EP2005/010168, filed on Sep. 16, 2005, which claims the benefit of European Application No. EP04077624.7, filed on Sep. 24, 2004, and U.S. Provisional Application Ser. No. 60/628,826, filed on Nov. 17, 2004, the disclosures of each of which are herein incorporated by reference in their entireties.

Methods are provided for increasing the stress resistance in plants and plant cells whereby enzymes involved in the NAD salvage synthesis pathway and/or the NAD de novo synthesis pathway are expressed in plants.

BACKGROUND ART

Tolerance of plants to adverse growing conditions, including drought, high light intensities, high temperatures, nutrient limitations, saline growing conditions and the like, is a very desired property for crop plants, in view of the never-ending quest to ultimately increase the actual yield of these plants.

Various ways of achieving that goal of improving what is commonly known as the stress resistance or stress tolerance of plants have been described. Since different abiotic stress conditions frequently result in the generation of harmfull reactive oxygen species ("ROS") such as superoxides or hydrogen peroxides, initial attempts to improve stress resistance in plants focused on prevention of the generation of the ROS or the removal thereof. Examples of these approaches are overexpression of ROS scavenging enzymes such as catalases, peroxidases, superoxide dismutases etc. or even increasing the amount of ROS scavenging molecules such as ascorbic acid, glutathione etc. These approaches and other attempts to engineer stress tolerant plants are reviewed e.g. in Wang et al. 2003, Planta 218:1-14.

Stress tolerance in plant cells and plants can also be achieved by reducing the activity or the level of the endogenous poly-ADP-ribose polymerases (ParP) or poly(ADP-ribose) glycohydrolases (ParG) as described in WO00/04173 and PCT/EP2004/003995, respectively. It is thought that in this way, fatal NAD and ATP depletion in plant cells subject to stress conditions, resulting in traumatic cell death, can be avoided or sufficiently postponed for the stressed cells to survive and acclimate to the stress conditions.

Uchimiya et al. (2002) et al. describe the isolation of a rice gene denoted YK1, as well as use of a chimeric YK1 gene to increase the tolerance of transgenic rice plants harboring that gene to rice blast and several abiotic stresses such as NaCl, UV—C, submergence, and hydrogen peroxide. (Uchimiya et al., 2002, Molecular breeding 9: 25-31).

Uchimiya et al. further published a poster abstract describing that overexpression of a NAD dependent reductase gene (YK1) in rice cells also promoted the level of NAD(P)(H) through up-regulating NAD synthetase activities, and concluded that this modification in turn generated a pool of redox substances needed for ROS stress resistance (Uchimiya et al. 2003 Keystone symposium on Plant biology: Functions and control of cell death, Snowbird Utah Apr. 10-15, 2003).

NAD synthetase from yeast has been well characterized and is the last enzyme in both the NAD de novo synthesis pathway and the NAD salvage pathway (see FIG. 1). In the de novo pathway, quinolate is the precursor for NAD synthesis and is generated as a product of tryptophan degradation. In the salvage pathway, nicotinamide (which is a degradation product of NAD, generated through the action of various enzymes such as PARP, NAD-dependent deacetylases or other NAD glycohydrolases) is the precursor molecule. In a first step, nicotinamide is deamidated to nicotinic cid by a nicotinamidase. The nicotinic acid is transferred to 5-phosphoribosyl-1-pyrophosphate by the enzyme nicotinate phosphoribosyl transferase to yield nicotinic acid mononucleotide. This compound is shared between the de novo and the salvage pathway. Hence, further conversion of this compound by NAD+ pyrophosphorylase and NAD synthetase is achieved as in the de novo pathway.

In yeast, overexpression of PNC1 (encoding nicotinamidase) has been correlated with life span extension by calorie restriction and low-intensity stress (Anderson et al., 2003 Nature 423: p181-185; Gallo et al., 2004, Molecular and Cellular Biology 24: 1301-1312).

Little is known about the respective enzymes of the NAD biosynthesis pathways in plants. Hunt et al., 2004 describe the use of the available genomic information from *Arabidopsis* to identify the plant homologues of these enzymes (Hunt et al., 2004, New Phytologist 163(1): 31-44). The identified DNA sequences have the following Accession numbers: for nicotinamidase: At5g23220; At5g23230 and At3g16190; for nicotinate phosphoribosyltransferase: At4g36940, At2g23420, for nicotinic acid mononucleotide adenyltransferase: At5g55810 and for NAD synthetase: At1g55090 (all nucleotide sequences are incorporated herein by reference).

Alternative methods for increasing stress tolerance in plants are still required and the embodiments described hereinafter, including the claims, provide such methods and means.

SUMMARY OF THE INVENTION

In one embodiment of the invention, a method is provided for obtaining a plant with increased stress resistance comprising introducing a chimeric gene into a cells of a plant to obtain transgenic cells whereby the chimeric gene comprises the following operably linked DNA fragments:

i. A plant-expressible promoter;

ii. A DNA region coding for a plant-functional enzyme of the nicotinamide adenine dinucleotide salvage synthesis pathway selected from nicotinamidase, nicotinate phosphoribosyltransferase, nicotinic acid mononucleotide adenyl transferase or nicotinamide adenine dinucleotide synthetase;

iii. A 3' end region involved in transcription termination and polyadenylation, followed by regenerating the transgenic cells to obtain a population of transgenic plants; and selecting a plant from the population of transgenic plants which exhibits increased stress resistance or selecting a plant which exhibits a reduced level of reactive oxygen species or maintains a high level of NADH under stress conditions when compared to a similar non-transgenic plant. The DNA region may code for a protein comprising an amino acid sequence selected from the aminoacid sequence of SEQ ID No.:2, SEQ ID No.:4, SEQ ID No.:6; SEQ ID No.:8, SEQ ID No.:10, SEQ ID No.:12; SEQ ID No.:14; SEQ ID No.:16, SEQ ID No.:18, SEQ ID No.:20, SEQ ID No.: 22, SEQ ID No.:24 or a protein having about 60% sequence identity and having the enzymatic activity of nicotinamide adenine dinucleotide salvage synthesis pathway such as the nucleotide sequences of SEQ ID No.:1, SEQ ID No.:3, SEQ ID No.:5; SEQ ID No.:7, SEQ ID No.:9, SEQ ID No.:11; SEQ ID No.:13; SEQ ID No.:15, SEQ ID No.:17, SEQ ID No.:19, SEQ ID No.: 21 or SEQ ID No.:23.

In another embodiment, the invention relates to the chimeric genes as described herein, plant cells comprising these chimeric genes, and plants consisting essentially of plant cells comprising these chimeric genes, and seeds of such plants. These plants and plant cells may be characterized in that they have a lower level of reactive oxygen species under stress conditions than a similar plant not comprising such a chimeric gene.

In yet another embodiment, the invention relates to the use of the described chimeric genes to increase the stress resistance of a plant or to decrease the level of reactive oxygen species in a plant or a plant cell under stress conditions.

The invention further provides the use of a DNA sequence encoding a plant functional enzyme of the nicotinamide adenine dinucleotide salvage synthesis pathway selected from nicotinamidase, nicotinate phosphoribosyltransferase, nicotinic acid mononucleotide adenyl transferase or nicotinamide adenine dinucleotide synthetase, such as a DNA sequence encoding a protein comprising an amino acid sequence selected from the aminoacid sequence of SEQ ID No.:2, SEQ ID No.:4, SEQ ID No.:6; SEQ ID No.:8, SEQ ID No.:10, SEQ ID No.:12; SEQ ID No.:14; SEQ ID No.:16, SEQ ID No.:18, SEQ ID No.:20, SEQ ID No.: 22, SEQ ID No.:24 or a protein having about 60% sequence identity and having the enzymatic activity of nicotinamide adenine dinucleotide salvage synthesis pathway, including a DNA sequence comprising an nucleotide sequence selected from the nucleotide sequence of SEQ ID No.:1, SEQ ID No.:3, SEQ ID No.:5; SEQ ID No.:7, SEQ ID No.:9, SEQ ID No.:11; SEQ ID No.:13; SEQ ID No.:15, SEQ ID No.:17, SEQ ID No.:19, SEQ ID No.:21 or SEQ ID No.:23, to increase the stress resistance of a plant or to decrease the level of reactive oxygen species or maintain the level of NADH in a plant or a plant cell under stress conditions.

DETAILED DESCRIPTION

Figure 1:
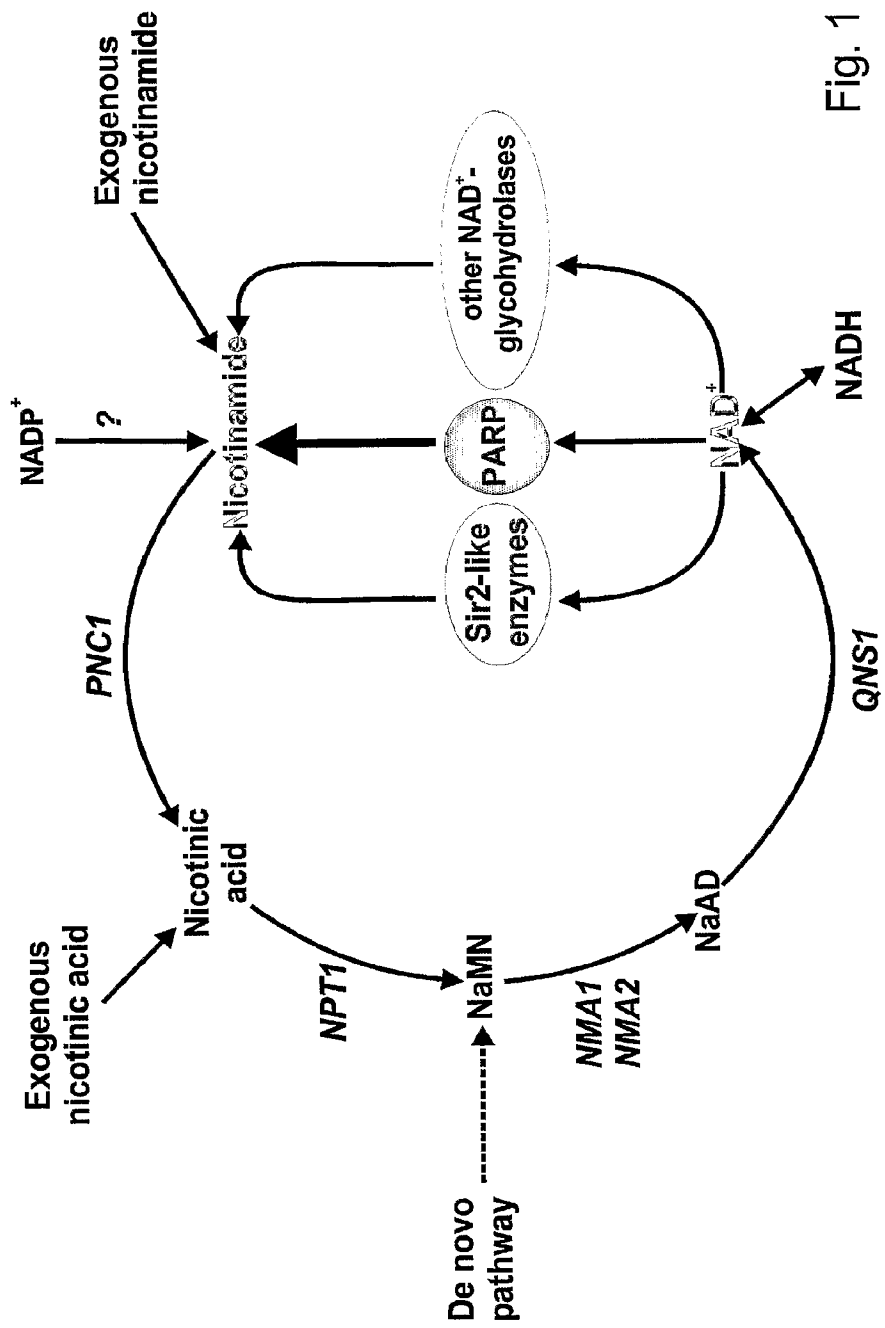
FIG. 1 is a schematic representation of the NAD salvage pathway and the de novo NAD synthesis pathway as known in baker's yeast (*Saccharomyces cerevisea*)

The current invention is based on the finding that DNA sequences encoding plant-functional enzymes from the NAD salvage pathway in yeasts could be used to obtain transgenic plants which were more resistant to stress, particularly abiotic stress, than plants not comprising these DNA sequences. The transgenic plants also exhibited a significantly reduced level of reactive oxygen species ("ROS") and maintained a high level of NADH, when put under stress conditions, compared to control plants Thus in one embodiment of the invention, a method is provided to obtain a plant with increased stress resistance, whereby the method comprises the steps of

- introducing a stress resistant chimeric gene as herein described into cells of a plant to obtain cells comprising the stress resistant chimeric gene;
- regenerating these cells comprising the stress resistant chimeric gene to obtain a population of plants comprising the stress resistant chimeric gene; and
- selecting a plant from the population of these plants which exhibits increased stress resistance and/or decreased ROS level under stress conditions and/or maintains a high level of NADH, when compared to a similar non-transgenic plant.

The stress resistant chimeric gene thereby comprises a plant-expressible promoter operably linked to a DNA region coding for a plant-functional enzyme of the nicotinamide adenine dinucleotide salvage synthesis pathway selected from nicotinamidase, nicotinate phosphoribosyltransferase, nicotinic acid mononucleotide adenyl transferase or nicotinamide adenine dinucleotide synthetase and a 3' end region involved in transcription termination and polyadenylation.

As used herein, "a plant-functional enzyme of the nicotinamide adenine dinucleotide salvage synthesis pathway" is an enzyme which when introduced into plants, linked to appropriate control elements such as plant expressible promoter and terminator region, can be transcribed and translated to yield a enzyme of the NAD salvage synthesis pathway functional in plant cells. Included are the enzymes (and encoding genes) from the NAD salvage synthesis, which are obtained from a plant source, but also the enzymes obtained from yeast (*Saccharomyces cereviseae*) or from other yeasts or fungi. It is thought that the latter proteins may be even more suitable for the methods according to the invention, since these are less likely to be subject to the enzymatic feedback regulation etc. to which similar plant-derived enzymes may be subject.

Enzymes involved in the NAD salvage synthesis pathway comprise the following

- Nicotinamidase (EC 3.5.1.19) catalyzing the hydrolysis of the amide group of nicotinamide, thereby releasing nicotinate and NH3. The enzyme is also known as nicotinamide deaminase, nicotinamide amidase, YNDase or nicotinamide amidohydrolase
- Nicotinate phosphoribosyltransferase (EC 2.4.2.11) also known as niacin ribonucleotidase, nicotinic acid mononucleotide glycohydrolase; nicotinic acid mononucleotide pyrophosphorylase; nicotinic acid phosphoribosyltransferase catalyzing the following reaction

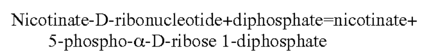

Nicotinate-D-ribonucleotide+diphosphate=nicotinate+ 5-phospho-α-D-ribose 1-diphosphate

- Nicotinate-nucleotide adenylyltransferase, (EC 2.7.7.18) also known as deamido-NAD+ pyrophosphorylase; nicotinate mononucleotide adenylyltransferase; deamindonicotinamide adenine dinucleotide pyrophsophorylase; NaMT-ATase; nicotinic acid mononucleotide adenylyltransferase catalyzing the following reaction

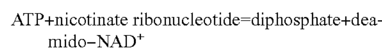

ATP+nicotinate ribonucleotide=diphosphate+deamido-$NAD^+$

NAD-synthase (EC 6.3.1.5) also known as NAD synthetase; $NAD^+$synthase; nicotinamide adenine dinucleotide synthetase; diphosphopyridine nucleotide synthetase, catalyzing the following reaction

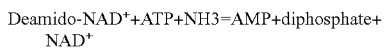

Deamido-$NAD^+$+ATP+NH3=AMP+diphosphate+$NAD^+$

In one embodiment of the invention, the coding regions encoding the different enzymes of the NAD salvage pathway comprise a nucleotide sequence encoding proteins with the amino acid sequences as set forth in SEQ ID Nos 2, 4, 6, 8 or 10, such as the nucleotide sequences of SEQ ID Nos 1, 3, 5, 7 or 9.

However, it will be clear that variants of these nucleotide sequences, including insertions, deletions and substitutions thereof may be also be used to the same effect. Equally, homologues to the mentioned nucleotide sequences from species different from *Saccharomyces cerevisea* can be used. These include but are not limited to nucleotide sequences from plants, and nucleotide sequences encoding proteins with the same amino acid sequences, as well as variants of such nucleotide sequences. Examples of the latter are nucleotide sequences encoding a protein with an amino acid sequence as set forth in SEQ ID Nos 12, 14, 16, 18, 20, 22 or 24 such as the nucleotide sequences of SEQ ID Nos 11, 13, 15, 17, 19, 21 or 23.

Variants of the described nucleotide sequence will have a sequence identity which is preferably at least about 80%, or 85 or 90% or 95% with identified nucleotide sequences encoding enzymes from the NAD salvage pathway, such as the ones identified in the sequence listing. Preferably, these variants will encode functional proteins with the same enzymatic activity as the enzymes from the NAD salvage pathway. For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above, can be conveniently performed using standard software program such as GAP which is part of the Wisconsin Package Version 10.1 (Genetics Computer Group, Madision, Wis., USA) using the default scoring matrix with a gap creation penalty of 50 and a gap extension penalty of 3.

Nucleotide sequences homologous to the nucleotide sequences encoding an enzyme from the NAD salvage pathway in yeast, or encoding a homologous enzyme from an organism different than yeast may be identified by in silico analysis of genomic data, as described by Hunt et al. (vide supra).

Homologous nucleotide sequence may also be identified and isolated by hybridization under stringent conditions using as probes identified nucleotide sequences encoding enzymes from the NAD salvage pathway, such as the ones identified in the sequence listing.

"Stringent hybridization conditions" as used herein means that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared carrier DNA such as salmon sperm DNA, followed by washing the hybridization support in 0.1×SSC at approximately 65° C., preferably twice for about 10 minutes. Other hybridization and wash conditions are well known and are exemplified in Sambrook et al, Molecular Cloning: A Laboratory Manual, Second Edition, Cold Spring Harbor, N.Y. (1989), particularly chapter 11.

Such variant sequences may also be obtained by DNA amplification using oligonucleotides specific for genes encoding enzymes from the NAD salvage pathway as primers, such as but not limited to oligonucleotides comprising about 20 to about 50 consecutive nucleotides selected from the nucleotide sequences of SEQ ID Nos 1, 3, 5, 7, 9, 11, 13, 15, 17, 19, 21, 23 or their complement.

The methods of the invention can be used to obtain plants tolerant to different kinds of stress-inducing conditions, particularly abiotic stress conditions including submergence, high light conditions, high UV radiation levels, increased hydrogen peroxide levels, drought conditions, high or low temperatures, increased salinity conditions. The methods of the invention can also be used to reduce the level of ROS in the cells of plants growing under adverse conditions, particularly abiotic stress conditions including submergence, high light conditions, high UV radiation levels, increased hydrogen peroxide levels, drought conditions, high or low temperatures, increased salinity conditions etc. The level of ROS or the level of NADH can be determined using the methods known in the art, including those described in Example 3.

Using the methods described herein, plants may be obtained wherein the level of ROS is equal to or lower than in control plants under non-stressed conditions, such as but not limited to low light. In these plants, under non-stressed conditions, the level of ROS may range from 50% to 100% of the level of control plants under low light conditions, more particularly from about 60% to about 85%. The level of the ROS in these plants under stress conditions is about 50% to 80% of the level of ROS in control plants under stress conditions, corresponding to about 60 to 80% of the level of ROS in control plants under non-stressed conditions. Similarly, the NADH level in these plants is equal to or higher than in control plants under non-stressed conditions, such as but not limited to low light. In these plants, under non-stressed conditions, the level of NADH may range from 100% to 160% of the level of NADH in control plants under low light conditions, more particularly from about 120% to about 140%. The level of NADH in these plants under stress conditions is about 200 to 300% of the level of NADH in control plants under stress conditions, corresponding to about 100 to 160% of the level of ROS in control plants under non-stressed conditions.

Methods to obtain transgenic plants are not deemed critical for the current invention and any transformation method and regeneration suitable for a particular plant species can be used. Such methods are well known in the art and include *Agrobacterium*-mediated transformation, particle gun delivery, microinjection, electroporation of intact cells, polyethyleneglycol-mediated protoplast transformation, electroporation of protoplasts, liposome-mediated transformation, silicon-whiskers mediated transformation etc. The transformed cells obtained in this way may then be regenerated into mature fertile plants.

The obtained transformed plant can be used in a conventional breeding scheme to produce more transformed plants with the same characteristics or to introduce the chimeric gene according to the invention in other varieties of the same or related plant species, or in hybrid plants. Seeds obtained from the transformed plants contain the chimeric genes of the invention as a stable genomic insert and are also encompassed by the invention.

It will be clear that the different stress resistant chimeric genes described herein, with DNA regions encoding different enzymes from the NAD salvage pathway can be combined within one plant cell or plant, to further enhance the stress tolerance of the plants comprising the chimeric genes. Thus, in one embodiment of the invention, plant cells and plants are provided which comprise at least two stress resistant chimeric genes each comprising a different coding region.

The transgenic plant cells and plant lines according to the invention may further comprise chimeric genes which will reduce the expression of endogenous PARP and/or PARG genes as described in WO 00/04173 and PCT/EP2004/003995. These further chimeric genes may be introduced e.g. by crossing the transgenic plant lines of the current invention with transgenic plants containing PARP and/or PARG gene expression reducing chimeric genes. Transgenic plant cells or plant lines may also be obtained by introducing or transforming the chimeric genes of the invention into transgenic plant cells comprising the PARP or PARG gene expression reducing chimeric genes or vice versa.

For the purpose of the invention, the promoter is a plant-expressible promoter. As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Harpster et al., 1988 *Mol. Gen. Genet.* 212, 182-190), the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al., 1996, *The Plant Cell* 8, 15-30), stem-specific promoters (Keller et al., 1988, *EMBO J.* 7, 3625-3633), leaf specific promoters (Hudspeth et al., 1989, *Plant Mol Biol* 12, 579-589), mesophyl-specific promoters (such as the light-inducible Rubisco promoters), root-specific promoters (Keller et al., 1989, *Genes Devel.* 3, 1639-1646), tuber-specific promoters (Keil et al., 1989, *EMBO J.* 8, 1323-1330), vascular tissue specific promoters (Peleman et al., 1989, *Gene* 84, 359-369), stamen-selective promoters (WO 89/10396, WO 92/13956), dehiscence zone specific promoters (WO 97/13865) and the like.

The chimeric genes of the inventions may also be equipped with a nuclear localization signal ("NLS") functional in plants, operably linked to the DNA region encoding an enzyme of the NAD salvage pathway such as the SV40 NLS.

Having read this document, a person skilled in the art will immediately realize that similar effects with regard to increased stress resistance can be obtained whenever natural variants of plants are obtained wherein the endogenous genes coding for NAD salvage pathway enzymes are more active or expressed at a higher level. Such variant plants can be obtained by subjecting a population of plants to mutagenesis, such as, but not limited to EMS mutagenesis, followed by a screening for an increased activity of any one of the NAD salvage pathway enzymes, or a combination thereof.

It will also be immediately clear that a population of different varieties or cultivars can be screened for increased tolerance to the above mentioned stress conditions in general or particular selected abiotic stresses, followed by a correlation of the increased tolerance to stress conditions with the presence of a particular allele of any of the endogenous genes encoding an enzyme of the NAD salvage pathway enzyme. Such alleles can than be introduced into a plant of interest by crossing, if the species are sexually compatible, or they may be identified using conventional techniques as described herein (including hybridization or PCR amplification) and introduced using recombinant DNA technology. Introduction of particularly desired alleles using breeding techniques may be followed using molecular markers specific for the alleles of interest.

The methods and means described herein are believed to be suitable for all plant cells and plants, both dicotyledonous and monocotyledonous plant cells and plants including but not limited to cotton, *Brassica* vegetables, oilseed rape, wheat, corn or maize, barley, sunflowers, rice, oats, sugarcane, soybean, vegetables (including chicory, lettuce, tomato), tobacco, potato, sugarbeet, papaya, pineapple, mango, *Arabidopsis thaliana*, but also plants used in horticulture, floriculture or forestry.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined, may comprise additional DNA regions etc.

The following non-limiting Examples describe the construction of chimeric genes to increase stress resistance in plant cells and plants and the use of such genes.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Throughout the description and Examples, reference is made to the following sequences:

SEQ ID No. 1: nucleotide sequence of the nicotinamidase from *Saccharomyces cereviseae* (PNC1).

SEQ ID No. 2:. amino acid sequence of the nicotinamidase from *Saccharomyces cereviseae* (PNC1).

SEQ ID No. 3:. nucleotide sequence of the nicotinate phosphoribosyltransferase from *Saccharomyces cereviseae* (NPT1) (complement)

SEQ ID No. 4:. amino acid sequence of the nicotinate phosphoribosyltransferase from *Saccharomyces cereviseae* (NPT1)

SEQ ID No. 5: nucleotide sequence of the nicotinic acid mononucleotide adenyl transferase 1 (NMA1) from *Saccharomyces cereviseae.*

SEQ ID No. 6: amino acid sequence of the nicotinic acid mononucleotide adenyl transferase 1 (NMA1) from *Saccharomyces cereviseae*

SEQ ID No. 7: nucleotide sequence of the nicotinic acid mononucleotide adenyl transferase 2 (NMA2) from *Saccharomyces cereviseae.*

SEQ ID No. 8: amino acid sequence of the nicotinic acid mononucleotide adenyl transferase 2 (NMA2) from *Saccharomyces cereviseae.*

SEQ ID No. 9: nucleotide sequence of the NAD synthetase (QNS1) from *Saccharomyces cereviseae.*

SEQ ID No. 10: amino acid sequence of the NAD synthetase (QNS1) from *Saccharomyces cereviseae.*

SEQ ID No. 11:. nucleotide sequence of the nicotinamidase from *Arabidopsis thaliana* (isoform 1).

SEQ ID No. 12:. Amino acid sequence of the nicotinamidase from *Arabidopsis thaliana* (isoform 1).

SEQ ID No. 13:. nucleotide sequence of the nicotinamidase from *Arabidopsis thaliana* (isoform 2)

SEQ ID No. 14: Amino acid sequence of the nicotinamidase from *Arabidopsis thaliana* (isoform 2).

SEQ ID No. 15:. nucleotide sequence of the nicotinamidase from *Arabidopsis thaliana* (isoform 3)

SEQ ID No. 16: Amino acid sequence of the nicotinamidase from *Arabidopsis thaliana* (isoform 3).

SEQ ID No. 17: nucleotide sequence of the nicotinate phosphoribosyltransferase from *Arabidopsis thaliana* (isoform 1).

SEQ ID No. 18: amino acid sequence of the nicotinate phosphoribosyltransferase from *Arabidopsis thaliana* (isoform 1).

SEQ ID No. 19: nucleotide sequence of the nicotinate phosphoribosyltransferase from *Arabidopsis thaliana* (isoform 2).

SEQ ID No. 20: amino acid sequence of the nicotinate phosphoribosyltransferase from *Arabidopsis thaliana* (isoform 2).

SEQ ID No. 21: nucleotide sequence of the nicotinic acid mononucleotide adenyl transferase from *Arabidopsis thaliana.*

SEQ ID No. 22: amino acid sequence of the nicotinic acid mononucleotide adenyl transferase from *Arabidopsis thaliana.*

SEQ ID No. 23: nucleotide sequence of the NAD synthetase from *Arabidopsis thaliana.*

SEQ ID No. 24: amino acid sequence of the NAD synthetase from *Arabidopsis thaliana.*

SEQ ID No. 25: nucleotide sequence of T-DNA vector pTVE 467

SEQ ID No. 26: nucleotide sequence of T-DNA vector pTVE 468

SEQ ID No. 27: nucleotide sequence of T-DNA vector pTVE 469

SEQ ID No. 28: nucleotide sequence of T-DNA vector pTVE 470

SEQ ID No. 29: nucleotide sequence of T-DNA vector pTVE 496

SEQ ID No. 30: nucleotide sequence of T-DNA vector pTVE 497

SEQ ID No. 31: nucleotide sequence of T-DNA vector pTVE 500

SEQ ID No. 32: nucleotide sequence of T-DNA vector pTVE 501

SEQ ID No. 33: nucleotide sequence of T-DNA vector pTVE 502

SEQ ID No. 34: nucleotide sequence of T-DNA vector pTVE 503

EXAMPLES

Example 1

Assembly of Stress Resistant Chimeric Genes and Introduction into Plants pTVE467

To increase the stress resistance in plants, a chimeric gene was constructed using conventional techniques comprising the following DNA fragments in order:

- A promoter region from Cauliflower Mosaic Virus (CaMV 35S);
- A DNA fragment of about 60 bp corresponding to the untranslated leader Cab22L;
- A DNA fragment encoding nicotinamidase from *Saccharomyces cereviseae* (SEQ ID NO 1);
- A fragment of the 3' untranslated end from the 35 S transcript of CaMV (3' 35S)

Figure 2:
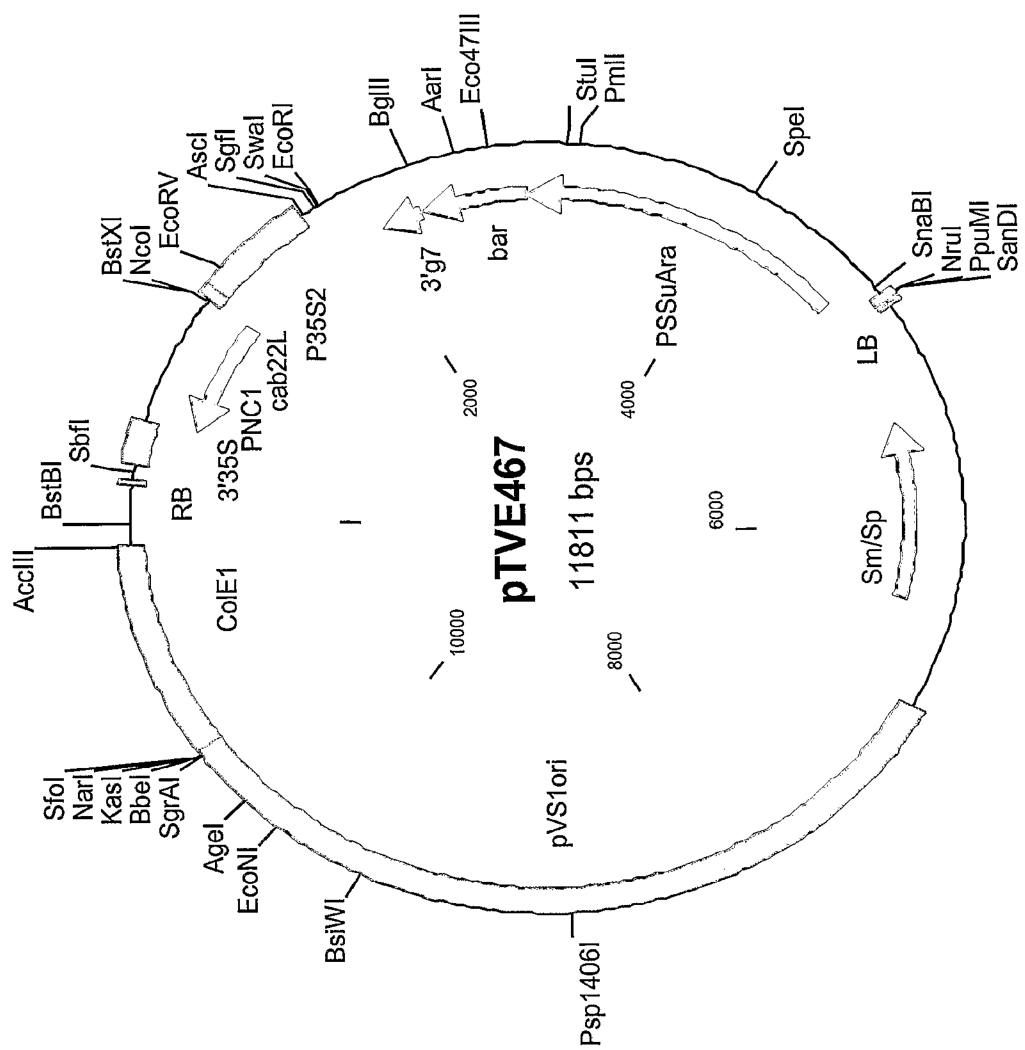
FIGS. 2 to 11 are schematic representations of the various T-DNA vectors comprising DNA regions encoding enzymes from the NAD salvage pathway or the NAD de novo synthesis pathway under control of plant-expressible control elements. Abbreviations used are: RB: right T-DNA border; 3'35S: transcription termination and polyadenylation signal from CaMV 35S transcript; Cab22L: untranslated leader sequence of the Cab22L transcript; P35S2: CaMV 35S promoter; 3' g7: transcription termination and polyadenylation signal from *Agrobacterium tumefaciens* T-DNA gene 7; bar: phosphinotricin acetyltransferase coding region; pSSUAra promoter of the Rubisco small subunit transcript from *Arabidopsis*; LB; left T-DNA border; Sm/Sp: Spectinomycin and streptomycin resistance gene; pVS1ori; origin of VS1 suitable for replication in *Agrobacterium*; ColE1: origin of replication; NLS: nuclear localization signal; PNC1: DNA region coding for nicotinamidase from *Saccharomyces cereviseae*; npt1: the nicotinate phosphoribosyltransferase from *Saccharomyces cereviseae*; nma1: nicotinic acid mononucleotide adenyl transferase 1 from *Saccharomyces cereviseae*; nma2: nicotinic acid mononucleotide adenyl transferase 2 from *Saccharomyces cereviseae*; qns1: NAD synthetase (QNS1) from *Saccharomyces cerevisea.*

This chimeric gene was introduced in a T-DNA vector, between the left and right border sequences from the T-DNA, together with a selectable marker gene providing resistance to the herbicide phosphinotricin, to yield pTVE467 (SEQ ID 25). T-DNA vector pTVE467 is schematically represented in FIG. 2.

T-DNA vector pTVE467 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1181 | 534 (C) | PNC1 coding region |
| 1250 | 1191 (C) | cab22 leader |
| 1781 | 1251 (C) | P35S2 promoter |
| 2293 | 2082 (C) | 3'g7 transcription termination signal |
| 2866 | 2315 (C) | bar coding region |
| 4592 | 2867 (C) | PSSuAra promoter |
| 4760 | 4784 | Left T-DNA border |
| 6352 | 5352 (C) | Sm/Sp resistance gene |
| 6875 | 10645 | pVS1origin of replication |
| 10646 | 11709 | ColE1 origin of replication |

pTVE468

A similar chimeric gene as present in pTVE467 was constructed, wherein the nicotinamidase was equipped with a conventional nuclear localization signal. The chimeric gene thus comprises the following operably linked DNA fragments:

- A promoter region from Cauliflower mosaic Virus (CaMV 35S);
- A DNA fragment of about 60 nt corresponding to the untranslated leader Cab22L;
- A DNA fragment of about 20 nt encoding a peptide comprising a nuclear localization signal (NLS),
- A DNA fragment encoding nicotinamidase from *Saccharomyces cereviseae* (SEQ ID NO 1); whereby the NLS signal is fused in frame;
- A fragment of the 3' untranslated end from the 35 S transcript of CaMV (3' 35S)

Figure 3:
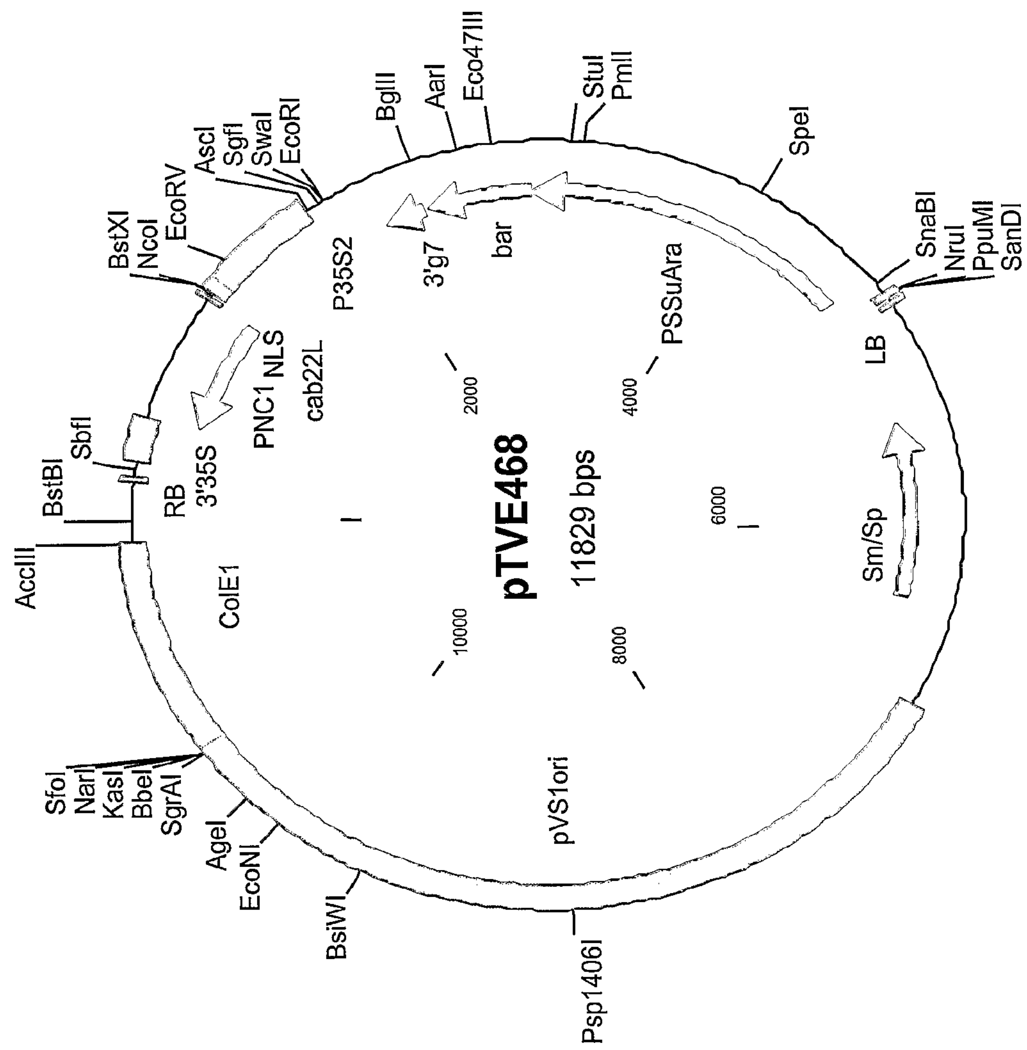

This chimeric gene was introduced in a T-DNA vector, between the left and right border sequences from the T-DNA, together with a selectable marker gene providing resistance to the herbicide phosphinotricin, to yield pTVE468 (SEQ ID 26). T-DNA vector pTVE468 is schematically represented in FIG. 3.

T-DNA vector pTVE468 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1169 | 534 (C) | PNC1 coding region |
| 1187 | 1167 (C) | Nuclear localization signal |
| 1268 | 1209 (C) | cab22 leader |
| 1799 | 1269 (C) | P35S2 promoter |
| 2311 | 2100 (C) | 3'g7 transcription termination signal |
| 2884 | 2333 (C) | bar coding region |
| 4610 | 2885 (C) | PSSuAra promoter |
| 4778 | 4802 | Left T-DNA border |
| 6370 | 5370 (C) | Sm/Sp resistance gene |
| 6893 | 10663 | pVS1origin of replication |
| 10664 | 11727 | ColE1 origin of replication |

pTVE469

To increase stress resistance in plants, a chimeric gene was constructed using conventional techniques comprising the following DNA fragments in order:

A promoter region from Cauliflower mosaic Virus (CaMV 35S);

A DNA fragment of about 60 bp corresponding to the untranslated leader Cab22L;

A DNA fragment encoding nicotinate phosphoribosyltransferase from *Saccharomyces cereviseae* (NPT1; SEQ ID NO 3);

A fragment of the 3' untranslated end from the 35 S transcript of CaMV (3' 35S)

Figure 4:
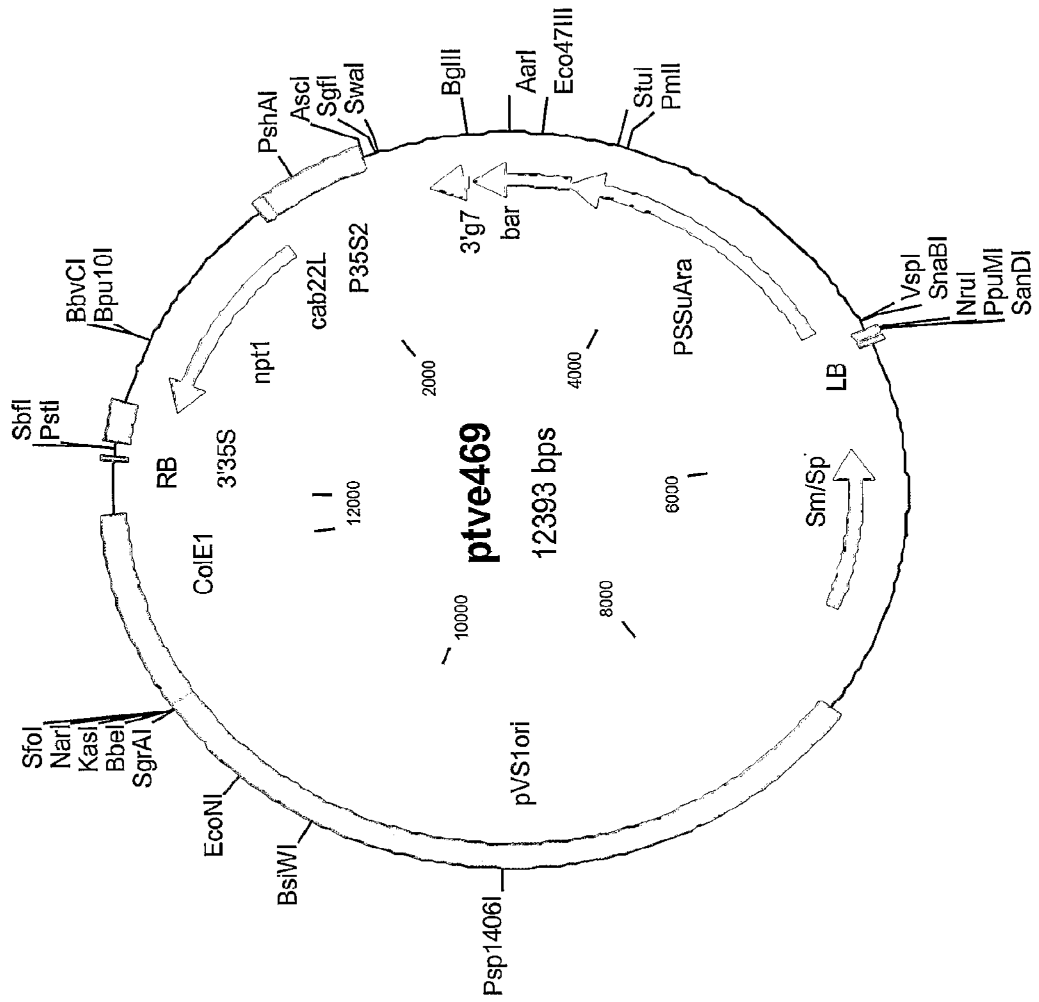

This chimeric gene was introduced in a T-DNA vector, between the left and right border sequences from the T-DNA, together with a selectable marker gene providing resistance to the herbicide phosphinotricin, to yield pTVE469 (SEQ ID 27). T-DNA vector pTVE469 is schematically represented in FIG. 4.

T-DNA vector pTVE469 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1765 | 534 (C) | NPT1 coding region |
| 1832 | 1773 (C) | cab22 leader |
| 2363 | 1833 (C) | P35S2 promoter |
| 2875 | 2664 (C) | 3'g7 transcription termination signal |
| 3448 | 2897 (C) | bar coding region |
| 5175 | 3449 (C) | PSSuAra promoter |
| 5342 | 5366 | Left T-DNA border |
| 6934 | 5934 (C) | Sm/Sp resistance gene |
| 7457 | 11227 | pVS1origin of replication |
| 11228 | 12291 | ColE1 origin of replication |

pTVE470

A similar chimeric gene as present in pTVE469 was constructed, wherein the nicotinate phosphoribosyltransferase from *Saccharomyces cereviseae* was equipped with a conventional nuclear localization signal The chimeric gene thus comprises the following operably linked DNA fragments:

A promoter region from Cauliflower mosaic Virus (CaMV 35S);

A DNA fragment of about 60 nt corresponding to the untranslated leader Cab22L;

A DNA fragment of about 20 nt encoding a peptide comprising a nuclear localization signal (NLS), A DNA fragment encoding nicotinate phosphoribosyltransferase from *Saccharomyces cereviseae* (NPT1; SEQ ID NO 3); whereby the NLS signal is fused in frame;

A fragment of the 3' untranslated end from the 35 S transcript of CaMV (3' 35S)

Figure 5:
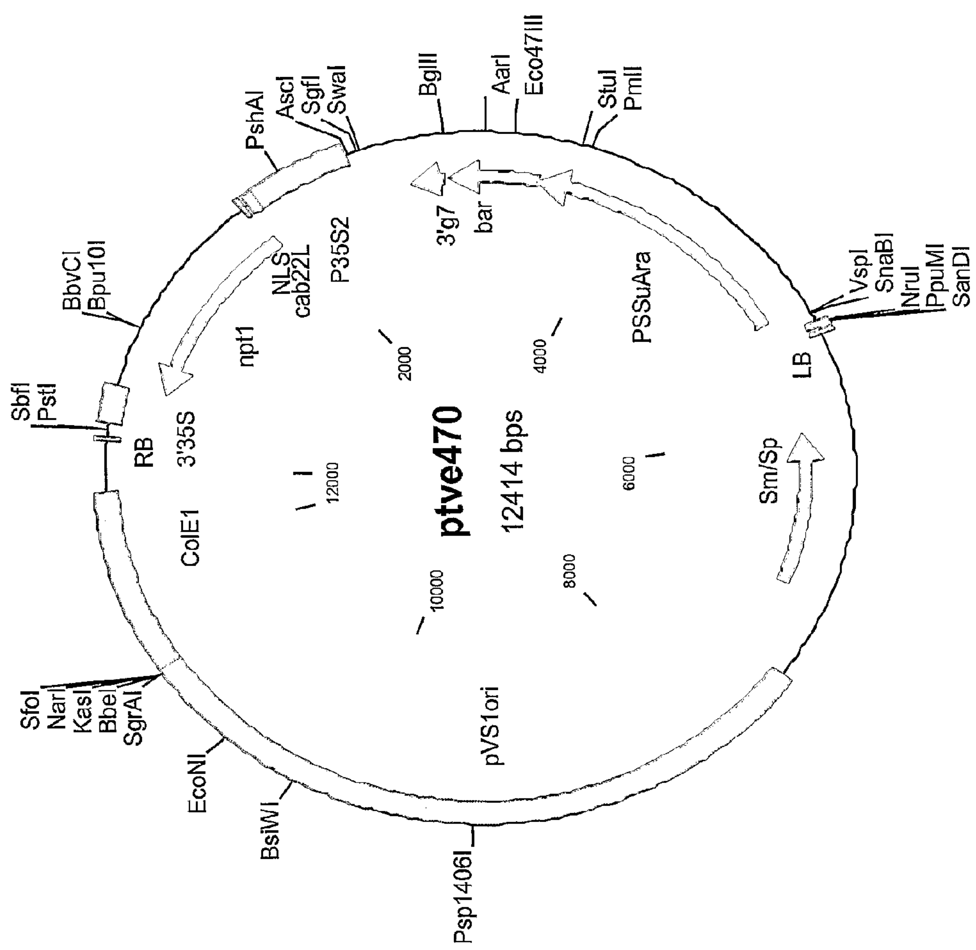

This chimeric gene was introduced in a T-DNA vector, between the left and right border sequences from the T-DNA, together with a selectable marker gene providing resistance to the herbicide phosphinotricin, to yield pTVE470 (SEQ ID 28). T-DNA vector pTVE470 is schematically represented in FIG. 5.

T-DNA vector pTVE470 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1787 | 534 (C) | NPT1 coding region |
| 1775 | 1755 (C) | Nuclear localization signal SV40 |
| 1853 | 1794 (C) | cab22 leader |
| 2384 | 1854 (C) | P35S2 promoter |
| 2896 | 2685 (C) | 3'g7 transcription termination signal |
| 3469 | 2918 (C) | bar coding region |
| 5195 | 3470 (C) | PSSuAra promoter |
| 5363 | 5387 | Left T-DNA border |
| 6955 | 5955 (C) | Sm/Sp resistance gene |
| 7478 | 11248 | pVS1origin of replication |
| 11249 | 12312 | ColE1 origin of replication |

pTVE496

To increase stress resistance in plants, a chimeric gene was constructed using conventional techniques comprising the following DNA fragments in order:

A promoter region from Cauliflower mosaic Virus (CaMV 35S);

A DNA fragment of about 60 bp corresponding to the untranslated leader Cab22L;

A DNA fragment encoding nicotinic acid mononucleotide adenyl transferase 1 from *Saccharomyces cereviseae* (NMA1; SEQ ID NO 5);

A fragment of the 3' untranslated end from the 35 S transcript of CaMV (3' 35S)

Figure 6:
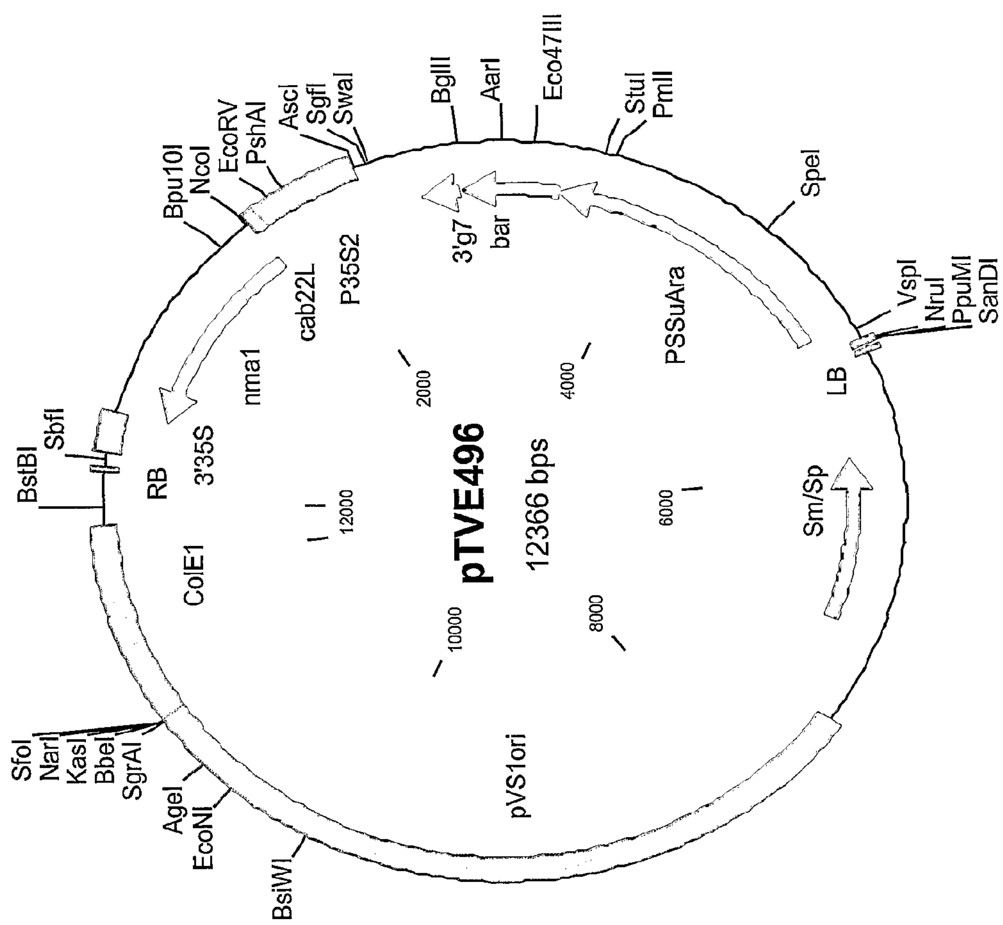

This chimeric gene was introduced in a T-DNA vector, between the left and right border sequences from the T-DNA, together with a selectable marker gene providing resistance to the herbicide phosphinotricin, to yield pTVE496 (SEQ ID 29). T-DNA vector pTVE496 is schematically represented in FIG. 6.

T-DNA vector pTVE496 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1739 | 534 (C) | NMA1 coding region |
| 1805 | 1746 (C) | cab22 leader |
| 2336 | 1806 (C) | P35S2 promoter |
| 2848 | 2637 (C) | 3'g7 transcription termination signal |
| 3421 | 2870 (C) | bar coding region |
| 5147 | 3422 (C) | PSSuAra promoter |

-continued

| Start (nt) | End (nt) | |
|---|---|---|
| 5315 | 5339 | Left T-DNA border |
| 6907 | 5907 (C) | Sm/Sp resistance gene |
| 7430 | 11200 | pVS1origin of replication |
| 11201 | 12264 | ColE1 origin of replication |

pTVE497

A similar chimeric gene as present in pTVE496 was constructed, wherein the nicotinic acid mononucleotide adenyl transferase 1 from *Saccharomyces cereviseae* was equipped with a conventional nuclear localization signal The chimeric gene thus comprises the following operably linked DNA fragments:

- A promoter region from Cauliflower mosaic Virus (CaMV 35S);
- A DNA fragment of about 60 nt corresponding to the untranslated leader Cab22L;
- A DNA fragment of about 20 nt encoding a peptide comprising a nuclear localization signal (NLS),
- A DNA fragment encoding nicotinic acid mononucleotide adenyl transferase 1 from *Saccharomyces cereviseae* (NMA1; SEQ ID NO 5); whereby the NLS signal is fused in frame;
- A fragment of the 3' untranslated end from the 35 S transcript of CaMV (3' 35S)

Figure 7:
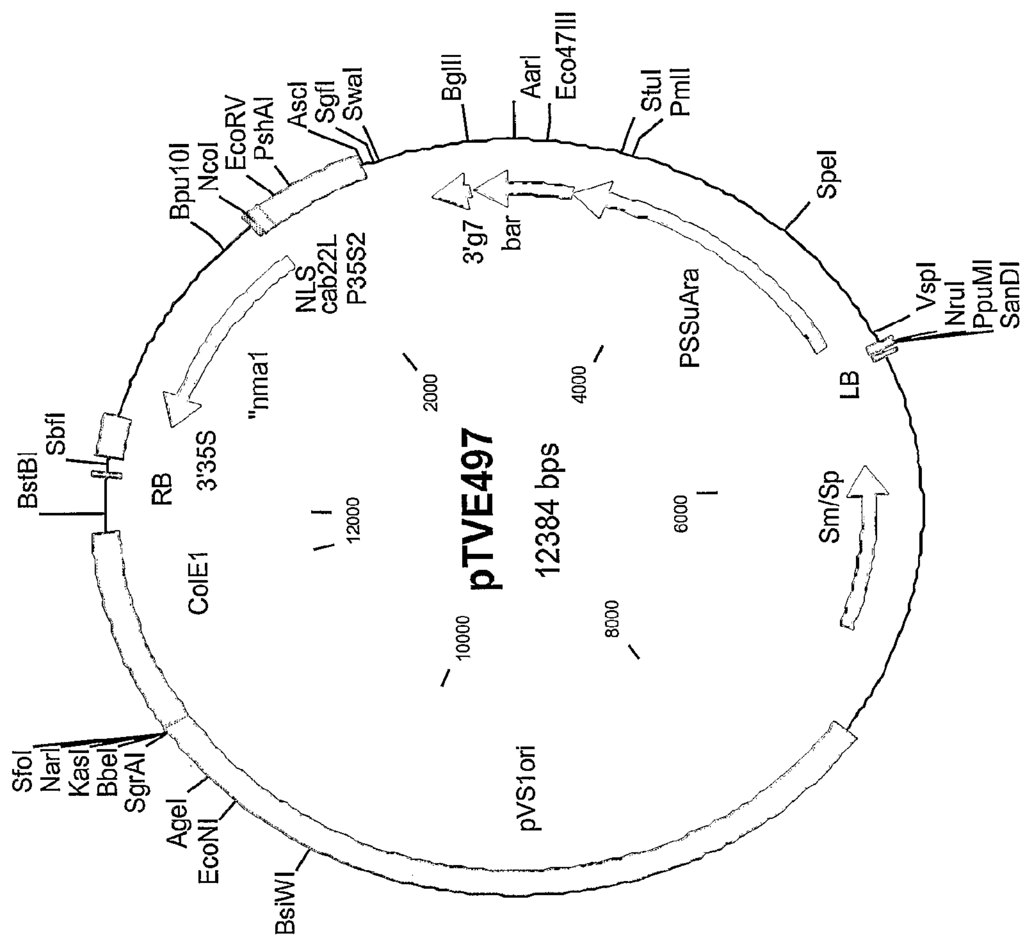

This chimeric gene was introduced in a T-DNA vector, between the left and right border sequences from the T-DNA, together with a selectable marker gene providing resistance to the herbicide phosphinotricin, to yield pTVE497 (SEQ ID 30). T-DNA vector pTVE497 is schematically represented in FIG. 7.

T-DNA vector pTVE497 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1757 | 534 (C) | NMA1 coding region |
| 1748 | 1731 (C) | Nuclear localization signal SV40 |
| 1823 | 1764 (C) | cab22 leader |
| 2354 | 1824 (C) | P35S2 promoter |
| 2866 | 2655 (C) | 3'g7 transcription termination signal |
| 3439 | 2888 (C) | bar coding region |
| 5165 | 3440 (C) | PSSuAra promoter |
| 5333 | 5357 | Left T-DNA border |
| 6925 | 5925 (C) | Sm/Sp resistance gene |
| 7448 | 11218 | pVS1origin of replication |
| 11219 | 12282 | ColE1 origin of replication |

pTVE500

To increase stress resistance in plants, a chimeric gene was constructed using conventional techniques comprising the following DNA fragments in order:

- A promoter region from Cauliflower mosaic Virus (CaMV 35S);
- A DNA fragment of about 60 bp corresponding to the untranslated leader Cab22L;
- A DNA fragment encoding nicotinic acid mononucleotide adenyl transferase 2 from *Saccharomyces cereviseae* (NMA2; SEQ ID No. 7);
- A fragment of the 3' untranslated end from the 35S transcript of CaMV (3' 35S).

Figure 8:
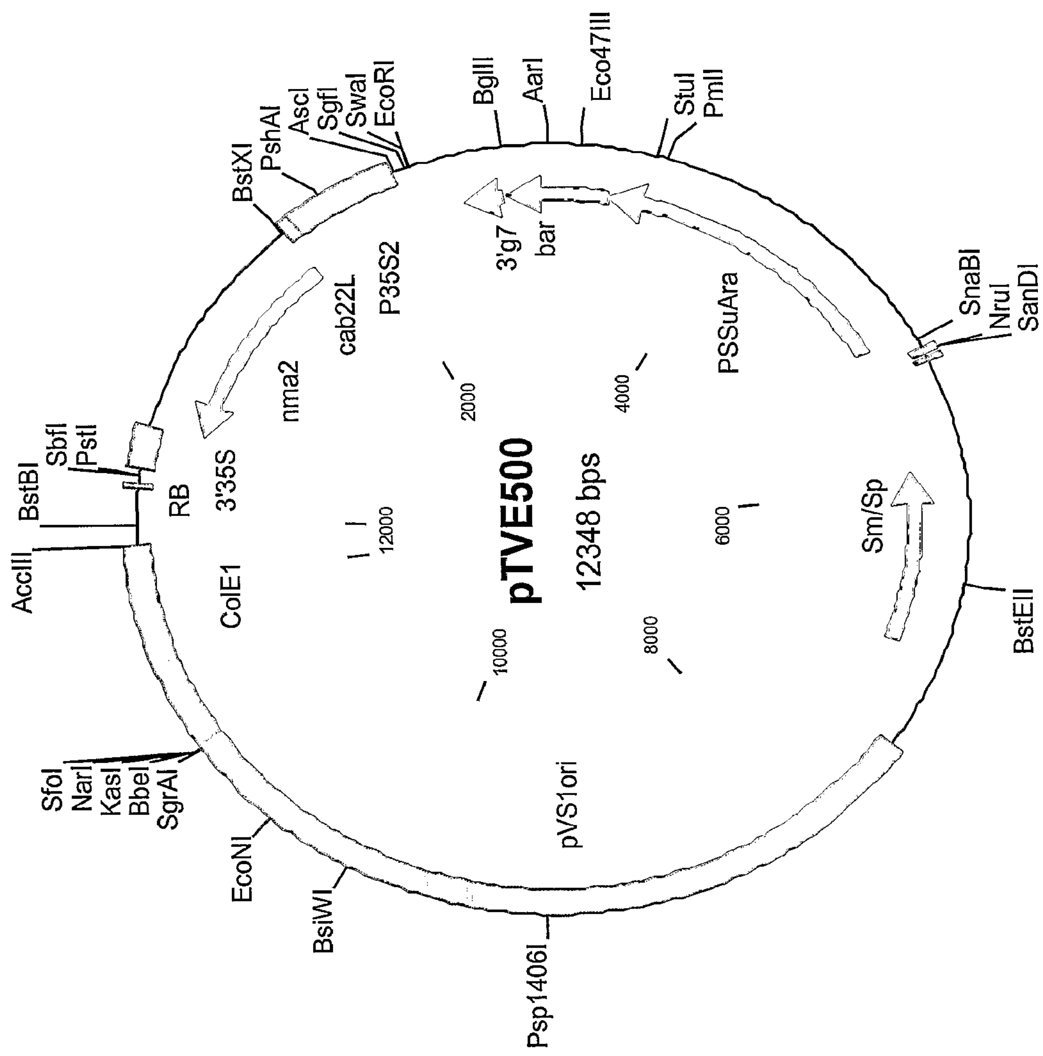

This chimeric gene was introduced in a T-DNA vector, between the left and right border sequences from the T-DNA, together with a selectable marker gene providing resistance to the herbicide phosphinotricin, to yield pTVE500 (SEQ ID 31). T-DNA vector pTVE500 is schematically represented in FIG. 8.

T-DNA vector pTVE500 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1721 | 534 (C) | NMA2 coding region |
| 1787 | 1728 (C) | cab22 leader |
| 2318 | 1788 (C) | P35S2 promoter |
| 2830 | 2619 C) | 3'g7 transcription termination signal |
| 3403 | 2852 (C) | bar coding region |
| 5129 | 3404 (C) | PSSuAra promoter |
| 5297 | 5321 | Left T-DNA border |
| 6889 | 5889 (C) | Sm/Sp resistance gene |
| 7412 | 11182 | pVS1origin of replication |
| 11183 | 12246 | ColE1 origin of replication |

pTVE501

A similar chimeric gene as present in pTVE500 was constructed, wherein the nicotinic acid mononucleotide adenyl transferase 2 from *Saccharomyces cereviseae* was equipped with a conventional nuclear localization signal The chimeric gene thus comprises the following operably linked DNA fragments:

- A promoter region from Cauliflower mosaic Virus (CaMV 35S);
- A DNA fragment of about 60 nt corresponding to the untranslated leader Cab22L;
- A DNA fragment of about 20 nt encoding a peptide comprising a nuclear localization signal (NLS),
- A DNA fragment encoding nicotinic acid mononucleotide adenyl transferase 2 from *Saccharomyces cereviseae* (NMA2; SEQ ID No. 7); whereby the NLS signal is fused in frame;
- A fragment of the 3' untranslated end from the 35 S transcript of CaMV (3' 35S)

Figure 9:
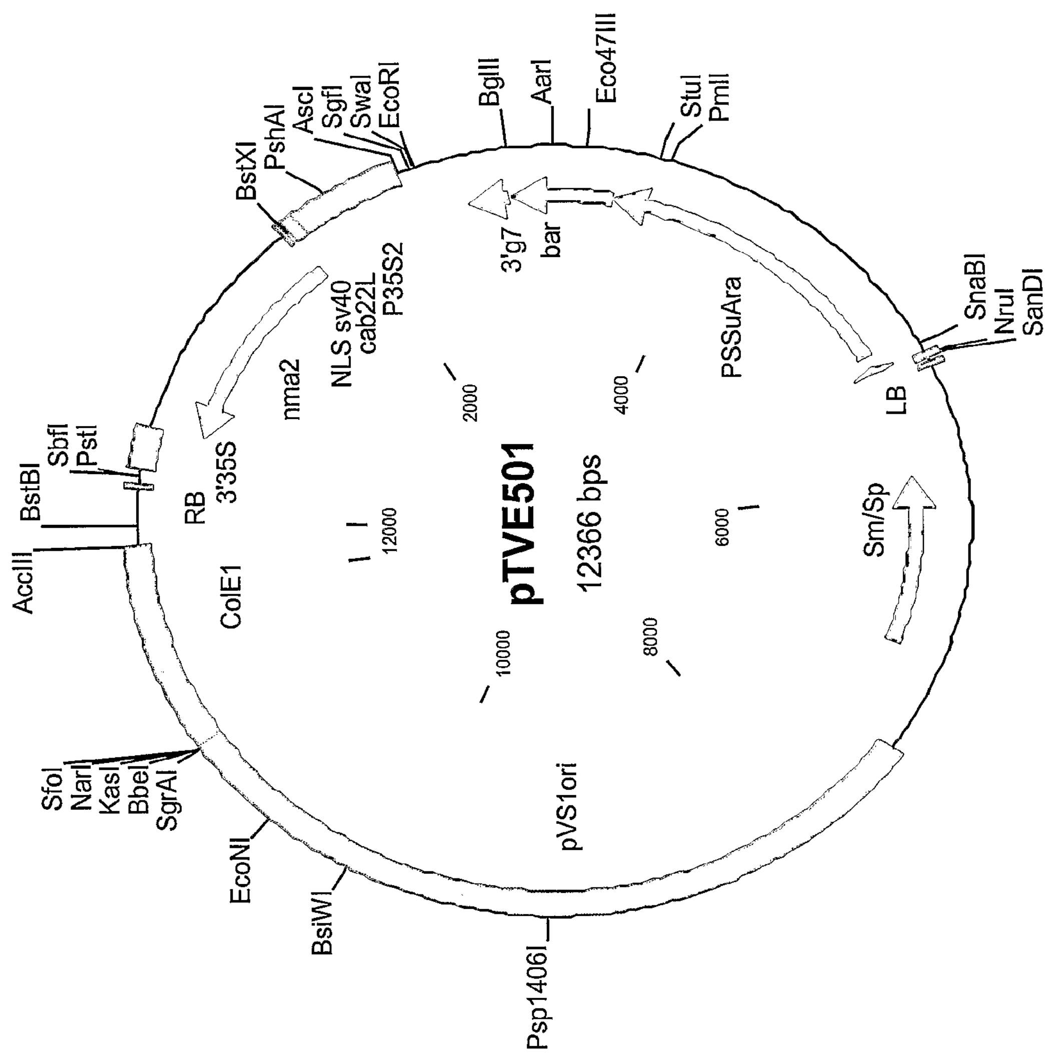

This chimeric gene was introduced in a T-DNA vector, between the left and right border sequences from the T-DNA, together with a selectable marker gene providing resistance to the herbicide phosphinotricin, to yield pTVE502 (SEQ ID 32). T-DNA vector pTVE501 is schematically represented in FIG. 9.

T-DNA vector pTVE501 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1739 | 534 (C) | NMA2 coding region |
| 1733 | 1713 (C) | Nuclear localization signal SV40 |
| 1805 | 1746 (C) | cab22 leader |
| 2336 | 1806 (C) | P35S2 promoter |
| 2848 | 2637 (C) | 3'g7 transcription termination signal |
| 3421 | 2870 (C) | bar coding region |
| 5165 | 3440 (C) | PSSuAra promoter |
| 5315 | 5339 | Left T-DNA border |
| 6907 | 5907 (C) | Sm/Sp resistance gene |

-continued

| Start (nt) | End (nt) | |
|---|---|---|
| 7430 | 11200 | pVS1origin of replication |
| 11201 | 12264 | ColE1 origin of replication |

pTVE502

To increase stress resistance in plants, a chimeric gene was constructed using conventional techniques comprising the following DNA fragments in order:

- A promoter region from Cauliflower mosaic Virus (CaMV 35S);
- A DNA fragment of about 60 bp corresponding to the untranslated leader Cab22L;
- A DNA fragment encoding NAD synthase from *Saccharomyces cereviseae* (QNS1; SEQ ID No. 9);
- A fragment of the 3' untranslated end from the $^{35}$S transcript of CaMV (3' 35S).

Figure 10:
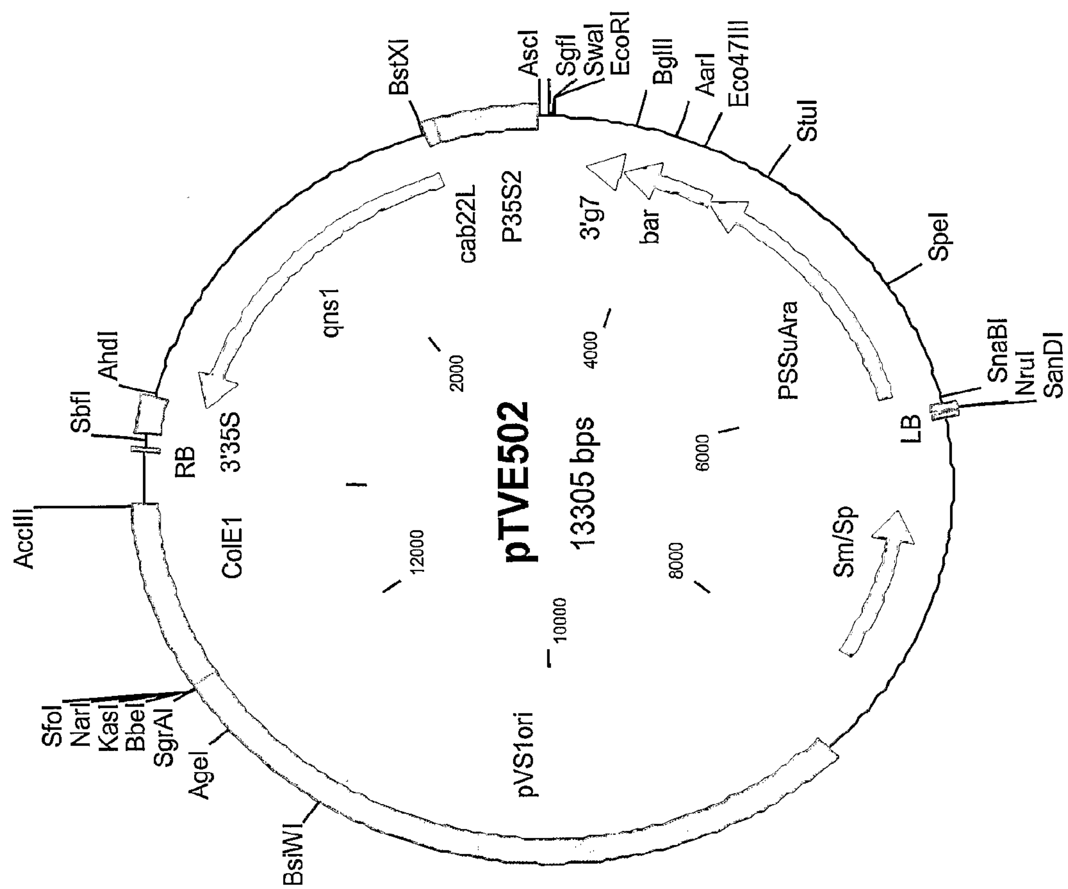

This chimeric gene was introduced in a T-DNA vector, between the left and right border sequences from the T-DNA, together with a selectable marker gene providing resistance to the herbicide phosphinotricin, to yield pTVE502 (SEQ ID 33). T-DNA vector pTVE502 is schematically represented in FIG. 10.

T-DNA vector pTVE502 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 2678 | 534 (C) | QNS1 coding region |
| 2744 | 2685 (C) | cab22 leader |
| 3275 | 2745 (C) | P35S2 promoter |
| 3787 | 3576 (C) | 3'g7 transcription termination signal |
| 4360 | 3809 (C) | bar coding region |
| 6086 | 4361 (C) | PSSuAra promoter |
| 6254 | 6278 | Left T-DNA border |
| 7846 | 6846 (C) | Sm/Sp resistance gene |
| 8369 | 12139 | pVS1origin of replication |
| 12140 | 13203 | ColE1 origin of replication |

pTVE503

A similar chimeric gene as present in pTVE502 was constructed, wherein the NAD synthase from *Saccharomyces cereviseae* was equipped with a conventional nuclear localization signal The chimeric gene thus comprises the following operably linked DNA fragments:

- A promoter region from Cauliflower mosaic Virus (CaMV 35S);
- A DNA fragment of about 60 nt corresponding to the untranslated leader Cab22L;
- A DNA fragment of about 20 nt encoding a peptide comprising a nuclear localization signal (NLS),
- A DNA fragment encoding NAD synthase from *Saccharomyces cereviseae* (QNS1; SEQ ID No. ç); whereby the NLS signal is fused in frame;
- A fragment of the 3' untranslated end from the 35 S transcript of CaMV (3' 35S)

Figure 11:
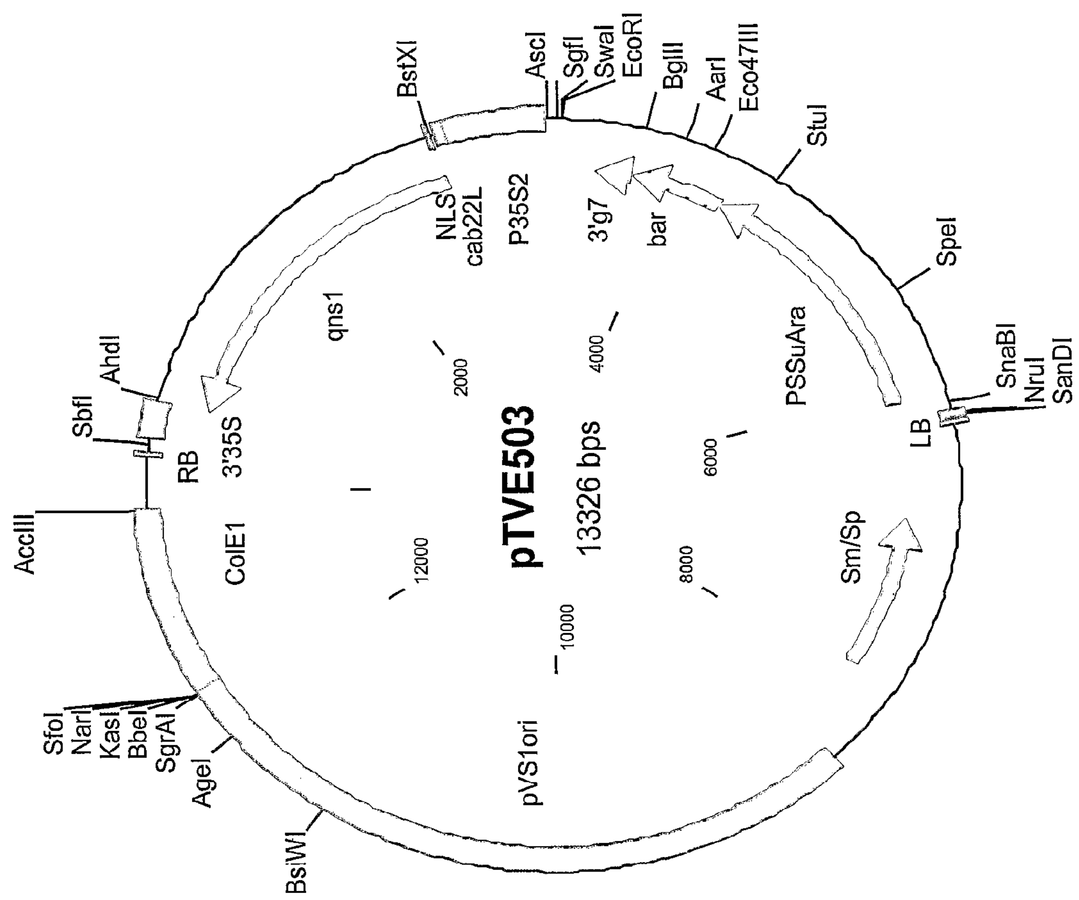

This chimeric gene was introduced in a T-DNA vector, between the left and right border sequences from the T-DNA, together with a selectable marker gene providing resistance to the herbicide phosphinotricin, to yield pTVE503 (SEQ ID No. 34). T-DNA vector pTVE503 is schematically represented in FIG. 11.

T-DNA vector pTVE503 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 2699 | 534 (C) | QNS1 coding region |
| 2690 | 2670 (C) | Nuclear localization signal SV40 |
| 2765 | 2706 (C) | cab22 leader |
| 3296 | 2766 (0) | P35S2 promoter |
| 3808 | 3597 (C) | 3'g7 transcription termination signal |
| 4381 | 3830 (C) | bar coding region |
| 6107 | 4382 (C) | PSSuAra promoter |
| 6275 | 6299 | Left T-DNA border |
| 7867 | 6867 (C) | Sm/Sp resistance gene |
| 8390 | 12610 | pVS1origin of replication |
| 12161 | 13224 | ColE1 origin of replication |

The T-DNA vectors were introduced into *Agrobacterium* strains comprising a helper Ti-plasmid using conventional methods. The chimeric genes were introduced into *Arabidopsis* plants by *Agrobacterium* mediated transformation as described in the art.

Example 2

Analysis of Transgenic *Arabidopsis* Lines Comprising the Chimeric Genes Described in Example 1

Seed of transgenic *Arabidopsis* lines (T1-generation) expressing the yeast genes of the NAD-salvage pathway, obtained as described in Example 1 were germinated and grown on medium containing 15 mg $L^{-1}$ phosphinotricin (PPT). *Arabidopsis thaliana* cv Col-0 was used as a control.

All plants were subjected to high light stress. Two week old plants grown at 30 μEinstein $m^{-2}$ $sec^{-1}$ were transferred to 250 μEinstein $m^{-2}$ $sec^{-1}$ (high light) for 6 hours, followed by 8 hours in the dark and again 8 hours high light.

After this treatment, NADH content and superoxide radicals content were determined for all lines and compared to measurement of the same compounds in transgenic and control lines grown under low light conditions. The results are summarized in Table 1.

Transgenic plants exhibited a higher NADH content under high light than control plants, and produced less reactive oxygen species under high light than control plants. No difference was observed between constructs wherein the encoded NAD salvage pathway enzyme was equipped with a nuclear localization signal or not.

Transgenic plant lines were also phenotypically scored for tolerance to high light stress conditions. To this end, plants were grown in vitro at low light conditions (30 μEinstein $m^{-2}$ $sec^{-1}$) for two weeks and transferred for 3 days to high light conditions (250 μEinstein $m^{-2}$ $sec^{-1}$; 16 hrs light-8 hrs dark). After the high light treatment the plants were returned to low light conditions and grown for another three days before scoring the phenotype.

Whereas control plants were small, and had started flowering (stress-induced), the plants of the transgenic lines comprising the chimeric genes as described in Example 1 were larger than the control plants and only had started to bolt.

TABLE 1

High light tolerance of transgenic *Arabidopsis* lines over-expressing the chimeric yeast genes as described in Example 1.

| Chimeric genes | Segregation for PPT tolerance | % NADH versus low light control | | % superoxides versus low light control | |
|---|---|---|---|---|---|
| | | Low light | High light | Low light | High light |
| Control | — | 100 | 68 | 100 | 145 |
| PNC1 (NLS) line 1 | 3:1 | 108 | 128 | 80 | 73 |
| PNC1 (NLS) line 2 | 3:1 | 139 | 128 | 82 | 76 |
| NPT1 line 1 | 6:1 | 128 | 147 | 66 | 70 |
| NPT1 line 2 | 6:1 | 122 | 135 | 82 | 76 |
| NPT1 (NLS) | 12:1 | 106 | 150 | 61 | 80 |

STANDARD ERROR OF MEAN <10%

Example 3

Protocols for Measurement of NADH Content and Superoxide Content

Intracellular NAD(P)H Quantification Using a Water-Soluble Tetrazolium Salt

REFERENCE

Jun Nakamura, Shoji Asakura, Susan D. Hester, Gilbert de Murcia, Keith W. Caldecott and James A. Swenberg (2003) Quantitation of intracellular NAD(P)H can monitor an imbalance of DNA single strand break repair in base excision repair deficient cells in real time. Nucleic Acids Research 31(17), e104.

Plant Material
- Most plant material can be used:
  - In vitro grown *Arabidopsis* shoots 14-18 days old but NOT flowering
  - Hypocotyl explants of oilseed rape Cell Counting Kit-8 (CCK-8)
- Sopachem n.v./Belgium
- 72A, Avenue du Laarbeeklaan—1090 Brussels
- Belgium
- Contents:
- 5 mL bottles containing 5 mMol/L WST-8 (tetrazolium salt), 0.2 mMol/L 1-Methoxy PMS, 150 mMol/L NaCl
- Reaction solution:
  - 10 mL 25 mM K-phosphate buffer pH7.4
  - 0.5 mL CCK-8
  - 0.1 mM 1-Methoxy-5-methylphenazinium methyl sulfate (=1-Methoxyphenazine methosulfate): 1 μL/mL of 100 mM stock (MW=336.4; 100 mg in 2.973 mL water)
  - 1 drop Tween20/25 mL Procedure
- Harvest plant material and put in 25 mM K-phosphate buffer pH7.4
  - e.g.: 150 oilseed rape hypocotyl explants
    - 1 gr *Arabidopsis* shoots (without roots)
- Replace buffer with reaction solution
  - 15 mL for 1 gr *Arabidopsis* shoots
  - 15 mL for 150 oilseed rape hypocotyl explants
- Incubate at 26° C. in the dark for about ½ hour (follow reaction)
- Measure the absorbance of the reaction solution at 450 nm
- Measuring Superoxide Production by Quantifying the Reduction of XTT Ref.: De Block, M., De Brouwer, D. (2002) A simple and robust in vitro assay to quantify the vigour of oilseed rape lines and hybrids. Plant Physiol. Biochem. 40, 845-852

A. *Brassica Napus*

Media and Reaction Buffers
- Sowing medium (medium 201):
  - Half concentrated Murashige and Skoog salts
  - 2% sucrose
  - pH 5.8
  - 0.6% agar (Difco Bacto Agar)
  - 250 mg/l triacillin
- Callus inducing medium A2S3:
  - MS medium, 0.5 g/l Mes (pH 5.8), 3% sucrose, 40 mg/l adenine-$SO_4$, 0.5% agarose, 1 mg/l 2,4-D, 0.25 mg/l NAA, 1 mg/l BAP, 250 mg/l triacillin
- Reaction Buffer:
  - 25 mM K-phosphate buffer pH 8
- 1 mM sodium, 3'-{1-[phenylamino-carbonyl]-3,4-tetrazolium}-bis(4-methoxy-6-nitro)=XTT (BioVectra, Canada) (MW 674.53)
- Dissolve XTT by careful warming solution (±37° C.) (cool down to room temperature before use)
  - 1 drop Tween20 for 25 ml buffer Sterilization of Seeds—Pregermination of Seeds—Growing of the Seedlings
- Seeds are soaked in 70% ethanol for 2 min, then surface-sterilized for 15 min in a sodium hypochlorite solution (with about 6% active chlorine) containing 0.1% Tween20. Finally, the seeds are rinsed with 11 of sterile tap water.

Incubate seeds for at least one hour in sterile tap water (to allow diffusion from seeds of components that may inhibit germination).

Seeds are put in 250 ml erlenmeyer flasks containing 50 ml of sterile tap water (+250 mg/l triacillin). Shake for about 20 hours.

Seeds from which the radicle is protruded are put in Vitro Vent containers from Duchefa containing about 125 ml of sowing medium (10 seeds/vessel, not too many to reduce loss of seed by contamination). The seeds are germinated at ±24° C. and 10-30 μEinstein $s^{-1}m^2$ with a daylength of 16 h.
- P.S.: For calculating the amount of seeds that have to be sawn: 5 hypocytyl segments/seedling Preculture of the hypocotyl explants and induction of stress
- 12-14 days after sowing, the hypocotyls are cut in about 7-10 mm segments.
- The hypocotyl explants (25 hypocotyls/Optilux Petridish, Falcon S1005, Denmark) are cultured for 5 days on medium A2S3 at 25° C. (at 10-30 μEinstein $s^{-1}m^{-2}$).
  - P.S.: 150 hypocotyl explants are used per condition.
- Induction of stress:
- Transfer hypocotyl explants to A2S3 medium containing respectively 0, 25 and 50 mg/l acetylsalicylic acid.

Incubate for about 24 hours at 25° C. and 10-30 μEinstein $s^{-1}m^{-2}$ with a daylength of 16 h.

XTT-Assay

Transfer 150 hypocotyl explants to a 50 ml Falcon tube.

Wash with reaction buffer (without XTT).

Add 20 mL reaction buffer+XTT.

(explants have to be submerged, but do not vacuum infiltrate)

Incubate in the dark at 26° C.

Follow the reaction by measuring the absorption of the reaction medium at 470 nm B. *Arabidopsis Thaliana*

Media and Reaction Buffers

Plant medium:

Half concentrated Murashige and Skoog salts

B5 vitamins 1.5% sucrose pH 5.8

0.7% Difco agar

Incubation medium:

½ concentrated MS-salts

1% sucrose 0.5 g/L MES pH 5.8

1 drop Tween20 for 25 ml medium

Reaction buffer:

25 mM K-phosphate buffer pH 8

1 mM sodium, 3'-{1-[phenylamino-carbonyl]-3,4-tetrazolium}-bis(4-methoxy-6-nitro)=XTT (BioVectra, Canada) (MW 674.53)

Dissolve XTT by careful warming solution (±37° C.) (cool down to room temperature before use)

1 drop Tween20 for 25 ml buffer

*Arabidopsis* Plants

*Arabidopsis* lines: control (mother line from which tested lines were derived) lines to test Sterilization of *Arabidopsis* seeds:

2 min. 70% ethanol 10 min. bleach (6% active chlorine)+1 drop Tween 20 for 20 ml solution wash 5 times with sterile tap water P.S.: sterilization is done in 2 ml eppendorf tubes

*Arabidopsis* seeds sink to the bottom of the tube, allowing removal of the liquids by means of a 1 ml pipetman Pregermination of seeds:

In 9 cm Optilux Petridishes (Falcon) containing 12 ml sterile tap water.

Low light overnight to 24 hours.

Growing of *Arabidopsis* plants

Seeds are sown in Intergrid Tissue Culture disks of Falcon (nr. 3025) containing±125 ml of plant medium: 1 seed/grid.

Plants are grown at 24° C.

30 μEinstein $s^{-1}m^{-2}$ 16 hours light-8 hours dark for about 18 days (before bolting)

P.S.: 1 g of plant material (shoots without roots)/line/condition are needed to carry out the assay. 1 g shoots corresponds with 40-60 plants.

Induction of Stress

Paraquat

Harvest *Arabidopsis* shoots (without roots)

Put 1 g shoots in incubation medium (shoots have to be submerged, but do not vacuum infiltrate) containing respectively 0, 5 and 10 μM paraquat Incubation medium: ±150 ml in Intergrid Tissue Culture disks of Falcon (nr. 3025)

Incubate at 24° C. in the dark for ±24 hours and 30-50 μEinstein $s^{-1}m^{-2}$ with a daylength of 16 h.

High Light

Transfer half of the plates to high light (250 μEinstein $s^{-1}m^{-2}$) and incubate for 4 to 20 hours XTT-Assay Harvest shoots (without roots) from agar plates (high light stress) or from liquid incubation medium (paraquat stress) and put them in 50 ml Falcon tubes containing reaction buffer (without XTT)

Replace reaction buffer with buffer containing XTT (15 mL/gr)

Shoots have to be submerged, but do not vacuum infiltrate

Incubate in the dark at 26° C.

Follow the reaction by measuring the absorption of the reaction medium at 470 nm (about one hour)

Example 4

Increased Ozone Tolerance of *Arabidopsis thaliana* Plants Over-Expressing the Yeast Nicotineamidase (Pnc1) Gene The chimeric vector pTVE467 (Example 1) was used for transformation of *A. thaliana* ecotype Columbia. Primary transformants were analyzed by Southern-DNA- and Northern-RNA-blot analysis. One transgenic line was identified to carry a single copy of the Pnc1-transgene construct and to have a high steady state level of transgenic full-length Pnc1-mRNA (20 pg/5 μg total RNA).

6 weeks after germination 100 individual plants each of the single copy transgenic line and of wild-type Columbia as a control, were exposed to ozone in fumigation chambers. During 2 consecutive days the plants were treated for 5 h/day with ozone concentrations of 250, 350 and 500 ppb respectively. After treatment all plants were visually screened for ozone injury manifested as necrotic lesions. The results are summarized in Table 2. At 500 ppb ozone exposure nearly all plants showed necrotic lesions whereas at the 2 lower ozone concentrations a significantly lower percentage of transgenic plants were injured.

In addition, the evolution of the vitality performance index (PI) was determined for all plants of the transgenic line and of the wild-type plants under increasing ozone concentration. PI can be calculated by the formula: PI=(ABS/CS)×(TR/CS)×(ET/CS). (ABS=flux of photons absorbed by the antenna pigments Chl*; CS=cross section; TR=energy trapped by the reaction centre and converted into redox energy; ET=electron flux further downstream leading to $CO_2$ fixation) In the transgenic line, the vitality performance index PI significantly increased with increasing ozone concentrations whereas this index remains constant in wild-type plants treated with increasing ozone concentrations. This can be explained by a physiological compensation response within the transgenic line to counteract the ozone damage.

TABLE 2

Increased ozone tolerance of *Arabidopsis thaliana* plants over-expressing the yeast nicotineamidase (Pnc1) gene.

| | 250 ppb $O_3$ | 350 ppb $O_3$ | 500 ppb $O_3$ |
|---|---|---|---|
| Wild-type | 45%* | 50% | 100% |
| Pnc1 | 20% | 25% | 100% |

*percentage of the plants exhibiting necrotic lesions

Furthermore, control plants, homozygous transgenic populations of plants comprising the chimeric Pnc1 gene as well as a heterozygous transgenic population, were subjected to ozone fumigations and scored for visible injury and various physiological responses compared to non-fumigated plants. The assessment included measurement of non-modulated fluorescence, modulated fluorescence, chlorophyll measurement and fresh weight determination.

Based on the visible injury and physiological responses, a ranking was made for each population indicating the degree of the ozone impact. The more negative the evaluation, the more sensitive the population's response to ozone.

Whereas the control non-transgenic population and the heterozygous transgenic population had a cumulative score of −13, the two homozygous transgenic populations had a score of −6 and −2 respectively. It is therefore clear that the homozygous transgenic populations performed statistically significantly better than the control plants.

The invention claimed is:

1. A method for obtaining a plant with increased stress resistance comprising introducing a chimeric gene into cells of a plant to obtain transgenic cells, said chimeric gene comprising the following operably linked DNA fragments:

a plant-expressible promoter;

a DNA region coding for a nicotinate phosphoribosyltransferase comprising the amino acid sequence of SEQ ID No. 4;

a 3' end region involved in transcription termination and polyadenylation;

regenerating said transgenic cells to obtain a population of transgenic plants; and selecting a plant from said population of transgenic plants which exhibits increased stress resistance or selecting a plant which exhibits a reduced level of reactive oxygen species or maintains a high level of NADH under stress conditions when compared to a similar non-transgenic plant.

2. The method according to claim 1, wherein said DNA region comprises the nucleotide sequence of SEQ ID No.: 3.

3. The method according to claim 1, further comprising the step of crossing said plant with another plant.

4. A chimeric gene comprising the following operably linked DNA fragments:

i. a plant-expressible promoter;

ii. a DNA region coding for a nicotinate phosphoribosyltransferase comprising the amino acid sequence of SEQ ID No. 4;

iii. a 3' end region involved in transcription termination and polyadenylation.

5. A plant cell comprising a chimeric gene as described in claim 4.

6. A plant comprising a chimeric gene as described in claim 4.

7. The plant of claim 6, wherein said plant is cotton, *Brassica* vegetables, oilseed rape, wheat, corn or maize, barley, sunflower, rice, oats, sugarcane, soybean, vegetables, chicory, lettuce, tomato, tobacco, potato, sugarbeet, papaya, pineapple, mango or *Arabidopsis thaliana.*

8. The plant according to claim 6, wherein said plant has a lower level of reactive oxygen species under stress conditions than a similar plant not comprising such a chimeric gene.

9. A seed of a plant according to claim 6, wherein said seed comprises a chimeric gene according to claim 4.

10. A method of increasing the stress resistance of a plant comprising introducing the chimeric gene according to claim 4, thereby increasing the stress resistance of said plant.

11. A method of decreasing the level of reactive oxygen species or maintaining the level of NAD in a plant or a plant cell under stress conditions comprising introducing the chimeric gene according to claim 4, thereby the level of reactive oxygen species or maintaining the level of NAD in said plant or plant cell.

12. The chimeric gene according to claim 4, wherein said DNA region comprises the nucleotide sequence of SEQ ID No.: 3.

13. The method according to claim 1, wherein said transgenic plants are single copy transgenic lines.

14. The plant according to claim 6, wherein said plant is a single copy transgenic line.

* * * * *

SEQUENCE LISTING

```
<160> NUMBER OF SEQ ID NOS: 34

<210> SEQ ID NO 1
<211> LENGTH: 651
<212> TYPE: DNA
<213> ORGANISM: Saccharomyces cerevisiae

<400> SEQUENCE: 1

atgaagactt taattgttgt tgatatgcaa aatgatttta tttcaccttt aggttccttg      60

actgttccaa aaggtgagga attaatcaat cctatctcgg atttgatgca agatgctgat     120

agagactggc acaggattgt ggtcaccaga gattggcacc cttccagaca tatttcgttc     180

gcaaagaacc ataaagataa agaaccctat tcaacataca cctaccactc tccaaggcca     240

ggcgatgatt ccacgcaaga gggtattttg tggcccgtac actgtgtgaa aaacacctgg     300

ggtagtcaat tggttgacca aataatggac caagtggtca ctaagcatat taagattgtc     360

gacaagggtt tcttgactga ccgtgaatac tactccgcct tccacgacat ctggaacttc     420

cataagaccg acatgaacaa gtacttagaa aagcatcata cagacgaggt ttacattgtc     480

ggtgtagctt tggagtattg tgtcaaagcc accgccattt ccgctgcaga actaggttat     540

aagaccactg tcctgctgga ttacacaaga cccatcagcg atgatcccga agtcatcaat     600

aaggttaagg aagagttgaa ggcccacaac atcaatgtcg tggataaata a              651


<210> SEQ ID NO 2
<211> LENGTH: 216
<212> TYPE: PRT
<213> ORGANISM: Saccharomyces cerevisiae

<400> SEQUENCE: 2

Met Lys Thr Leu Ile Val Val Asp Met Gln Asn Asp Phe Ile Ser Pro
1               5                   10                  15

Leu Gly Ser Leu Thr Val Pro Lys Gly Glu Glu Leu Ile Asn Pro Ile
            20                  25                  30

Ser Asp Leu Met Gln Asp Ala Asp Arg Asp Trp His Arg Ile Val Val
        35                  40                  45

Thr Arg Asp Trp His Pro Ser Arg His Ile Ser Phe Ala Lys Asn His
    50                  55                  60

Lys Asp Lys Glu Pro Tyr Ser Thr Tyr Thr Tyr His Ser Pro Arg Pro
65                  70                  75                  80

Gly Asp Asp Ser Thr Gln Glu Gly Ile Leu Trp Pro Val His Cys Val
                85                  90                  95

Lys Asn Thr Trp Gly Ser Gln Leu Val Asp Gln Ile Met Asp Gln Val
            100                 105                 110
```

```
Val Thr Lys His Ile Lys Ile Val Asp Lys Gly Phe Leu Thr Asp Arg
        115                 120                 125

Glu Tyr Tyr Ser Ala Phe His Asp Ile Trp Asn Phe His Lys Thr Asp
    130                 135                 140

Met Asn Lys Tyr Leu Glu Lys His His Thr Asp Glu Val Tyr Ile Val
145                 150                 155                 160

Gly Val Ala Leu Glu Tyr Cys Val Lys Ala Thr Ala Ile Ser Ala Ala
                165                 170                 175

Glu Leu Gly Tyr Lys Thr Thr Val Leu Leu Asp Tyr Thr Arg Pro Ile
            180                 185                 190

Ser Asp Asp Pro Glu Val Ile Asn Lys Val Lys Glu Glu Leu Lys Ala
        195                 200                 205

His Asn Ile Asn Val Val Asp Lys
    210                 215

<210> SEQ ID NO 3
<211> LENGTH: 1290
<212> TYPE: DNA
<213> ORGANISM: Saccharomyces cerevisiae

<400> SEQUENCE: 3

ttaggtccat ctgtgcgctt cgttatcacc actccaactt cgttcagtat atcccaattc      60

ctctttcact ctcttcacag tggcaggatc tcccatattt ttacctaagt tatcagaaat     120

tttgatagcg tgattaccat ttacttctaa tagtttgata acgatgttta acggctcact     180

tttaacctgg ggttctgact tcttacgaaa atcattagta aagtttgtgc caataccgaa     240

tgtggctagc attccattct ctttagctgc atgggagtaa gttattgcct tttcgacgtt     300

caaagaatcg gaataacaga taatcttcga gaatttaggc aatttcaaca cgtcatggta     360

atggtgggaa atctttttgg tatactcaac tgggtctcca gaatcttgtc taacaccgac     420

gtaagcatca gaatatggtg gacggaatga ttttaaaaag tcatcagttc caaaagtatc     480

cgttaatgct aaaccagcat tttttgcacc aaaagtattg atccaacaat ccattgcatt     540

tttattggca tgcaaataat cttcactaat agaagcgact cccataaccc actcgtgagc     600

cacagtaccg attggcttga ctccatattt cttggcaaat aaaatatttg atgtgcctaa     660

taatagcgat ttgtttctgt ctgggttacc gttcacagct ttcatgattc cttgcataat     720

tagatcttga gccttcagag atctacgacg tcttgtacca aattcactga atctaatacc     780

attatcaaac aaagtttccg ccttcttctc agcttgttct aattggtttt cgtagtccca     840

gtcgatgtca acaaatttaa aatacgcttc tgatattagg gacagtaagg ggatctcata     900

aaggatagta tccttccaac taccactgac taaaattttc aatttgtagt gggtgggctt     960

gccctcgatt tcttctgaag tgaaggaaat ctgctcttca gggtgtagtt tgtaattaga    1020

actgctaata tacttaatat atgccgatgg caaatatggg atttcctgtt ttaagtattc    1080

aatttcctct tctgtgaacc tcaaatttcc caaatacgaa aattgctctt tcaaccaatt    1140

aatggcttcc ttattgaagg tcaattggga cgacctgttg gtatatttat aagtaactgt    1200

aacatctgga aaattagtga agacagcagc atgcatcgta atcttgtaca tgtctgtgtc    1260

caaaagagac tttatcactg gttctgacat                                      1290

<210> SEQ ID NO 4
<211> LENGTH: 429
<212> TYPE: PRT
<213> ORGANISM: Saccharomyces cerevisiae
```

<400> SEQUENCE: 4

```
Met Ser Glu Pro Val Ile Lys Ser Leu Leu Asp Thr Asp Met Tyr Lys
1               5                   10                  15

Ile Thr Met His Ala Ala Val Phe Thr Asn Phe Pro Asp Val Thr Val
            20                  25                  30

Thr Tyr Lys Tyr Thr Asn Arg Ser Ser Gln Leu Thr Phe Asn Lys Glu
        35                  40                  45

Ala Ile Asn Trp Leu Lys Glu Gln Phe Ser Tyr Leu Gly Asn Leu Arg
    50                  55                  60

Phe Thr Glu Glu Glu Ile Glu Tyr Leu Lys Gln Glu Ile Pro Tyr Leu
65                  70                  75                  80

Pro Ser Ala Tyr Ile Lys Tyr Ile Ser Ser Ser Asn Tyr Lys Leu His
                85                  90                  95

Pro Glu Glu Gln Ile Ser Phe Thr Ser Glu Glu Ile Glu Gly Lys Pro
            100                 105                 110

Thr His Tyr Lys Leu Lys Ile Leu Val Ser Gly Ser Trp Lys Asp Thr
        115                 120                 125

Ile Leu Tyr Glu Ile Pro Leu Leu Ser Leu Ile Ser Glu Ala Tyr Phe
    130                 135                 140

Lys Phe Val Asp Ile Asp Trp Asp Tyr Glu Asn Gln Leu Glu Gln Ala
145                 150                 155                 160

Glu Lys Lys Ala Glu Thr Leu Phe Asp Asn Gly Ile Arg Phe Ser Glu
                165                 170                 175

Phe Gly Thr Arg Arg Arg Arg Ser Leu Lys Ala Gln Asp Leu Ile Met
            180                 185                 190

Gln Gly Ile Met Lys Ala Val Asn Gly Asn Pro Asp Arg Asn Lys Ser
        195                 200                 205

Leu Leu Leu Gly Thr Ser Asn Ile Leu Phe Ala Lys Lys Tyr Gly Val
    210                 215                 220

Lys Pro Ile Gly Thr Val Ala His Glu Trp Val Met Gly Val Ala Ser
225                 230                 235                 240

Ile Ser Glu Asp Tyr Leu His Ala Asn Lys Asn Ala Met Asp Cys Trp
                245                 250                 255

Ile Asn Thr Phe Gly Ala Lys Asn Ala Gly Leu Ala Leu Thr Asp Thr
            260                 265                 270

Phe Gly Thr Asp Asp Phe Leu Lys Ser Phe Arg Pro Pro Tyr Ser Asp
        275                 280                 285

Ala Tyr Val Gly Val Arg Gln Asp Ser Gly Asp Pro Val Glu Tyr Thr
    290                 295                 300

Lys Lys Ile Ser His His Tyr His Asp Val Leu Lys Leu Pro Lys Phe
305                 310                 315                 320

Ser Lys Ile Ile Cys Tyr Ser Asp Ser Leu Asn Val Glu Lys Ala Ile
                325                 330                 335

Thr Tyr Ser His Ala Ala Lys Glu Asn Gly Met Leu Ala Thr Phe Gly
            340                 345                 350

Ile Gly Thr Asn Phe Thr Asn Asp Phe Arg Lys Lys Ser Glu Pro Gln
        355                 360                 365

Val Lys Ser Glu Pro Leu Asn Ile Val Ile Lys Leu Leu Glu Val Asn
    370                 375                 380

Gly Asn His Ala Ile Lys Ile Ser Asp Asn Leu Gly Lys Asn Met Gly
385                 390                 395                 400
```

```
Asp Pro Ala Thr Val Lys Arg Val Lys Glu Glu Leu Gly Tyr Thr Glu
                405                 410                 415

Arg Ser Trp Ser Gly Asp Asn Glu Ala His Arg Trp Thr
            420                 425


<210> SEQ ID NO 5
<211> LENGTH: 1206
<212> TYPE: DNA
<213> ORGANISM: Saccharomyces cerevisiae

<400> SEQUENCE: 5

atggatccca caagagctcc ggatttcaaa ccgccatctg cagacgagga attgattcct      60

ccacccgacc cggaatctaa aattcccaaa tctattccaa ttattccata cgtcttagcc     120

gatgcgaatt cctctataga tgcacctttt aatattaaga ggaagaaaaa gcatcctaag     180

catcatcatc accatcatca cagtcgtaaa gaaggcaatg ataaaaaaca tcagcatatt     240

ccattgaacc aagacgactt tcaaccactt tccgcagaag tgtcttccga agatgatgac     300

gcggatttta gatccaagga gagatacggt tcagattcaa ccacagaatc agaaactaga     360

ggtgttcaga aatatcagat tgctgattta gaagaagttc cacatggaat cgttcgtcaa     420

gcaagaacct tggaagacta cgaattcccc tcacacagat tatcgaaaaa attactggat     480

ccaaataaac tgccgttagt aatagtagca tgtgggtctt tttcaccaat cacctacttg     540

catctaagaa tgtttgaaat ggctttagat gcaatctctg aacaaacaag gtttgaagtc     600

ataggtggat attactcccc tgttagtgat aactatcaaa agcaaggctt ggccccatcc     660

taccatagag tacgtatgtg tgaattggcc tgcgaaagaa cctcatcttg gttgatggtg     720

gatgcatggg agtcattgca accttcatac acaagaactg ccaaggtctt ggatcatttc     780

aatcacgaaa tcaatattaa gagaggtggt gtagctactg ttactggaga aaaaattggt     840

gtgaaaataa tgttgctggc tggtggtgac ctaatagagt caatgggtga accaaacgtt     900

tgggcggacg ccgatttaca tcacattctc ggtaattacg gttgtttgat tgtcgaacgt     960

actggttctg atgtaaggtc tttttgtta tcccatgata ttatgtatga acatagaagg    1020

aatattctta tcatcaagca actcatctat aatgatattt cttccacgaa agttcgtcta    1080

tttatcagac gcgccatgtc tgtacaatat ttgttaccta attcggtcat caggtatatc    1140

caagaacata gactatatgt ggaccaaacc gaacctgtta agcaagttct tggaaacaaa    1200

gaatga                                                                1206


<210> SEQ ID NO 6
<211> LENGTH: 401
<212> TYPE: PRT
<213> ORGANISM: Saccharomyces cerevisiae

<400> SEQUENCE: 6

Met Asp Pro Thr Arg Ala Pro Asp Phe Lys Pro Pro Ser Ala Asp Glu
1               5                   10                  15

Glu Leu Ile Pro Pro Pro Asp Pro Glu Ser Lys Ile Pro Lys Ser Ile
            20                  25                  30

Pro Ile Ile Pro Tyr Val Leu Ala Asp Ala Asn Ser Ser Ile Asp Ala
        35                  40                  45

Pro Phe Asn Ile Lys Arg Lys Lys Lys His Pro Lys His His His His
    50                  55                  60

His His His Ser Arg Lys Glu Gly Asn Asp Lys Lys His Gln His Ile
65                  70                  75                  80
```

-continued

```
Pro Leu Asn Gln Asp Asp Phe Gln Pro Leu Ser Ala Glu Val Ser Ser
                85                  90                  95

Glu Asp Asp Asp Ala Asp Phe Arg Ser Lys Glu Arg Tyr Gly Ser Asp
            100                 105                 110

Ser Thr Thr Glu Ser Glu Thr Arg Gly Val Gln Lys Tyr Gln Ile Ala
        115                 120                 125

Asp Leu Glu Glu Val Pro His Gly Ile Val Arg Gln Ala Arg Thr Leu
    130                 135                 140

Glu Asp Tyr Glu Phe Pro Ser His Arg Leu Ser Lys Lys Leu Leu Asp
145                 150                 155                 160

Pro Asn Lys Leu Pro Leu Val Ile Val Ala Cys Gly Ser Phe Ser Pro
                165                 170                 175

Ile Thr Tyr Leu His Leu Arg Met Phe Glu Met Ala Leu Asp Ala Ile
            180                 185                 190

Ser Glu Gln Thr Arg Phe Glu Val Ile Gly Gly Tyr Tyr Ser Pro Val
        195                 200                 205

Ser Asp Asn Tyr Gln Lys Gln Gly Leu Ala Pro Ser Tyr His Arg Val
    210                 215                 220

Arg Met Cys Glu Leu Ala Cys Glu Arg Thr Ser Ser Trp Leu Met Val
225                 230                 235                 240

Asp Ala Trp Glu Ser Leu Gln Pro Ser Tyr Thr Arg Thr Ala Lys Val
                245                 250                 255

Leu Asp His Phe Asn His Glu Ile Asn Ile Lys Arg Gly Gly Val Ala
            260                 265                 270

Thr Val Thr Gly Glu Lys Ile Gly Val Lys Ile Met Leu Leu Ala Gly
        275                 280                 285

Gly Asp Leu Ile Glu Ser Met Gly Glu Pro Asn Val Trp Ala Asp Ala
    290                 295                 300

Asp Leu His His Ile Leu Gly Asn Tyr Gly Cys Leu Ile Val Glu Arg
305                 310                 315                 320

Thr Gly Ser Asp Val Arg Ser Phe Leu Leu Ser His Asp Ile Met Tyr
                325                 330                 335

Glu His Arg Arg Asn Ile Leu Ile Ile Lys Gln Leu Ile Tyr Asn Asp
            340                 345                 350

Ile Ser Ser Thr Lys Val Arg Leu Phe Ile Arg Arg Ala Met Ser Val
        355                 360                 365

Gln Tyr Leu Leu Pro Asn Ser Val Ile Arg Tyr Ile Gln Glu His Arg
    370                 375                 380

Leu Tyr Val Asp Gln Thr Glu Pro Val Lys Gln Val Leu Gly Asn Lys
385                 390                 395                 400

Glu
```

```
<210> SEQ ID NO 7
<211> LENGTH: 1188
<212> TYPE: DNA
<213> ORGANISM: Saccharomyces cerevisiae

<400> SEQUENCE: 7

atggatccca ccaaagcacc cgattttaaa ccgccacagc caaatgaaga actacaacca      60

ccgccagatc caacacatac gataccaaaa tctggaccca tagttccata tgttttagct     120

gattataatt cttcgatcga tgctcctttc aatctcgaca tttacaaaac cctgtcgtca     180

aggaaaaaaa acgccaactc aagcaaccga atggaccata ttccattaaa tactagtgac     240

ttccagccac tatctcggga tgtatcatcg gaggaggaaa gtgaagggca atcgaatgga     300
```

```
attgacgcta ctctacagga tgttacgatg actgggaatt tgggggtact gaagagccaa     360

attgctgatt tggaagaagt tcctcacaca attgtaagac aagccagaac tattgaagat     420

tacgaatttc ctgtacacag attgacgaaa aagttacaag atcctgaaaa actgcctctg     480

atcatcgttg cttgtggatc attttctccc ataacatacc tacatttgag aatgtttgaa     540

atggctttag atgatatcaa tgagcaaacg cgttttgaag tggttggtgg ttatttttct     600

ccagtaagtg ataactatca aaagcgaggg ttagccccag cttatcatcg tgtccgcatg     660

tgcgaattag catgcgagcg gacatcatct tggttaatgg ttgatgcctg ggaatcttta     720

caatcaagtt atacaaggac agcaaaagtc ttggaccatt tcaatcatga aataaatatc     780

aagagaggtg gaatcatgac tgtagatggt gaaaaaatgg gcgtaaaaat catgttattg     840

gcaggcggtg atcttatcga atccatgggc gagcctcatg tgtgggctga ttcagacctg     900

caccatattt tgggtaatta tggatgtttg atcgtggaaa ggactggttc tgatgttagg     960

tccttcttgc tttcccatga tatcatgtat gaacacagaa gaaatatcct tattatcaaa    1020

caacttattt acaatgatat ttcctctacg aaagtgcggc ttttcatcag acgtggaatg    1080

tcagttcaat atcttcttcc aaactctgtc atccgttaca tccaagagta taatctatac    1140

attaatcaaa gtgaaccggt caagcaggtc ttggatagca aagagtga                 1188
```

<210> SEQ ID NO 8
<211> LENGTH: 395
<212> TYPE: PRT
<213> ORGANISM: Saccharomyces cerevisiae

<400> SEQUENCE: 8

```
Met Asp Pro Thr Lys Ala Pro Asp Phe Lys Pro Pro Gln Pro Asn Glu
1               5                   10                  15

Glu Leu Gln Pro Pro Pro Asp Pro Thr His Thr Ile Pro Lys Ser Gly
            20                  25                  30

Pro Ile Val Pro Tyr Val Leu Ala Asp Tyr Asn Ser Ser Ile Asp Ala
        35                  40                  45

Pro Phe Asn Leu Asp Ile Tyr Lys Thr Leu Ser Ser Arg Lys Lys Asn
    50                  55                  60

Ala Asn Ser Ser Asn Arg Met Asp His Ile Pro Leu Asn Thr Ser Asp
65                  70                  75                  80

Phe Gln Pro Leu Ser Arg Asp Val Ser Ser Glu Glu Glu Ser Glu Gly
                85                  90                  95

Gln Ser Asn Gly Ile Asp Ala Thr Leu Gln Asp Val Thr Met Thr Gly
            100                 105                 110

Asn Leu Gly Val Leu Lys Ser Gln Ile Ala Asp Leu Glu Glu Val Pro
        115                 120                 125

His Thr Ile Val Arg Gln Ala Arg Thr Ile Glu Asp Tyr Glu Phe Pro
    130                 135                 140

Val His Arg Leu Thr Lys Lys Leu Gln Asp Pro Glu Lys Leu Pro Leu
145                 150                 155                 160

Ile Ile Val Ala Cys Gly Ser Phe Ser Pro Ile Thr Tyr Leu His Leu
                165                 170                 175

Arg Met Phe Glu Met Ala Leu Asp Asp Ile Asn Glu Gln Thr Arg Phe
            180                 185                 190

Glu Val Val Gly Gly Tyr Phe Ser Pro Val Ser Asp Asn Tyr Gln Lys
        195                 200                 205
```

```
Arg Gly Leu Ala Pro Ala Tyr His Arg Val Arg Met Cys Glu Leu Ala
    210                 215                 220

Cys Glu Arg Thr Ser Ser Trp Leu Met Val Asp Ala Trp Glu Ser Leu
225                 230                 235                 240

Gln Ser Ser Tyr Thr Arg Thr Ala Lys Val Leu Asp His Phe Asn His
                245                 250                 255

Glu Ile Asn Ile Lys Arg Gly Gly Ile Met Thr Val Asp Gly Glu Lys
            260                 265                 270

Met Gly Val Lys Ile Met Leu Leu Ala Gly Gly Asp Leu Ile Glu Ser
        275                 280                 285

Met Gly Glu Pro His Val Trp Ala Asp Ser Asp Leu His His Ile Leu
    290                 295                 300

Gly Asn Tyr Gly Cys Leu Ile Val Glu Arg Thr Gly Ser Asp Val Arg
305                 310                 315                 320

Ser Phe Leu Leu Ser His Asp Ile Met Tyr Glu His Arg Arg Asn Ile
                325                 330                 335

Leu Ile Ile Lys Gln Leu Ile Tyr Asn Asp Ile Ser Ser Thr Lys Val
            340                 345                 350

Arg Leu Phe Ile Arg Arg Gly Met Ser Val Gln Tyr Leu Leu Pro Asn
        355                 360                 365

Ser Val Ile Arg Tyr Ile Gln Glu Tyr Asn Leu Tyr Ile Asn Gln Ser
    370                 375                 380

Glu Pro Val Lys Gln Val Leu Asp Ser Lys Glu
385                 390                 395
```

<210> SEQ ID NO 9
<211> LENGTH: 2145
<212> TYPE: DNA
<213> ORGANISM: Saccharomyces cerevisiae

<400> SEQUENCE: 9

```
atgtcacatc ttatcacttt agctacatgc aacttgaatc aatgggccct agattttgaa      60

ggtaatagag accgtatcct acagtccatt aagattgcca aagagagggg tgccaggtta     120

cgtgtcggcc cagaactgga aataactggc tacggatgtt tagatcattt tttagaaaat     180

gacgtttgcc ttcattcatg ggaaatgtat gctcaaatca ttaagaataa agaaacccat     240

ggattaatac ttgacattgg tatgcccgtt ctacacaaga atgttcgtta taattgtcgt     300

ttgttatcct tggatggtga gatattgttc ataagaccta agatttggtt agctaatgat     360

ggtaactata gggaaatgag atttttcaca ccttggatga aacctggcgt ggtggaggac     420

tttatccttc cacctgagat tcagaaagtt accggccaga gacttgtgcc atttggggac     480

gctgtgataa attcattgga tacatgcatt ggtacagaaa cttgtgaaga attgtttaca     540

cctcaatccc cccacatcgc catgtcttta gatggtgtgg aaatcatgac aaactcatct     600

ggttctcatc atgaactgcg taagttaaat aaaaggttag acctaatttt aaatgccact     660

aaacgttgtg gtggtgttta cttgtatgca aatcaaagag gttgtgatgg tgacagatta     720

tattatgatg gctgtgcact aattgccatc aatggtacaa ttgtagccca aggttcacaa     780

ttttcgctag atgatgtgga agtagttact gctactgtgg acctagaaga ggtgaggagt     840

tatcgtgcag ctgtcatgtc tcgtggccta caagcctcct tggcagaaat aaagttcaag     900

cgtattgata ttcctgtaga attggcttta atgacctcca gatttgatcc tacagtgtgt     960

ccaacaaaag tccgcgagcc tttctatcac tctcctgagg aagaaattgc actgggacct    1020

gcttgctgga tgtgggatta tttaagacgt tgtaacggaa cagggttttt ccttccctta    1080
```

-continued tctgggggca ttgactcttg tgcaactgca atgattgtcc actctatgtg ccgtttagtg 1140
accgacgctg ctcaaaatgg aaatgagcaa gttatcaaag acgttcgtaa gataacacgt 1200
agcggcgatg attggattcc agacagtcca caggatctag cctcaaaaat atttcactcc 1260
tgtttcatgg gtacggaaaa ttcatccaag gagacaagaa acagagcaaa ggacctttcc 1320
aatgcaattg gatcttacca cgtggattta aagatggact cattggtatc cagtgtggtg 1380
tccttattcg aagtagccac tggcaaaaaa ccaatataca aaatatttgg gggatctcaa 1440
atcgagaact tggctttaca aaacatccag gcgcgtctaa gaatggttct ttcttatctt 1500
tttgcgcaac tgttgccgtg ggttcgtggt atcccaaact cgggtggatt gttagtactt 1560
ggtagcgcaa atgttgatga gtgcttacgt gggtatctaa caaaatatga ctgctcctcc 1620
gcagatatca accctattgg gggtatttca aaaactgact tgaaaagatt cattgcctac 1680
gcatcaaaac aatataacat gccaatcttg aatgactttt taaacgctac accaactgca 1740
gaattagaac ctatgactaa agattacgtt caatcggatg agatagatat ggggatgacg 1800
tatgaagaat tgggcgtgtt tggttaccta agaaaggttg aaaaatgtgg tccttattct 1860
atgttcttaa aacttcttca tcaatggtcc ccaaagttaa cacctcgtca aatatctgaa 1920
aaggtgaaaa gatttttctt cttctatgcc atcaacagac acaagcaaac tgttttaact 1980
cctagttatc atgctgaaca gtattcacca gaagacaaca gatttgactt acgtcctttc 2040
ttaatcaacc caagatttcc atgggcttca agaaaaattg atgaagttgt cgagcagtgt 2100
gaagcacata aaggctcaac gcttgacatt atgtctattg attag 2145

<210> SEQ ID NO 10
<211> LENGTH: 714
<212> TYPE: PRT
<213> ORGANISM: Saccharomyces cerevisiae

<400> SEQUENCE: 10

Met Ser His Leu Ile Thr Leu Ala Thr Cys Asn Leu Asn Gln Trp Ala
1 5 10 15

Leu Asp Phe Glu Gly Asn Arg Asp Arg Ile Leu Gln Ser Ile Lys Ile
20 25 30

Ala Lys Glu Arg Gly Ala Arg Leu Arg Val Gly Pro Glu Leu Glu Ile
35 40 45

Thr Gly Tyr Gly Cys Leu Asp His Phe Leu Glu Asn Asp Val Cys Leu
50 55 60

His Ser Trp Glu Met Tyr Ala Gln Ile Ile Lys Asn Lys Glu Thr His
65 70 75 80

Gly Leu Ile Leu Asp Ile Gly Met Pro Val Leu His Lys Asn Val Arg
85 90 95

Tyr Asn Cys Arg Leu Leu Ser Leu Asp Gly Glu Ile Leu Phe Ile Arg
100 105 110

Pro Lys Ile Trp Leu Ala Asn Asp Gly Asn Tyr Arg Glu Met Arg Phe
115 120 125

Phe Thr Pro Trp Met Lys Pro Gly Val Val Glu Asp Phe Ile Leu Pro
130 135 140

Pro Glu Ile Gln Lys Val Thr Gly Gln Arg Leu Val Pro Phe Gly Asp
145 150 155 160

Ala Val Ile Asn Ser Leu Asp Thr Cys Ile Gly Thr Glu Thr Cys Glu
165 170 175

```
Glu Leu Phe Thr Pro Gln Ser Pro His Ile Ala Met Ser Leu Asp Gly
            180                 185                 190

Val Glu Ile Met Thr Asn Ser Ser Gly Ser His His Glu Leu Arg Lys
        195                 200                 205

Leu Asn Lys Arg Leu Asp Leu Ile Leu Asn Ala Thr Lys Arg Cys Gly
    210                 215                 220

Gly Val Tyr Leu Tyr Ala Asn Gln Arg Gly Cys Asp Gly Asp Arg Leu
225                 230                 235                 240

Tyr Tyr Asp Gly Cys Ala Leu Ile Ala Ile Asn Gly Thr Ile Val Ala
                245                 250                 255

Gln Gly Ser Gln Phe Ser Leu Asp Asp Val Glu Val Val Thr Ala Thr
            260                 265                 270

Val Asp Leu Glu Glu Val Arg Ser Tyr Arg Ala Ala Val Met Ser Arg
        275                 280                 285

Gly Leu Gln Ala Ser Leu Ala Glu Ile Lys Phe Lys Arg Ile Asp Ile
    290                 295                 300

Pro Val Glu Leu Ala Leu Met Thr Ser Arg Phe Asp Pro Thr Val Cys
305                 310                 315                 320

Pro Thr Lys Val Arg Glu Pro Phe Tyr His Ser Pro Glu Glu Glu Ile
                325                 330                 335

Ala Leu Gly Pro Ala Cys Trp Met Trp Asp Tyr Leu Arg Arg Cys Asn
            340                 345                 350

Gly Thr Gly Phe Phe Leu Pro Leu Ser Gly Gly Ile Asp Ser Cys Ala
        355                 360                 365

Thr Ala Met Ile Val His Ser Met Cys Arg Leu Val Thr Asp Ala Ala
    370                 375                 380

Gln Asn Gly Asn Glu Gln Val Ile Lys Asp Val Arg Lys Ile Thr Arg
385                 390                 395                 400

Ser Gly Asp Asp Trp Ile Pro Asp Ser Pro Gln Asp Leu Ala Ser Lys
                405                 410                 415

Ile Phe His Ser Cys Phe Met Gly Thr Glu Asn Ser Ser Lys Glu Thr
            420                 425                 430

Arg Asn Arg Ala Lys Asp Leu Ser Asn Ala Ile Gly Ser Tyr His Val
        435                 440                 445

Asp Leu Lys Met Asp Ser Leu Val Ser Ser Val Val Ser Leu Phe Glu
    450                 455                 460

Val Ala Thr Gly Lys Lys Pro Ile Tyr Lys Ile Phe Gly Gly Ser Gln
465                 470                 475                 480

Ile Glu Asn Leu Ala Leu Gln Asn Ile Gln Ala Arg Leu Arg Met Val
                485                 490                 495

Leu Ser Tyr Leu Phe Ala Gln Leu Leu Pro Trp Val Arg Gly Ile Pro
            500                 505                 510

Asn Ser Gly Gly Leu Leu Val Leu Gly Ser Ala Asn Val Asp Glu Cys
        515                 520                 525

Leu Arg Gly Tyr Leu Thr Lys Tyr Asp Cys Ser Ser Ala Asp Ile Asn
    530                 535                 540

Pro Ile Gly Gly Ile Ser Lys Thr Asp Leu Lys Arg Phe Ile Ala Tyr
545                 550                 555                 560

Ala Ser Lys Gln Tyr Asn Met Pro Ile Leu Asn Asp Phe Leu Asn Ala
                565                 570                 575

Thr Pro Thr Ala Glu Leu Glu Pro Met Thr Lys Asp Tyr Val Gln Ser
            580                 585                 590
```

```
Asp Glu Ile Asp Met Gly Met Thr Tyr Glu Glu Leu Gly Val Phe Gly
        595                 600                 605

Tyr Leu Arg Lys Val Glu Lys Cys Gly Pro Tyr Ser Met Phe Leu Lys
    610                 615                 620

Leu Leu His Gln Trp Ser Pro Lys Leu Thr Pro Arg Gln Ile Ser Glu
625                 630                 635                 640

Lys Val Lys Arg Phe Phe Phe Phe Tyr Ala Ile Asn Arg His Lys Gln
                645                 650                 655

Thr Val Leu Thr Pro Ser Tyr His Ala Glu Gln Tyr Ser Pro Glu Asp
            660                 665                 670

Asn Arg Phe Asp Leu Arg Pro Phe Leu Ile Asn Pro Arg Phe Pro Trp
        675                 680                 685

Ala Ser Arg Lys Ile Asp Glu Val Val Glu Gln Cys Glu Ala His Lys
    690                 695                 700

Gly Ser Thr Leu Asp Ile Met Ser Ile Asp
705                 710


<210> SEQ ID NO 11
<211> LENGTH: 597
<212> TYPE: DNA
<213> ORGANISM: Arabidopsis thaliana

<400> SEQUENCE: 11

atggcttcct catcaacgag aaagtacgag acacgaaagc gagatccaaa ctctaaaatc      60

gcagctcttc tcgttatcga catgcagaat cacttctcct ccatggccaa acccatcctc     120

aacaacgttc tcaccaccat cgacatctgc cgacgcgcct cagtccccgt attctttacg     180

cgtcacaacc acaaatcccc gaccgaccac ggcatgctcg gcgagtggtg taacggcgat     240

gtaatccttg acggaaccac cgattctgaa atcatccagg agatacaagg ccaagtaacc     300

ggaccagacg agatggtgga gaagaacacg tacagtgcgt ttaacaaaac ccgcctccag     360

gaaaacctgg aaaagatcgg agtaaaggag gtgatcgtga tcggagtgat gacgaacttg     420

tgctgtgaga caacggcgcg tgaagcgttt attaagggtt ttagggtttt tttctcgacg     480

gacgcgactg cgacgtttaa tgaggagctt cacgaggcta cgctaatgaa tctcgctttt     540

ggcttcgctt atctcgtcga ttgcgataaa ctccggcgaa gtctactcgg taactaa        597


<210> SEQ ID NO 12
<211> LENGTH: 198
<212> TYPE: PRT
<213> ORGANISM: Arabidopsis thaliana

<400> SEQUENCE: 12

Met Ala Ser Ser Ser Thr Arg Lys Tyr Glu Thr Arg Lys Arg Asp Pro
1               5                   10                  15

Asn Ser Lys Ile Ala Ala Leu Leu Val Ile Asp Met Gln Asn His Phe
            20                  25                  30

Ser Ser Met Ala Lys Pro Ile Leu Asn Asn Val Leu Thr Thr Ile Asp
        35                  40                  45

Ile Cys Arg Arg Ala Ser Val Pro Val Phe Phe Thr Arg His Asn His
    50                  55                  60

Lys Ser Pro Thr Asp His Gly Met Leu Gly Glu Trp Cys Asn Gly Asp
65                  70                  75                  80

Val Ile Leu Asp Gly Thr Thr Asp Ser Glu Ile Ile Gln Glu Ile Gln
                85                  90                  95
```

```
Gly Gln Val Thr Gly Pro Asp Glu Met Val Glu Lys Asn Thr Tyr Ser
            100                 105                 110

Ala Phe Asn Lys Thr Arg Leu Gln Glu Asn Leu Glu Lys Ile Gly Val
        115                 120                 125

Lys Glu Val Ile Val Ile Gly Val Met Thr Asn Leu Cys Cys Glu Thr
    130                 135                 140

Thr Ala Arg Glu Ala Phe Ile Lys Gly Phe Arg Val Phe Phe Ser Thr
145                 150                 155                 160

Asp Ala Thr Ala Thr Phe Asn Glu Glu Leu His Glu Ala Thr Leu Met
                165                 170                 175

Asn Leu Ala Phe Gly Phe Ala Tyr Leu Val Asp Cys Asp Lys Leu Arg
            180                 185                 190

Arg Ser Leu Leu Gly Asn
        195


<210> SEQ ID NO 13
<211> LENGTH: 597
<212> TYPE: DNA
<213> ORGANISM: Arabidopsis thaliana

<400> SEQUENCE: 13

atggcttctt catcatcgag aacgtacgag acacgaaagc gagagccaaa tcctaaaatc      60

gcagctcttc tcgtcatcga tatgcagaat cacttctact ctatggctga accaatcctc     120

caaaacgctc tcaccaccat cgacatctgc cgacgcgctt caatccccgt attcttcacg     180

cgccacaacc acaaatcccc aaccgaccac ggcatgctcg gagagtggtg gaacggcgat     240

ctaatcctcg acggaaccac tgattccgaa atcatcccgg aaatcaatcg ccaggtcacc     300

ggaccagacg aaatcgtgga gaagagcacg tacagtgcgt ttaacaacac gcaccttcag     360

gagaagctgg acaagatcgg agtgaaggag gtgatcgtta tcggagtgat gacgaaccta     420

tgctgtgaga cgacggcgcg tgaagcgttt gtaaaggggt ttagggtttt tttctcgacg     480

gacgcgactg cgacggttaa tgaagagctt cacgaggcta ctctaatgaa tctcgcgtat     540

ggctttgctt atctcgtcga ttgcgataga ctccggcgag gtctactcag tagttaa        597


<210> SEQ ID NO 14
<211> LENGTH: 198
<212> TYPE: PRT
<213> ORGANISM: Arabidopsis thaliana

<400> SEQUENCE: 14

Met Ala Ser Ser Ser Ser Arg Thr Tyr Glu Thr Arg Lys Arg Glu Pro
1               5                   10                  15

Asn Pro Lys Ile Ala Ala Leu Leu Val Ile Asp Met Gln Asn His Phe
            20                  25                  30

Tyr Ser Met Ala Glu Pro Ile Leu Gln Asn Ala Leu Thr Thr Ile Asp
        35                  40                  45

Ile Cys Arg Arg Ala Ser Ile Pro Val Phe Phe Thr Arg His Asn His
    50                  55                  60

Lys Ser Pro Thr Asp His Gly Met Leu Gly Glu Trp Trp Asn Gly Asp
65                  70                  75                  80

Leu Ile Leu Asp Gly Thr Thr Asp Ser Glu Ile Ile Pro Glu Ile Asn
                85                  90                  95

Arg Gln Val Thr Gly Pro Asp Glu Ile Val Glu Lys Ser Thr Tyr Ser
            100                 105                 110
```

```
Ala Phe Asn Asn Thr His Leu Gln Glu Lys Leu Asp Lys Ile Gly Val
        115                 120                 125

Lys Glu Val Ile Val Ile Gly Val Met Thr Asn Leu Cys Cys Glu Thr
    130                 135                 140

Thr Ala Arg Glu Ala Phe Val Lys Gly Phe Arg Val Phe Phe Ser Thr
145                 150                 155                 160

Asp Ala Thr Ala Thr Val Asn Glu Glu Leu His Glu Ala Thr Leu Met
                165                 170                 175

Asn Leu Ala Tyr Gly Phe Ala Tyr Leu Val Asp Cys Asp Arg Leu Arg
            180                 185                 190

Arg Gly Leu Leu Ser Ser
        195


<210> SEQ ID NO 15
<211> LENGTH: 591
<212> TYPE: DNA
<213> ORGANISM: Arabidopsis thaliana

<400> SEQUENCE: 15

atggccgaga gatggaggaa cacggctcta ctcgtcatcg acatgcagaa cgatttcata      60

gaggaaggtg ctgtgacgca agtgaaagga ggaaaatcta tagttcctaa tgttatcaga     120

gtcgtcgaac tcgcgaggca gcgtggtatt ctcgtaattt gggttgttcg agaacatgat     180

cgtcaaggaa gagatgttga attattcagg cgccataact acagttctga gaaagtcggg     240

ccagttatta aaggcaccgt aggagcagaa ttggttgatg gattgatgat caacgaagaa     300

gatgactata agattgtgaa aactcgtttc agtgctttct ttagtaccaa tcttcattcc     360

ttcttgcaaa cttcaggggt taccaagtta gtgattgctg gtgtgcaaac gccgaactgt     420

atccggcaaa cggtgtttga tgcagtggcg ctggattatc ccaatgtgac tgttattaca     480

gatgccacag ctgctgcaac accagagatc catactgcga atattcttga catgaagaat     540

attggagtca agactcctac attacacgag tggtccgaag aacttgcttg a              591


<210> SEQ ID NO 16
<211> LENGTH: 196
<212> TYPE: PRT
<213> ORGANISM: Arabidopsis thaliana

<400> SEQUENCE: 16

Met Ala Glu Arg Trp Arg Asn Thr Ala Leu Leu Val Ile Asp Met Gln
1               5                   10                  15

Asn Asp Phe Ile Glu Glu Gly Ala Val Thr Gln Val Lys Gly Gly Lys
            20                  25                  30

Ser Ile Val Pro Asn Val Ile Arg Val Val Glu Leu Ala Arg Gln Arg
        35                  40                  45

Gly Ile Leu Val Ile Trp Val Val Arg Glu His Asp Arg Gln Gly Arg
    50                  55                  60

Asp Val Glu Leu Phe Arg Arg His Asn Tyr Ser Ser Glu Lys Val Gly
65                  70                  75                  80

Pro Val Ile Lys Gly Thr Val Gly Ala Glu Leu Val Asp Gly Leu Met
                85                  90                  95

Ile Asn Glu Glu Asp Asp Tyr Lys Ile Val Lys Thr Arg Phe Ser Ala
            100                 105                 110

Phe Phe Ser Thr Asn Leu His Ser Phe Leu Gln Thr Ser Gly Val Thr
        115                 120                 125
```

```
Lys Leu Val Ile Ala Gly Val Gln Thr Pro Asn Cys Ile Arg Gln Thr
    130                 135                 140

Val Phe Asp Ala Val Ala Leu Asp Tyr Pro Asn Val Thr Val Ile Thr
145                 150                 155                 160

Asp Ala Thr Ala Ala Ala Thr Pro Glu Ile His Thr Ala Asn Ile Leu
                165                 170                 175

Asp Met Lys Asn Ile Gly Val Lys Thr Pro Thr Leu His Glu Trp Ser
            180                 185                 190

Glu Glu Leu Ala
        195


<210> SEQ ID NO 17
<211> LENGTH: 1680
<212> TYPE: DNA
<213> ORGANISM: Arabidopsis thaliana

<400> SEQUENCE: 17

atggagaaga aagaaaatgg tctcgatgga aagcaatcgg gtcgggtcat taacggaccc      60

actaacccga tggtcacacc tctgctcaac gatctttacc aattcaccat ggcttatgct     120

tattggaaag ctggcaaaca atctgagcga tctgtgtttg atctgtattt tcgtaagaat     180

ccttttggtg gagaatacac tatctttgct ggtttagaag aatgcatcaa atttctcgct     240

aatttcaatt tgactgatga agagatcgat ttcgttcgtg attcgttacc tggatgtgag     300

gaagctttct gtgattatct tcgagggctt gattgttctg acattgaagt gtatgccatt     360

tcggaaggat cagttgtttt tcctaaagtt cctttactca gaatcgaagg tcctgttgct     420

gtggtgcaat tgttggaaac tccattcctc aatctcatca attacgcatc tttggttgct     480

acaaatgcag caagacatcg gtttgttgca ggaaaatcta agcttctgct tgagtttggt     540

gctagaagag ctcagggacc cgatggtgca ataagcgcat caaagtattg ctaccttgga     600

ggttttgatg caacaagtaa tgttgcagcg ggaaaactgt ttgggatacc cctccgtggt     660

actcattccc atgcttttgt tagctcattc atgagccttg atgaaattgt tgacaaagtg     720

cttcgaagtt ctgatgggaa aagcacttgt aaggatttta tatgtttggt ccaaacttgc     780

ctaacaaaga ttcagaattc atcttcatta caaggaattt tttccgagac aaatcaaagc     840

gagcttgcag cgttcatttc atatgcactg gcattcccaa actcctttct cgctcttgta     900

gacacttatg atgtgatgaa gagtggtatt ccaaacttct gtgctgttgc tctagcactt     960

aatgaattgg gatacaaagc agtaggcatt agactggatt caggtgactt agcctatctt    1020

tctactgagg tcaggaaatt cttttgtgcc atagagagag acctcaaagt tcctgatttc    1080

gggaagatga tcgtcactgc tagtaacgat ctaaacgaag agacagtcga tgctctaaat    1140

aaacagggtc atgaagtaga tgcatttgga attggaacca acttagtgac ttgctatgcg    1200

caagctgcgt taggttgtgt tttcaaactt gtggaaataa acaatcagcc tcggatcaaa    1260

ctttctgaag atgttactaa ggtatcgatt ccatgtaaaa agcgtactta cagattgttc    1320

ggaaaagagg gttaccctct tgttgatata atgactggag agaacgaacc acctccaaag    1380

gtcggtgaaa ggttactttg ccgtcatcca ttcaatgaat caaaaagggc ttatgtggtt    1440

ccacaacgcg ttgaagagct tctgaaatgt tattggcgtg gcaatgcaga tgaagctagg    1500

gaagagctag agccattgaa agagctaaga aatcgttgca tcaaacagct cgaaaatatg    1560

cgacccgatc atatgagaag attaaaccct actccttata aggttagtgt cagcgccaag    1620

ttgtatgact tcatccactt cctctggctc aacgaagctc ctgtcggtga actgcattga    1680
```

<210> SEQ ID NO 18
<211> LENGTH: 559
<212> TYPE: PRT
<213> ORGANISM: Arabidopsis thaliana

<400> SEQUENCE: 18

```
Met Glu Lys Lys Glu Asn Gly Leu Asp Gly Lys Gln Ser Gly Arg Val
1               5                   10                  15

Ile Asn Gly Pro Thr Asn Pro Met Val Thr Pro Leu Leu Asn Asp Leu
            20                  25                  30

Tyr Gln Phe Thr Met Ala Tyr Ala Tyr Trp Lys Ala Gly Lys Gln Ser
        35                  40                  45

Glu Arg Ser Val Phe Asp Leu Tyr Phe Arg Lys Asn Pro Phe Gly Gly
    50                  55                  60

Glu Tyr Thr Ile Phe Ala Gly Leu Glu Glu Cys Ile Lys Phe Leu Ala
65                  70                  75                  80

Asn Phe Asn Leu Thr Asp Glu Glu Ile Asp Phe Val Arg Asp Ser Leu
                85                  90                  95

Pro Gly Cys Glu Glu Ala Phe Cys Asp Tyr Leu Arg Gly Leu Asp Cys
            100                 105                 110

Ser Asp Ile Glu Val Tyr Ala Ile Ser Glu Gly Ser Val Val Phe Pro
        115                 120                 125

Lys Val Pro Leu Leu Arg Ile Glu Gly Pro Val Ala Val Val Gln Leu
    130                 135                 140

Leu Glu Thr Pro Phe Leu Asn Leu Ile Asn Tyr Ala Ser Leu Val Ala
145                 150                 155                 160

Thr Asn Ala Ala Arg His Arg Phe Val Ala Gly Lys Ser Lys Leu Leu
                165                 170                 175

Leu Glu Phe Gly Ala Arg Arg Ala Gln Gly Pro Asp Gly Ala Ile Ser
            180                 185                 190

Ala Ser Lys Tyr Cys Tyr Leu Gly Gly Phe Asp Ala Thr Ser Asn Val
        195                 200                 205

Ala Ala Gly Lys Leu Phe Gly Ile Pro Leu Arg Gly Thr His Ser His
    210                 215                 220

Ala Phe Val Ser Ser Phe Met Ser Leu Asp Glu Ile Val Asp Lys Val
225                 230                 235                 240

Leu Arg Ser Ser Asp Gly Lys Ser Thr Cys Lys Asp Phe Ile Cys Leu
                245                 250                 255

Val Gln Thr Cys Leu Thr Lys Ile Gln Asn Ser Ser Ser Leu Gln Gly
            260                 265                 270

Ile Phe Ser Glu Thr Asn Gln Ser Glu Leu Ala Ala Phe Ile Ser Tyr
        275                 280                 285

Ala Leu Ala Phe Pro Asn Ser Phe Leu Ala Leu Val Asp Thr Tyr Asp
    290                 295                 300

Val Met Lys Ser Gly Ile Pro Asn Phe Cys Ala Val Ala Leu Ala Leu
305                 310                 315                 320

Asn Glu Leu Gly Tyr Lys Ala Val Gly Ile Arg Leu Asp Ser Gly Asp
                325                 330                 335

Leu Ala Tyr Leu Ser Thr Glu Val Arg Lys Phe Phe Cys Ala Ile Glu
            340                 345                 350

Arg Asp Leu Lys Val Pro Asp Phe Gly Lys Met Ile Val Thr Ala Ser
        355                 360                 365

Asn Asp Leu Asn Glu Glu Thr Val Asp Ala Leu Asn Lys Gln Gly His
    370                 375                 380
```

```
Glu Val Asp Ala Phe Gly Ile Gly Thr Asn Leu Val Thr Cys Tyr Ala
385                 390                 395                 400

Gln Ala Ala Leu Gly Cys Val Phe Lys Leu Val Glu Ile Asn Asn Gln
            405                 410                 415

Pro Arg Ile Lys Leu Ser Glu Asp Val Thr Lys Val Ser Ile Pro Cys
            420                 425                 430

Lys Lys Arg Thr Tyr Arg Leu Phe Gly Lys Glu Gly Tyr Pro Leu Val
        435                 440                 445

Asp Ile Met Thr Gly Glu Asn Glu Pro Pro Pro Lys Val Gly Glu Arg
    450                 455                 460

Leu Leu Cys Arg His Pro Phe Asn Glu Ser Lys Arg Ala Tyr Val Val
465                 470                 475                 480

Pro Gln Arg Val Glu Glu Leu Leu Lys Cys Tyr Trp Arg Gly Asn Ala
            485                 490                 495

Asp Glu Ala Arg Glu Glu Leu Glu Pro Leu Lys Glu Leu Arg Asn Arg
            500                 505                 510

Cys Ile Lys Gln Leu Glu Asn Met Arg Pro Asp His Met Arg Arg Leu
        515                 520                 525

Asn Pro Thr Pro Tyr Lys Val Ser Val Ser Ala Lys Leu Tyr Asp Phe
    530                 535                 540

Ile His Phe Leu Trp Leu Asn Glu Ala Pro Val Gly Glu Leu His
545                 550                 555


<210> SEQ ID NO 19
<211> LENGTH: 1674
<212> TYPE: DNA
<213> ORGANISM: Arabidopsis thaliana

<400> SEQUENCE: 19

atggagccga aagagaacgg ctcagaattg ggtcagaaga tcattgacgg accaacgaat      60

ccaatggtca cacctttact caatgatctt tatcaattca ccatggctta tgcttattgg     120

aaagctggca aacacaacga acgatccgtt ttcgatctgt attttcgtaa gaacccattt     180

ggtggtgagt acactgtgtt tgctggatta gaagagtgtg ttaagttctt agccaatttc     240

aaattgactg atgaagaaat cgatttcgtt caagagtgtt tgcctggatc tgaggaagct     300

ttttgtgatt atcttagagg gcttgattgt tctgatgttg aagtttatgc aattccggaa     360

ggatcagttg tttttcctaa agtacctctc atgagagttg aaggacctgt tggtgttgtt     420

caattgttgg aaactccatt cctcaatctt gtcaattttg catctttggt agctactaac     480

gcagctaggc atcgctttgt tgccggaaaa tctaagagtc tactcgagtt tggtgctcga     540

agggctcagg gtccggatgg tgcaataagc gcatcaaaat attgctacct tggaggtttt     600

gatgcaacaa gtaatgtagc agctggaaaa ctttttggga ttcctcttcg tggaacacac     660

tctcatgctt atgttagctc attcatgagt actgatgaga ttgttgacaa agtacttcgt     720

agtgctgatg ggaaaaccac gtgcgaggat tttgttagtc atgttcagac atggttaaaa     780

aagattcagt attcaccatc tctaagtggc attttctctg agacaaatca aagcgagcta     840

gcagctttca cctcatatgc actggcattc cccaaaactt ttcttgccct cgtagataca     900

tacgatgtga tgaagagtgg aatccctaac ttctgtgcag ttgctttagc actcaatgac     960

tttggatata aagcattagg tattagactg gattcaggtg atttagctta tctatctaga    1020

gaggccagaa atttcttctg cacggtagag agagaactaa aagtgcctgg ttttgggaag    1080

atggtcgtca ctgctagtaa tgatctaaat gaagagacga ttgacgcttt aaataaacag    1140
```

```
ggacatgagg tggatgcttt tggcatcggg acctacttgg tcacttgcta ttcacaagcg   1200

gccttaggtt gcgttttcaa acttgtggag ataaacaatc agcctcggat taaactttct   1260

gaagatgtta caaaggtatc aataccgtgt aaaaagcgaa gttacagatt atacggcaaa   1320

gaaggttacc ctctggtaga tataatgact ggagagaacg aaccacctcc aaaggttggt   1380

gagcgtttac tttgtcgtca cccattcaac gaatccaaaa gagcatatgt agtgccacaa   1440

cgtgtcgaag agctcctcaa atgttattgg cgtggaagtg cagatgaagc aagagaagta   1500

ttaccgcctt tgaaagagat aagagaccgt tgcatcaaac agctcgaaaa catgcgacct   1560

gatcatatga ggagattaaa cccaactcct tataaggtta gtgtaagcgc aaagctgtac   1620

gatttcatcc acttcttatg gctaaacgaa gcacctgttg gtgaattgca gtga         1674
```

<210> SEQ ID NO 20
<211> LENGTH: 557
<212> TYPE: PRT
<213> ORGANISM: Arabidopsis thaliana

<400> SEQUENCE: 20

```
Met Glu Pro Lys Glu Asn Gly Ser Glu Leu Gly Gln Lys Ile Ile Asp
1               5                   10                  15

Gly Pro Thr Asn Pro Met Val Thr Pro Leu Leu Asn Asp Leu Tyr Gln
            20                  25                  30

Phe Thr Met Ala Tyr Ala Tyr Trp Lys Ala Gly Lys His Asn Glu Arg
        35                  40                  45

Ser Val Phe Asp Leu Tyr Phe Arg Lys Asn Pro Phe Gly Gly Glu Tyr
    50                  55                  60

Thr Val Phe Ala Gly Leu Glu Glu Cys Val Lys Phe Leu Ala Asn Phe
65                  70                  75                  80

Lys Leu Thr Asp Glu Glu Ile Asp Phe Val Gln Glu Cys Leu Pro Gly
                85                  90                  95

Ser Glu Glu Ala Phe Cys Asp Tyr Leu Arg Gly Leu Asp Cys Ser Asp
            100                 105                 110

Val Glu Val Tyr Ala Ile Pro Glu Gly Ser Val Val Phe Pro Lys Val
        115                 120                 125

Pro Leu Met Arg Val Glu Gly Pro Val Gly Val Val Gln Leu Leu Glu
    130                 135                 140

Thr Pro Phe Leu Asn Leu Val Asn Phe Ala Ser Leu Val Ala Thr Asn
145                 150                 155                 160

Ala Ala Arg His Arg Phe Val Ala Gly Lys Ser Lys Ser Leu Leu Glu
                165                 170                 175

Phe Gly Ala Arg Arg Ala Gln Gly Pro Asp Gly Ala Ile Ser Ala Ser
            180                 185                 190

Lys Tyr Cys Tyr Leu Gly Gly Phe Asp Ala Thr Ser Asn Val Ala Ala
        195                 200                 205

Gly Lys Leu Phe Gly Ile Pro Leu Arg Gly Thr His Ser His Ala Tyr
    210                 215                 220

Val Ser Ser Phe Met Ser Thr Asp Glu Ile Val Asp Lys Val Leu Arg
225                 230                 235                 240

Ser Ala Asp Gly Lys Thr Thr Cys Glu Asp Phe Val Ser His Val Gln
                245                 250                 255

Thr Trp Leu Lys Lys Ile Gln Tyr Ser Pro Ser Leu Ser Gly Ile Phe
            260                 265                 270
```

```
Ser Glu Thr Asn Gln Ser Glu Leu Ala Ala Phe Thr Ser Tyr Ala Leu
        275                 280                 285

Ala Phe Pro Lys Thr Phe Leu Ala Leu Val Asp Thr Tyr Asp Val Met
    290                 295                 300

Lys Ser Gly Ile Pro Asn Phe Cys Ala Val Ala Leu Ala Leu Asn Asp
305                 310                 315                 320

Phe Gly Tyr Lys Ala Leu Gly Ile Arg Leu Asp Ser Gly Asp Leu Ala
                325                 330                 335

Tyr Leu Ser Arg Glu Ala Arg Asn Phe Phe Cys Thr Val Glu Arg Glu
            340                 345                 350

Leu Lys Val Pro Gly Phe Gly Lys Met Val Val Thr Ala Ser Asn Asp
        355                 360                 365

Leu Asn Glu Glu Thr Ile Asp Ala Leu Asn Lys Gln Gly His Glu Val
    370                 375                 380

Asp Ala Phe Gly Ile Gly Thr Tyr Leu Val Thr Cys Tyr Ser Gln Ala
385                 390                 395                 400

Ala Leu Gly Cys Val Phe Lys Leu Val Glu Ile Asn Asn Gln Pro Arg
                405                 410                 415

Ile Lys Leu Ser Glu Asp Val Thr Lys Val Ser Ile Pro Cys Lys Lys
            420                 425                 430

Arg Ser Tyr Arg Leu Tyr Gly Lys Glu Gly Tyr Pro Leu Val Asp Ile
        435                 440                 445

Met Thr Gly Glu Asn Glu Pro Pro Pro Lys Val Gly Glu Arg Leu Leu
    450                 455                 460

Cys Arg His Pro Phe Asn Glu Ser Lys Arg Ala Tyr Val Val Pro Gln
465                 470                 475                 480

Arg Val Glu Glu Leu Leu Lys Cys Tyr Trp Arg Gly Ser Ala Asp Glu
                485                 490                 495

Ala Arg Glu Val Leu Pro Pro Leu Lys Glu Ile Arg Asp Arg Cys Ile
            500                 505                 510

Lys Gln Leu Glu Asn Met Arg Pro Asp His Met Arg Arg Leu Asn Pro
        515                 520                 525

Thr Pro Tyr Lys Val Ser Val Ser Ala Lys Leu Tyr Asp Phe Ile His
    530                 535                 540

Phe Leu Trp Leu Asn Glu Ala Pro Val Gly Glu Leu Gln
545                 550                 555
```

<210> SEQ ID NO 21
<211> LENGTH: 717
<212> TYPE: DNA
<213> ORGANISM: Arabidopsis thaliana

<400> SEQUENCE: 21

```
atggatgtcc cgttaccagt cgagaaatta tcttatggat caaacactga ggacaaaact      60

tgtgtagtgc ttgtggcaac tgggagtttc aatcctccta ctttcatgca tttacgcatg     120

tttgagctgg cgagagatga attacgctca aaaggatttc atgttcttgg aggatatatg     180

tctcctgtta atgatgcata taagaagaag ggccttttat ctgcagaaca tcgtttagag     240

atgtgtaatg tatcatgtca aagctctgac tttgtaatgg ttgatccgtg ggaggcatct     300

caaagcaact accaacgaac tttgacggtt ttatcaaggg tcaagacttt cttaacaaca     360

aatcgacatg tacccgagga atctctcaaa gtcatgctac tatgtggctc ggatttactg     420

ctatctttct gcactcccgg tgtttggatc cctgaacagt taagaactat ttgcaaagat     480

tatggcattg tgtgcatccg tagagaagga caagatgttg aaaatatgat ctctggtgac     540
```

```
gaaatcttaa acgaaaactg tgctaacgtc aaaatcgttg acaatactgt tcctaatcaa    600

atcagttcga gtagattaag gcaatgcatt tcgcgagggt tatcggttaa atacttgact    660

gaagatggag taatagatta tatcagacaa catcaactat acactgagct cacatga       717


<210> SEQ ID NO 22
<211> LENGTH: 238
<212> TYPE: PRT
<213> ORGANISM: Arabidopsis thaliana

<400> SEQUENCE: 22

Met Asp Val Pro Leu Pro Val Glu Lys Leu Ser Tyr Gly Ser Asn Thr
1               5                   10                  15

Glu Asp Lys Thr Cys Val Val Leu Val Ala Thr Gly Ser Phe Asn Pro
            20                  25                  30

Pro Thr Phe Met His Leu Arg Met Phe Glu Leu Ala Arg Asp Glu Leu
        35                  40                  45

Arg Ser Lys Gly Phe His Val Leu Gly Gly Tyr Met Ser Pro Val Asn
    50                  55                  60

Asp Ala Tyr Lys Lys Lys Gly Leu Leu Ser Ala Glu His Arg Leu Glu
65                  70                  75                  80

Met Cys Asn Val Ser Cys Gln Ser Ser Asp Phe Val Met Val Asp Pro
                85                  90                  95

Trp Glu Ala Ser Gln Ser Asn Tyr Gln Arg Thr Leu Thr Val Leu Ser
            100                 105                 110

Arg Val Lys Thr Phe Leu Thr Thr Asn Arg His Val Pro Glu Glu Ser
        115                 120                 125

Leu Lys Val Met Leu Leu Cys Gly Ser Asp Leu Leu Leu Ser Phe Cys
    130                 135                 140

Thr Pro Gly Val Trp Ile Pro Glu Gln Leu Arg Thr Ile Cys Lys Asp
145                 150                 155                 160

Tyr Gly Ile Val Cys Ile Arg Arg Glu Gly Gln Asp Val Glu Asn Met
                165                 170                 175

Ile Ser Gly Asp Glu Ile Leu Asn Glu Asn Cys Ala Asn Val Lys Ile
            180                 185                 190

Val Asp Asn Thr Val Pro Asn Gln Ile Ser Ser Ser Arg Leu Arg Gln
        195                 200                 205

Cys Ile Ser Arg Gly Leu Ser Val Lys Tyr Leu Thr Glu Asp Gly Val
    210                 215                 220

Ile Asp Tyr Ile Arg Gln His Gln Leu Tyr Thr Glu Leu Thr
225                 230                 235


<210> SEQ ID NO 23
<211> LENGTH: 2178
<212> TYPE: DNA
<213> ORGANISM: Arabidopsis thaliana

<400> SEQUENCE: 23

atgaggctgt tgaaggttgc tacgtgtaac ttgaaccaat gggccatgga tttcgagagc     60

aacatgaaga acatcaaggc ttcgatcgct gaggcaaagg ctgctggtgc tgttatcagg    120

cttggacccg agctcgaggt cactggctat ggttgcgagg atcacttctt ggaactcgac    180

actgtcactc atgcgtggga gtgtttgaag gaattgctgc ttggtgattg gacggatgat    240

attttgtgca gcataggaat gcctgtgatt aaaggagcag agcgttataa ctgccaggtt    300

ctctgtatga acagaagaat catcatgatt cgaccgaaaa tgtggctcgc aaacgatgga    360
```

```
aactataggg agctacggtg gttcacagct tggaagcaga gagaagagct agaggaattt    420

cagctcccca ttgaaatttc agaggctttg gagcagaaat cagtcccttt tggttatggt    480

tacatccagt ttatcgacac ggctgttgca gctgaagtct gtgaggaact gtttagtcca    540

cttcctcctc atgccgagct cgcattgaat ggtgttgaag tatttatgaa tgcaagtggg    600

agtcatcacc aacttaggaa actagatatt cgtctgaatg cttttatggg ggctactcat    660

gctcgtggtg gggtgtatat gtacagtaat caacaaggat gcgatggtag ccgcttatac    720

tacgatggat gtgcatgtat tgttgtaaac gggaatgttg ttgctcaagg ctcacaattc    780

tcgttgagag acgttgaggt catcatttca caagtggatc ttgatgcggt tgctagcctt    840

cgtggatcta taagtagctt tcaggaacaa gcaagctgca aggttaaagt atcttcagta    900

gctgtgccct gtagacttac acagtccttc aacctgaaaa tgacactaag cagtccgaag    960

aagatcattt accactctcc acaagaagaa atagcctttg gtcccgcttg ctggatgtgg   1020

gactatttga gaagaagtgg cgcttcagga tttttgcttc ctctttctgg cggagcagac   1080

agctcctccg tggcagctat tgttggctgc atgtgccaac ttgttgttaa agagattgca   1140

aagggagatg agcaagtaaa agctgatgcg aaccgaattg ggaattatgc taatgggcag   1200

tttcctactg atagcaaaga gtttgccaaa cgaatatttt acactgtctt tatgggttct   1260

gaaaacagtt ctgaggagac aaaaaggcgt tcaaagcagc tggcagacga gattggtgct   1320

tggcatcttg atgtttgcat agatggtgtt gtctctgcag ttttatcatt atttcaaaca   1380

gttacaggca agcgaccaag gtataaggtt gatggaggat caaatgctga gaaccttggg   1440

ttgcagaaca ttcaagcccg gatgagaatg gtgttagcat ttatgttagc gtctctcttg   1500

ccttgggttc atagcaaacc aggcttttac cttgttctag gcagctccaa cgttgatgaa   1560

ggacttcgtg gttacctgac aaagtatgat tgcagctcag cagacataaa tcctatagga   1620

agtatcagta aaatggattt gaggttgttc ttaaaatggg ctgcaacgaa tctcggatat   1680

ccatccttgg cagagataga agctgctcca ccaacagctg agcttgagcc cattcgttct   1740

gactattctc agctcgatga agtcgacatg ggaatgacat atgaagagct ttcagtctat   1800

ggaaggatga ggaagatatt ccgttgtgga ccagtatcta tgttcaagaa tctatgttac   1860

aagtggggaa caaagctaag cccagcagaa gtagctgaga aagtgaagta tttcttcaaa   1920

tattattcga tcaatcgaca caaaatgact gtcctcacac cgtcttatca cgctgagagt   1980

tactccccag aggacaacag attcgatctg aggcagtttc tgtacaacag caagtggcca   2040

taccagttta agaagattga cgagattgtt gacagcttaa atggtgactc agttgctttc   2100

ccggaagaag aagcaaactc caacaaagaa attggagttg tagcagcaaa ctccggagac   2160

ccaagtgcgg gtctctga                                                 2178
```

```
<210> SEQ ID NO 24
<211> LENGTH: 725
<212> TYPE: PRT
<213> ORGANISM: Arabidopsis thaliana

<400> SEQUENCE: 24

Met Arg Leu Leu Lys Val Ala Thr Cys Asn Leu Asn Gln Trp Ala Met
1               5                   10                  15

Asp Phe Glu Ser Asn Met Lys Asn Ile Lys Ala Ser Ile Ala Glu Ala
            20                  25                  30

Lys Ala Ala Gly Ala Val Ile Arg Leu Gly Pro Glu Leu Glu Val Thr
        35                  40                  45
```

```
Gly Tyr Gly Cys Glu Asp His Phe Leu Glu Leu Asp Thr Val Thr His
    50                  55                  60

Ala Trp Glu Cys Leu Lys Glu Leu Leu Leu Gly Asp Trp Thr Asp Asp
65                  70                  75                  80

Ile Leu Cys Ser Ile Gly Met Pro Val Ile Lys Gly Ala Glu Arg Tyr
                85                  90                  95

Asn Cys Gln Val Leu Cys Met Asn Arg Arg Ile Ile Met Ile Arg Pro
            100                 105                 110

Lys Met Trp Leu Ala Asn Asp Gly Asn Tyr Arg Glu Leu Arg Trp Phe
        115                 120                 125

Thr Ala Trp Lys Gln Arg Glu Glu Leu Glu Glu Phe Gln Leu Pro Ile
    130                 135                 140

Glu Ile Ser Glu Ala Leu Glu Gln Lys Ser Val Pro Phe Gly Tyr Gly
145                 150                 155                 160

Tyr Ile Gln Phe Ile Asp Thr Ala Val Ala Ala Glu Val Cys Glu Glu
                165                 170                 175

Leu Phe Ser Pro Leu Pro Pro His Ala Glu Leu Ala Leu Asn Gly Val
            180                 185                 190

Glu Val Phe Met Asn Ala Ser Gly Ser His His Gln Leu Arg Lys Leu
        195                 200                 205

Asp Ile Arg Leu Asn Ala Phe Met Gly Ala Thr His Ala Arg Gly Gly
    210                 215                 220

Val Tyr Met Tyr Ser Asn Gln Gln Gly Cys Asp Gly Ser Arg Leu Tyr
225                 230                 235                 240

Tyr Asp Gly Cys Ala Cys Ile Val Val Asn Gly Asn Val Val Ala Gln
                245                 250                 255

Gly Ser Gln Phe Ser Leu Arg Asp Val Glu Val Ile Ile Ser Gln Val
            260                 265                 270

Asp Leu Asp Ala Val Ala Ser Leu Arg Gly Ser Ile Ser Ser Phe Gln
        275                 280                 285

Glu Gln Ala Ser Cys Lys Val Lys Val Ser Ser Val Ala Val Pro Cys
    290                 295                 300

Arg Leu Thr Gln Ser Phe Asn Leu Lys Met Thr Leu Ser Ser Pro Lys
305                 310                 315                 320

Lys Ile Ile Tyr His Ser Pro Gln Glu Glu Ile Ala Phe Gly Pro Ala
                325                 330                 335

Cys Trp Met Trp Asp Tyr Leu Arg Arg Ser Gly Ala Ser Gly Phe Leu
            340                 345                 350

Leu Pro Leu Ser Gly Gly Ala Asp Ser Ser Ser Val Ala Ala Ile Val
        355                 360                 365

Gly Cys Met Cys Gln Leu Val Val Lys Glu Ile Ala Lys Gly Asp Glu
    370                 375                 380

Gln Val Lys Ala Asp Ala Asn Arg Ile Gly Asn Tyr Ala Asn Gly Gln
385                 390                 395                 400

Phe Pro Thr Asp Ser Lys Glu Phe Ala Lys Arg Ile Phe Tyr Thr Val
                405                 410                 415

Phe Met Gly Ser Glu Asn Ser Ser Glu Glu Thr Lys Arg Arg Ser Lys
            420                 425                 430

Gln Leu Ala Asp Glu Ile Gly Ala Trp His Leu Asp Val Cys Ile Asp
        435                 440                 445

Gly Val Val Ser Ala Val Leu Ser Leu Phe Gln Thr Val Thr Gly Lys
    450                 455                 460
```

```
Arg Pro Arg Tyr Lys Val Asp Gly Gly Ser Asn Ala Glu Asn Leu Gly
465                 470                 475                 480

Leu Gln Asn Ile Gln Ala Arg Met Arg Met Val Leu Ala Phe Met Leu
                485                 490                 495

Ala Ser Leu Leu Pro Trp Val His Ser Lys Pro Gly Phe Tyr Leu Val
            500                 505                 510

Leu Gly Ser Ser Asn Val Asp Glu Gly Leu Arg Gly Tyr Leu Thr Lys
        515                 520                 525

Tyr Asp Cys Ser Ser Ala Asp Ile Asn Pro Ile Gly Ser Ile Ser Lys
    530                 535                 540

Met Asp Leu Arg Leu Phe Leu Lys Trp Ala Ala Thr Asn Leu Gly Tyr
545                 550                 555                 560

Pro Ser Leu Ala Glu Ile Glu Ala Ala Pro Pro Thr Ala Glu Leu Glu
                565                 570                 575

Pro Ile Arg Ser Asp Tyr Ser Gln Leu Asp Glu Val Asp Met Gly Met
            580                 585                 590

Thr Tyr Glu Glu Leu Ser Val Tyr Gly Arg Met Arg Lys Ile Phe Arg
        595                 600                 605

Cys Gly Pro Val Ser Met Phe Lys Asn Leu Cys Tyr Lys Trp Gly Thr
    610                 615                 620

Lys Leu Ser Pro Ala Glu Val Ala Glu Lys Val Lys Tyr Phe Phe Lys
625                 630                 635                 640

Tyr Tyr Ser Ile Asn Arg His Lys Met Thr Val Leu Thr Pro Ser Tyr
                645                 650                 655

His Ala Glu Ser Tyr Ser Pro Glu Asp Asn Arg Phe Asp Leu Arg Gln
            660                 665                 670

Phe Leu Tyr Asn Ser Lys Trp Pro Tyr Gln Phe Lys Lys Ile Asp Glu
        675                 680                 685

Ile Val Asp Ser Leu Asn Gly Asp Ser Val Ala Phe Pro Glu Glu Glu
    690                 695                 700

Ala Asn Ser Asn Lys Glu Ile Gly Val Val Ala Ala Asn Ser Gly Asp
705                 710                 715                 720

Pro Ser Ala Gly Leu
                725
```

<210> SEQ ID NO 25
<211> LENGTH: 11811
<212> TYPE: DNA
<213> ORGANISM: Artificial
<220> FEATURE:
<223> OTHER INFORMATION: pTVE467

<400> SEQUENCE: 25

```
agattcgaag ctcggtcccg tgggtgttct gtcgtctcgt tgtacaacga aatccattcc      60

cattccgcgc tcaagatggc ttcccctcgg cagttcatca gggctaaatc aatctagccg     120

acttgtccgg tgaaatgggc tgcactccaa cagaaacaat caaacaaaca tacacagcga     180

cttattcaca cgcgacaaat tacaacggta tatatcctgc cagtactcgg ccgtcgaccg     240

cggtaccccg gaattaagct tgcatgcctg caggcaattg gccgctgtac catgcatgat     300

ctggatttta gtactggatt ttggttttag gaattagaaa ttttattgat agaagtattt     360

tacaaataca aatacatact aagggtttct tatatgctca acacatgagc gaaaccctat     420

aggaacccta attcccttat ctgggaacta ctcacacatt attatggaga aaatagagag     480

agatagattt gtagagagag actggtgatt tcagcgtgtc caagcttgct agcttatta     540
```

-continued

```
tccacgacat tgatgttgtg ggccttcaac tcttccttaa ccttattgat gacttcggga    600
tcatcgctga tgggtcttgt gtaatccagc aggacagtgg tcttataacc tagttctgca    660
gcggaaatgg cggtggcttt gacacaatac tccaaagcta caccgacaat gtaaacctcg    720
tctgtatgat gcttttctaa gtacttgttc atgtcggtct tatggaagtt ccagatgtcg    780
tggaaggcgg agtagtattc acggtcagtc aagaaaccct tgtcgacaat cttaatatgc    840
ttagtgacca cttggtccat tatttggtca accaattgac taccccaggt gtttttcaca    900
cagtgtacgg gccacaaaat accctcttgc gtggaatcat cgcctggcct tggagagtgg    960
taggtgtatg ttgaataggg ttctttatct ttatggttct ttgcgaacga aatatgtctg   1020
gaagggtgcc aatctctggt gaccacaatc ctgtgccagt ctctatcagc atcttgcatc   1080
aaatccgaga taggattgat taattcctca ccttttggaa cagtcaagga acctaaaggt   1140
gaaataaaat cattttgcat atcaacaaca attaaagtct ccatggtttt ggtttaataa   1200
gaagagaaaa gagttctttt gttatggctg aagtaataga gaaatgagct cgagtcctct   1260
ccaaatgaaa tgaacttcct tatatagagg aagggtcttg cgaaggatag tgggattgtg   1320
cgtcatccct tacgtcagtg gagatatcac atcaatccac ttgctttgaa gacgtggttg   1380
gaacgtcttc tttttccacg atgctcctcg tgggtggggg tccatctttg ggaccactgt   1440
cggcagaggc atcttgaacg atagcctttc ctttatcgca atgatggcat ttgtaggtgc   1500
caccttcctt ttctactgtc cttttgatga agtgacagat agctgggcaa tggaatccga   1560
ggaggtttcc cgatattacc ctttgttgaa aagtctcaat agccctttgg tcttctgaga   1620
ctgtatcttt gatattcttg gagtagacga gagtgtcgtg ctccaccatg ttgacgaaga   1680
ttttcttctt gtcattgagt cgtaaaagac tctgtatgaa ctgttcgcca gtcttcacgg   1740
cgagttctgt tagatcctcg atctgaattt ttgactccat gtatggtgca tatggcgcgc   1800
catatgcccg ggccctgtac agcggccgcg ttaacgcgta tactctagag cgatcgcccg   1860
ggccggccat ttaaatgaat tcgagctcgg tacccaaacg cggccgcaag ctataacttc   1920
gtatagcata cattatacga agttattcga ctctagagga tcccaattcc catgcatgga   1980
gtcaaagatt caaatagagg acacttctcg aactcggccg tcgaactcgg ccgtcgagta   2040
catggtcgat aagaaaaggc aatttgtaga tgttaattcc catcttgaaa gaaatatagt   2100
ttaaatattt attgataaaa taacaagtca ggtattatag tccaagcaaa aacataaatt   2160
tattgatgca agtttaaatt cagaaatatt tcaataactg attatatcag ctggtacatt   2220
gccgtagatg aaagactgag tgcgatatta tgtgtaatac ataaattgat gatatagcta   2280
gcttagctca tcgggggatc ctagacgcgt gagatcagat ctcggtgacg ggcaggaccg   2340
gacggggcgg taccggcagg ctgaagtcca gctgccagaa acccacgtca tgccagttcc   2400
cgtgcttgaa gccggccgcc cgcagcatgc cgcggggggc atatccgagc gcctcgtgca   2460
tgcgcacgct cgggtcgttg ggcagcccga tgacagcgac cacgctcttg aagccctgtg   2520
cctccaggga cttcagcagg tgggtgtaga gcgtggagcc cagtcccgtc cgctggtggc   2580
ggggggagac gtacacggtc gactcggccg tccagtcgta ggcgttgcgt gccttccagg   2640
ggcccgcgta ggcgatgccg gcgacctcgc cgtccacctc ggcgacgagc cagggatagc   2700
gctcccgcag acggacgagg tcgtccgtcc actcctgcgg ttcctgcggc tcggtacgga   2760
agttgaccgt gcttgtctcg atgtagtggt tgacgatggt gcagaccgcc ggcatgtccg   2820
cctcggtggc acggcggatg tcggccgggc gtcgttctgg gtccattgtt cttctttact   2880
ctttgtgtga ctgaggtttg gtctagtgct ttggtcatct atatataatg ataacaacaa   2940
```

```
tgagaacaag ctttggagtg atcggagggt ctaggataca tgagattcaa gtggactagg   3000
atctacaccg ttggattttg agtgtggata tgtgtgaggt taattttact tggtaacggc   3060
cacaaaggcc taaggagagg tgttgagacc cttatcggct tgaaccgctg gaataatgcc   3120
acgtggaaga taattccatg aatcttatcg ttatctatga gtgaaattgt gtgatggtgg   3180
agtggtgctt gctcatttta cttgcctggt ggacttggcc ctttccttat ggggaattta   3240
tattttactt actatagagc tttcatacct ttttttacc ttggatttag ttaatatata   3300
atggtatgat tcatgaataa aaatgggaaa tttttgaatt tgtactgcta aatgcataag   3360
attaggtgaa actgtggaat atatattttt ttcatttaaa agcaaaattt gccttttact   3420
agaattataa atatagaaaa atatataaca ttcaaataaa aatgaaaata agaactttca   3480
aaaaacagaa ctatgtttaa tgtgtaaaga ttagtcgcac atcaagtcat ctgttacaat   3540
atgttacaac aagtcataag cccaacaaag ttagcacgtc taaataaact aaagagtcca   3600
cgaaaatatt acaaatcata agcccaacaa agttattgat caaaaaaaaa aaacgcccaa   3660
caaagctaaa caaagtccaa aaaaaacttc tcaagtctcc atcttccttt atgaacattg   3720
aaaactatac acaaaacaag tcagataaat ctctttctgg gcctgtcttc ccaacctcct   3780
acatcacttc cctatcggat tgaatgtttt acttgtacct tttccgttgc aatgatattg   3840
atagtatgtt tgtgaaaact aatagggtta acaatcgaag tcatggaata tggatttggt   3900
ccaagatttt ccgagagctt tctagtagaa agcccatcac cagaaattta ctagtaaaat   3960
aaatcaccaa ttaggtttct tattatgtgc caaattcaat ataattatag aggatatttc   4020
aaatgaaaac gtatgaatgt tattagtaaa tggtcaggta agacattaaa aaaatcctac   4080
gtcagatatt caactttaaa aattcgatca gtgtggaatt gtacaaaaat ttgggatcta   4140
ctatatatat ataatgcttt acaacacttg gattttttt tggaggctgg aatttttaat   4200
ctacatattt gttttggcca tgcaccaact cattgtttag tgtaatactt tgattttgtc   4260
aaatatatgt gttcgtgtat atttgtataa gaatttcttt gaccatatac acacacacat   4320
atatatatat atatatatat tatatatcat gcacttttaa ttgaaaaaat aatatatata   4380
tatatagtgc atttttcta acaaccatat atgttgcgat tgatctgcaa aaatactgct   4440
agagtaatga aaaatataat ctattgctga aattatctca gatgttaaga ttttcttaaa   4500
gtaaattctt tcaaatttta gctaaaagtc ttgtaataac taaagaataa tacacaatct   4560
cgaccacgga aaaaaaacac ataataaatt tgaatttcga ccgcggtacc cggaattggg   4620
ttataattac ctcaggtcga ggaattaatt cggtacgtac ctaataactt cgtatagcat   4680
acattatacg aagttatatg gatctcgagg cattacggca ttacggcact cgcgagggtc   4740
ccaattcgag catggagcca tttacaattg aatatatcct gccgccgctg ccgctttgca   4800
cccggtggag cttgcatgtt ggtttctacg cagaactgag ccggttaggc agataatttc   4860
cattgagaac tgagccatgt gcaccttccc cccaacacgg tgagcgacgg ggcaacggag   4920
tgatccacat gggactttta aacatcatcc gtcggatggc gttgcgagag aagcagtcga   4980
tccgtgagat cagccgacgc accgggcagg cgcgcaacac gatcgcaaag tatttgaacg   5040
caggtacaat cgagccgacg ttcacggtac cggaacgacc aagcaagcta gcttagtaaa   5100
gccctcgcta gattttaatg cggatgttgc gattacttcg ccaactattg cgataacaag   5160
aaaaagccag cctttcatga tatatctccc aatttgtgta gggcttatta tgcacgctta   5220
aaaataataa aagcagactt gacctgatag tttggctgtg agcaattatg tgcttagtgc   5280
```

```
atctaacgct tgagttaagc cgcgccgcga agcggcgtcg gcttgaacga attgttagac   5340
attatttgcc gactaccttg gtgatctcgc ctttcacgta gtggacaaat tcttccaact   5400
gatctgcgcg cgaggccaag cgatcttctt cttgtccaag ataagcctgt ctagcttcaa   5460
gtatgacggg ctgatactgg gccggcaggc gctccattgc ccagtcggca gcgacatcct   5520
tcggcgcgat tttgccggtt actgcgctgt accaaatgcg ggacaacgta agcactacat   5580
ttcgctcatc gccagcccag tcgggcggcg agttccatag cgttaaggtt tcatttagcg   5640
cctcaaatag atcctgttca ggaaccggat caaagagttc ctccgccgct ggacctacca   5700
aggcaacgct atgttctctt gcttttgtca gcaagatagc cagatcaatg tcgatcgtgg   5760
ctggctcgaa gatacctgca agaatgtcat tgcgctgcca ttctccaaat tgcagttcgc   5820
gcttagctgg ataacgccac ggaatgatgt cgtcgtgcac aacaatggtg acttctacag   5880
cgcggagaat ctcgctctct ccaggggaag ccgaagtttc caaaaggtcg ttgatcaaag   5940
ctcgccgcgt tgtttcatca agccttacgg tcaccgtaac cagcaaatca atatcactgt   6000
gtggcttcag gccgccatcc actgcggagc cgtacaaatg tacggccagc aacgtcggtt   6060
cgagatggcg ctcgatgacg ccaactacct ctgatagttg agtcgatact tcggcgatca   6120
ccgcttccct catgatgttt aactttgttt tagggcgact gccctgctgc gtaacatcgt   6180
tgctgctcca taacatcaaa catcgaccca cggcgtaacg cgcttgctgc ttggatgccc   6240
gaggcataga ctgtacccca aaaaaacagt cataacaagc catgaaaacc gccactgcgc   6300
cgttaccacc gctgcgttcg gtcaaggttc tggaccagtt gcgtgagcgc atacgctact   6360
tgcattacag cttacgaacc gaacaggctt atgtccactg ggttcgtgcc ttcatccgtt   6420
tccacggtgt gcgtcacccg gcaaccttgg gcagcagcga agtcgaggca tttctgtcct   6480
ggctggcgaa cgagcgcaag gtttcggtct ccacgcatcg tcaggcattg gcggccttgc   6540
tgttcttcta cggcaagtgc tgtgcacgga tctgccctgg cttcaggaga tcggaagacc   6600
tcggccgtcc gggcgcttgc cggtggtgct gaccccggat gaagtctcta gagctctaga   6660
gggttcgcat cctcggtttt ctggaaggcg agcatcgttt gttcgcccag cttctgtatg   6720
gaacgggcat gcggatcagt gagggtttgc aactgcgggt caaggatctg gatttcgatc   6780
acggcacgat catcgtgcgg gagggcaagg gctccaagga tcgggccttg atgttacccg   6840
agagcttggc acccagcctg cgcgagcagg gatcgatcca acccctccgc tgctatagtg   6900
cagtcggctt ctgacgttca gtgcagccgt cttctgaaaa cgacatgtcg cacaagtcct   6960
aagttacgcg acaggctgcc gccctgccct tttcctggcg ttttcttgtc gcgtgtttta   7020
gtcgcataaa gtagaatact tgcgactaga accggagaca ttacgccatg aacaagagcg   7080
ccgccgctgg cctgctgggc tatgcccgcg tcagcaccga cgaccaggac ttgaccaacc   7140
aacgggccga actgcacgcg gccggctgca ccaagctgtt ttccgagaag atcaccggca   7200
ccaggcgcga ccgcccggag ctggccagga tgcttgacca cctacgccct ggcgacgttg   7260
tgacagtgac caggctagac cgcctggccc gcagcacccg cgacctactg gacattgccg   7320
agcgcatcca ggaggccggc gcgggcctgc gtagcctggc agagccgtgg gccgacacca   7380
ccacgccggc cggccgcatg gtgttgaccg tgttcgccgg cattgccgag ttcgagcgtt   7440
ccctaatcat cgaccgcacc cggagcgggc gcgaggccgc caaggcccga ggcgtgaagt   7500
ttggcccccg ccctaccctc accccggcac agatcgcgca cgcccgcgag ctgatcgacc   7560
aggaaggccg caccgtgaaa gaggcggctg cactgcttgg cgtgcatcgc tcgaccctgt   7620
accgcgcact tgagcgcagc gaggaagtga cgcccaccga ggccaggcgg cgcggtgcct   7680
```

```
tccgtgagga cgcattgacc gaggccgacg ccctggcggc cgccgagaat gaacgccaag   7740
aggaacaagc atgaaaccgc accaggacgg ccaggacgaa ccgtttttca ttaccgaaga   7800
gatcgaggcg gagatgatcg cggccgggta cgtgttcgag ccgcccgcgc acgtctcaac   7860
cgtgcggctg catgaaatcc tggccggttt gtctgatgcc aagctggcgg cctggccggc   7920
cagcttggcc gctgaagaaa ccgagcgccg ccgtctaaaa aggtgatgtg tatttgagta   7980
aaacagcttg cgtcatgcgg tcgctgcgta tatgatgcga tgagtaaata aacaaatacg   8040
caaggggaac gcatgaaggt tatcgctgta cttaaccaga aaggcgggtc aggcaagacg   8100
accatcgcaa cccatctagc ccgcgccctg caactcgccg ggccgatgt tctgttagtc   8160
gattccgatc cccagggcag tgcccgcgat tgggcggccg tgcgggaaga tcaaccgcta   8220
accgttgtcg gcatcgaccg cccgacgatt gaccgcgacg tgaaggccat cggccggcgc   8280
gacttcgtag tgatcgacgg agcgccccag gcggcggact tggctgtgtc cgcgatcaag   8340
gcagccgact tcgtgctgat tccggtgcag ccaagccctt acgacatatg ggccaccgcc   8400
gacctggtgg agctggttaa gcagcgcatt gaggtcacgg atggaaggct acaagcggcc   8460
tttgtcgtgt cgcgggcgat caaaggcacg cgcatcggcg gtgaggttgc cgaggcgctg   8520
gccgggtacg agctgcccat tcttgagtcc cgtatcacgc agcgcgtgag ctacccaggc   8580
actgccgccg ccggcacaac cgttcttgaa tcagaacccg agggcgacgc tgcccgcgag   8640
gtccaggcgc tggccgctga aattaaatca aaactcattt gagttaatga ggtaaagaga   8700
aaatgagcaa aagcacaaac acgctaagtg ccggccgtcc gagcgcacgc agcagcaagg   8760
ctgcaacgtt ggccagcctg gcagacacgc cagccatgaa gcgggtcaac tttcagttgc   8820
cggcggagga tcacaccaag ctgaagatgt acgcggtacg ccaaggcaag accattaccg   8880
agctgctatc tgaatacatc gcgcagctac cagagtaaat gagcaaatga ataaatgagt   8940
agatgaattt tagcggctaa aggaggcggc atggaaaatc aagaacaacc aggcaccgac   9000
gccgtggaat gccccatgtg tggaggaacg ggcggttggc caggcgtaag cggctgggtt   9060
gtctgccggc cctgcaatgg cactggaacc cccaagcccg aggaatcggc gtgacggtcg   9120
caaaccatcc ggcccggtac aaatcggcgc ggcgctgggt gatgacctgg tggagaagtt   9180
gaaggccgcg caggccgccc agcggcaacg catcgaggca gaagcacgcc ccggtgaatc   9240
gtggcaagcg gccgctgatc gaatccgcaa agaatcccgg caaccgccgg cagccggtgc   9300
gccgtcgatt aggaagccgc ccaagggcga cgagcaacca gattttttcg ttccgatgct   9360
ctatgacgtg ggcacccgcg atagtcgcag catcatggac gtggccgttt tccgtctgtc   9420
gaagcgtgac cgacgagctg gcgaggtgat ccgctacgag cttccagacg ggcacgtaga   9480
ggtttccgca gggccggccg gcatggccag tgtgtgggat tacgacctgg tactgatggc   9540
ggtttcccat ctaaccgaat ccatgaaccg ataccgggaa gggaagggag acaagcccgg   9600
ccgcgtgttc cgtccacacg ttgcggacgt actcaagttc tgccggcgag ccgatggcgg   9660
aaagcagaaa gacgacctgg tagaaacctg cattcggtta aacaccacgc acgttgccat   9720
gcagcgtacg aagaaggcca agaacggccg cctggtgacg gtatccgagg gtgaagcctt   9780
gattagccgc tacaagatcg taaagagcga aaccgggcgg ccggagtaca tcgagatcga   9840
gctagctgat tggatgtacc gcgagatcac agaaggcaag aacccggacg tgctgacggt   9900
tcaccccgat actttttga tcgatcccgg catcggccgt tttctctacc gcctggcacg   9960
ccgcgccgca ggcaaggcag aagccagatg gttgttcaag acgatctacg aacgcagtgg   10020
```

```
cagcgccgga gagttcaaga agttctgttt caccgtgcgc aagctgatcg ggtcaaatga  10080
cctgccggag tacgatttga aggaggaggc ggggcaggct ggcccgatcc tagtcatgcg  10140
ctaccgcaac ctgatcgagg gcgaagcatc cgccggttcc taatgtacgg agcagatgct  10200
agggcaaatt gccctagcag gggaaaaagg tcgaaaaggt ctctttcctg tggatagcac  10260
gtacattggg aacccaaagc cgtacattgg gaaccggaac ccgtacattg ggaacccaaa  10320
gccgtacatt gggaaccggt cacacatgta agtgactgat ataaaagaga aaaaaggcga  10380
tttttccgcc taaaactctt taaaacttat taaaactctt aaaacccgcc tggcctgtgc  10440
ataactgtct ggccagcgca cagccgaaga gctgcaaaaa gcgcctaccc ttcggtcgct  10500
gcgctcccta cgccccgccg cttcgcgtcg gcctatcgcg gccgctggcc gctcaaaaat  10560
ggctggccta cggccaggca atctaccagg gcgcggacaa gccgcgccgt cgccactcga  10620
ccgccggcgc ccacatcaag gcaccctgcc tcgcgcgttt cggtgatgac ggtgaaaacc  10680
tctgacacat gcagctcccg gagacggtca cagcttgtct gtaagcggat gccgggagca  10740
gacaagcccg tcagggcgcg tcagcgggtg ttggcgggtg tcggggcgca gccatgaccc  10800
agtcacgtag cgatagcgga gtgtatactg gcttaactat gcggcatcag agcagattgt  10860
actgagagtg caccatatgc ggtgtgaaat accgcacaga tgcgtaagga gaaaataccg  10920
catcaggcgc tcttccgctt cctcgctcac tgactcgctg cgctcggtcg ttcggctgcg  10980
gcgagcggta tcagctcact caaaggcggt aatacggtta tccacagaat caggggataa  11040
cgcaggaaag aacatgtgag caaaaggcca gcaaaaggcc aggaaccgta aaaaggccgc  11100
gttgctggcg tttttccata ggctccgccc ccctgacgag catcacaaaa atcgacgctc  11160
aagtcagagg tggcgaaacc cgacaggact ataaagatac caggcgtttc cccctggaag  11220
ctccctcgtg cgctctcctg ttccgaccct gccgcttacc ggatacctgt ccgcctttct  11280
cccttcggga agcgtggcgc tttctcatag ctcacgctgt aggtatctca gttcggtgta  11340
ggtcgttcgc tccaagctgg gctgtgtgca cgaacccccc gttcagcccg accgctgcgc  11400
cttatccggt aactatcgtc ttgagtccaa cccggtaaga cacgacttat cgccactggc  11460
agcagccact ggtaacagga ttagcagagc gaggtatgta ggcggtgcta cagagttctt  11520
gaagtggtgg cctaactacg gctacactag aaggacagta tttggtatct gcgctctgct  11580
gaagccagtt accttcggaa aaagagttgg tagctcttga tccggcaaac aaaccaccgc  11640
tggtagcggt ggtttttttg tttgcaagca gcagattacg cgcagaaaaa aaggatctca  11700
agaagatccg gaaaacgcaa gcgcaaagag aaagcaggta gcttgcagtg ggcttacatg  11760
gcgatagcta gactgggcgg ttttatggac agcaagcgaa ccggaattgc c           11811
```

<210> SEQ ID NO 26
<211> LENGTH: 11829
<212> TYPE: DNA
<213> ORGANISM: Artificial
<220> FEATURE:
<223> OTHER INFORMATION: pTVE468

<400> SEQUENCE: 26

```
agattcgaag ctcggtcccg tgggtgttct gtcgtctcgt tgtacaacga aatccattcc     60
cattccgcgc tcaagatggc ttcccctcgg cagttcatca gggctaaatc aatctagccg    120
acttgtccgg tgaaatgggc tgcactccaa cagaaacaat caaacaaaca tacacagcga    180
cttattcaca cgcgacaaat tacaacggta tatatcctgc cagtactcgg ccgtcgaccg    240
cggtaccccg gaattaagct tgcatgcctg caggcaattg gccgctgtac catgcatgat    300
```

```
ctggatttta gtactggatt ttggttttag gaattagaaa ttttattgat agaagtattt    360
tacaaataca aatacatact aagggtttct tatatgctca acacatgagc gaaaccctat    420
aggaacccta attcccttat ctgggaacta ctcacacatt attatggaga aaatagagag    480
agatagattt gtagagagag actggtgatt tcagcgtgtc caagcttgct agcttattta    540
tccacgacat tgatgttgtg ggccttcaac tcttccttaa ccttattgat gacttcggga    600
tcatcgctga tgggtcttgt gtaatccagc aggacagtgg tcttataacc tagttctgca    660
gcggaaatgg cggtggcttt gacacaatac tccaaagcta caccgacaat gtaaacctcg    720
tctgtatgat gcttttctaa gtacttgttc atgtcggtct tatggaagtt ccagatgtcg    780
tggaaggcgg agtagtattc acggtcagtc aagaaaccct tgtcgacaat cttaatatgc    840
ttagtgacca cttggtccat tatttggtca accaattgac taccccaggt gtttttcaca    900
cagtgtacgg gccacaaaat accctcttgc gtggaatcat cgcctggcct tggagagtgg    960
taggtgtatg ttgaataggg ttctttatct ttatggttct ttgcgaacga aatatgtctg   1020
gaagggtgcc aatctctggt gaccacaatc ctgtgccagt ctctatcagc atcttgcatc   1080
aaatccgaga taggattgat taattcctca ccttttggaa cagtcaagga acctaaaggt   1140
gaaataaaat cattttgcat atcaacaacc ttgcgcttct tcttgggaat taaagtctcc   1200
atggttttgg tttaataaga agagaaaaga gttcttttgt tatggctgaa gtaatagaga   1260
aatgagctcg agtcctctcc aaatgaaatg aacttcctta tatagaggaa gggtcttgcg   1320
aaggatagtg ggattgtgcg tcatccctta cgtcagtgga gatatcacat caatccactt   1380
gctttgaaga cgtggttgga acgtcttctt tttccacgat gctcctcgtg ggtgggggtc   1440
catctttggg accactgtcg gcagaggcat cttgaacgat agcctttcct ttatcgcaat   1500
gatggcattt gtaggtgcca ccttcctttt ctactgtcct tttgatgaag tgacagatag   1560
ctgggcaatg gaatccgagg aggtttcccg atattaccct ttgttgaaaa gtctcaatag   1620
ccctttggtc ttctgagact gtatctttga tattcttgga gtagacgaga gtgtcgtgct   1680
ccaccatgtt gacgaagatt ttcttcttgt cattgagtcg taaaagactc tgtatgaact   1740
gttcgccagt cttcacggcg agttctgtta gatcctcgat ctgaattttt gactccatgt   1800
atggtgcata tggcgcgcca tatgcccggg ccctgtacag cggccgcgtt aacgcgtata   1860
ctctagagcg atcgcccggg ccggccattt aaatgaattc gagctcggta cccaaacgcg   1920
gccgcaagct ataacttcgt atagcataca ttatacgaag ttattcgact ctagaggatc   1980
ccaattccca tgcatggagt caaagattca aatagaggac acttctcgaa ctcggccgtc   2040
gaactcggcc gtcgagtaca tggtcgataa gaaaaggcaa tttgtagatg ttaattccca   2100
tcttgaaaga aatatagttt aaatatttat tgataaaata acaagtcagg tattatagtc   2160
caagcaaaaa cataaattta ttgatgcaag tttaaattca gaaatatttc aataactgat   2220
tatatcagct ggtacattgc cgtagatgaa agactgagtg cgatattatg tgtaatacat   2280
aaattgatga tatagctagc ttagctcatc gggggatcct agacgcgtga gatcagatct   2340
cggtgacggg caggaccgga cggggcggta ccggcaggct gaagtccagc tgccagaaac   2400
ccacgtcatg ccagttcccg tgcttgaagc cggccgcccg cagcatgccg cggggggcat   2460
atccgagcgc ctcgtgcatg cgcacgctcg ggtcgttggg cagcccgatg acagcgacca   2520
cgctcttgaa gccctgtgcc tccagggact tcagcaggtg ggtgtagagc gtggagccca   2580
gtcccgtccg ctggtggcgg ggggagacgt acacggtcga ctcggccgtc cagtcgtagg   2640
```

```
cgttgcgtgc cttccagggg cccgcgtagg cgatgccggc gacctcgccg tccacctcgg   2700
cgacgagcca gggatagcgc tcccgcagac ggacgaggtc gtccgtccac tcctgcggtt   2760
cctgcggctc ggtacggaag ttgaccgtgc ttgtctcgat gtagtggttg acgatggtgc   2820
agaccgccgg catgtccgcc tcggtggcac ggcggatgtc ggccgggcgt cgttctgggt   2880
ccattgttct tctttactct ttgtgtgact gaggtttggt ctagtgcttt ggtcatctat   2940
atataatgat aacaacaatg agaacaagct ttggagtgat cggagggtct aggatacatg   3000
agattcaagt ggactaggat ctacaccgtt ggattttgag tgtggatatg tgtgaggtta   3060
attttacttg gtaacggcca caaaggccta aggagaggtg ttgagaccct tatcggcttg   3120
aaccgctgga ataatgccac gtggaagata attccatgaa tcttatcgtt atctatgagt   3180
gaaattgtgt gatggtggag tggtgcttgc tcattttact tgcctggtgg acttggccct   3240
ttccttatgg ggaatttata ttttacttac tatagagctt tcataccttt tttttacctt   3300
ggatttagtt aatatataat ggtatgattc atgaataaaa atgggaaatt tttgaatttg   3360
tactgctaaa tgcataagat taggtgaaac tgtggaatat atattttttt catttaaaag   3420
caaaatttgc cttttactag aattataaat atagaaaaat atataacatt caaataaaaa   3480
tgaaaataag aactttcaaa aaacagaact atgtttaatg tgtaaagatt agtcgcacat   3540
caagtcatct gttacaatat gttacaacaa gtcataagcc caacaaagtt agcacgtcta   3600
aataaactaa agagtccacg aaaatattac aaatcataag cccaacaaag ttattgatca   3660
aaaaaaaaaa acgcccaaca aagctaaaca aagtccaaaa aaaacttctc aagtctccat   3720
cttcctttat gaacattgaa aactatacac aaaacaagtc agataaatct ctttctgggc   3780
ctgtcttccc aacctcctac atcacttccc tatcggattg aatgttttac ttgtaccttt   3840
tccgttgcaa tgatattgat agtatgtttg tgaaaactaa tagggttaac aatcgaagtc   3900
atggaatatg gatttggtcc aagattttcc gagagctttc tagtagaaag cccatcacca   3960
gaaatttact agtaaaataa atcaccaatt aggtttctta ttatgtgcca aattcaatat   4020
aattatagag gatatttcaa atgaaaacgt atgaatgtta ttagtaaatg gtcaggtaag   4080
acattaaaaa aatcctacgt cagatattca actttaaaaa ttcgatcagt gtggaattgt   4140
acaaaaattt gggatctact atatatatat aatgctttac aacacttgga tttttttttg   4200
gaggctggaa tttttaatct acatatttgt tttggccatg caccaactca ttgtttagtg   4260
taatactttg attttgtcaa atatatgtgt tcgtgtatat ttgtataaga atttctttga   4320
ccatatacac acacacatat atatatatat atatatatta tatatcatgc acttttaatt   4380
gaaaaaataa tatatatata tatagtgcat tttttctaac aaccatatat gttgcgattg   4440
atctgcaaaa atactgctag agtaatgaaa aatataatct attgctgaaa ttatctcaga   4500
tgttaagatt ttcttaaagt aaattctttc aaattttagc taaaagtctt gtaataacta   4560
aagaataata cacaatctcg accacggaaa aaaaacacat aataaatttg aatttcgacc   4620
gcggtacccg gaattgggtt ataattacct caggtcgagg aattaattcg gtacgtacct   4680
aataacttcg tatagcatac attatacgaa gttatatgga tctcgaggca ttacggcatt   4740
acggcactcg cgagggtccc aattcgagca tggagccatt tacaattgaa tatatcctgc   4800
cgccgctgcc gctttgcacc cggtggagct tgcatgttgg tttctacgca gaactgagcc   4860
ggttaggcag ataatttcca ttgagaactg agccatgtgc accttccccc caacacggtg   4920
agcgacgggg caacggagtg atccacatgg gacttttaaa catcatccgt cggatggcgt   4980
tgcgagagaa gcagtcgatc cgtgagatca gccgacgcac cgggcaggcg cgcaacacga   5040
```

```
tcgcaaagta tttgaacgca ggtacaatcg agccgacgtt cacggtaccg gaacgaccaa   5100
gcaagctagc ttagtaaagc cctcgctaga ttttaatgcg gatgttgcga ttacttcgcc   5160
aactattgcg ataacaagaa aaagccagcc tttcatgata tatctcccaa tttgtgtagg   5220
gcttattatg cacgcttaaa aataataaaa gcagacttga cctgatagtt tggctgtgag   5280
caattatgtg cttagtgcat ctaacgcttg agttaagccg cgccgcgaag cggcgtcggc   5340
ttgaacgaat tgttagacat tatttgccga ctaccttggt gatctcgcct ttcacgtagt   5400
ggacaaattc ttccaactga tctgcgcgcg aggccaagcg atcttcttct tgtccaagat   5460
aagcctgtct agcttcaagt atgacgggct gatactgggc cggcaggcgc tccattgccc   5520
agtcggcagc gacatccttc ggcgcgattt tgccggttac tgcgctgtac caaatgcggg   5580
acaacgtaag cactacattt cgctcatcgc cagcccagtc gggcggcgag ttccatagcg   5640
ttaaggtttc atttagcgcc tcaaatagat cctgttcagg aaccggatca aagagttcct   5700
ccgccgctgg acctaccaag gcaacgctat gttctcttgc ttttgtcagc aagatagcca   5760
gatcaatgtc gatcgtggct ggctcgaaga tacctgcaag aatgtcattg cgctgccatt   5820
ctccaaattg cagttcgcgc ttagctggat aacgccacgg aatgatgtcg tcgtgcacaa   5880
caatggtgac ttctacagcg cggagaatct cgctctctcc aggggaagcc gaagtttcca   5940
aaaggtcgtt gatcaaagct cgccgcgttg tttcatcaag ccttacggtc accgtaacca   6000
gcaaatcaat atcactgtgt ggcttcaggc cgccatccac tgcggagccg tacaaatgta   6060
cggccagcaa cgtcggttcg agatggcgct cgatgacgcc aactacctct gatagttgag   6120
tcgatacttc ggcgatcacc gcttccctca tgatgtttaa ctttgtttta gggcgactgc   6180
cctgctgcgt aacatcgttg ctgctccata acatcaaaca tcgacccacg gcgtaacgcg   6240
cttgctgctt ggatgcccga ggcatagact gtaccccaaa aaaacagtca taacaagcca   6300
tgaaaaccgc cactgcgccg ttaccaccgc tgcgttcggt caaggttctg gaccagttgc   6360
gtgagcgcat acgctacttg cattacagct tacgaaccga acaggcttat gtccactggg   6420
ttcgtgcctt catccgtttc cacggtgtgc gtcacccggc aaccttgggc agcagcgaag   6480
tcgaggcatt tctgtcctgg ctggcgaacg agcgcaaggt ttcggtctcc acgcatcgtc   6540
aggcattggc ggccttgctg ttcttctacg gcaagtgctg tgcacggatc tgccctggct   6600
tcaggagatc ggaagacctc ggccgtccgg gcgcttgccg gtggtgctga ccccggatga   6660
agtctctaga gctctagagg gttcgcatcc tcggttttct ggaaggcgag catcgtttgt   6720
tcgcccagct tctgtatgga acgggcatgc ggatcagtga gggtttgcaa ctgcgggtca   6780
aggatctgga tttcgatcac ggcacgatca tcgtgcggga gggcaagggc tccaaggatc   6840
gggccttgat gttacccgag agcttggcac ccagcctgcg cgagcaggga tcgatccaac   6900
ccctccgctg ctatagtgca gtcggcttct gacgttcagt gcagccgtct tctgaaaacg   6960
acatgtcgca caagtcctaa gttacgcgac aggctgccgc cctgcccttt tcctggcgtt   7020
ttcttgtcgc gtgttttagt cgcataaagt agaatacttg cgactagaac cggagacatt   7080
acgccatgaa caagagcgcc gccgctggcc tgctgggcta tgcccgcgtc agcaccgacg   7140
accaggactt gaccaaccaa cgggccgaac tgcacgcggc cggctgcacc aagctgtttt   7200
ccgagaagat caccggcacc aggcgcgacc gcccggagct ggccaggatg cttgaccacc   7260
tacgccctgg cgacgttgtg acagtgacca ggctagaccg cctggcccgc agcacccgcg   7320
acctactgga cattgccgag cgcatccagg aggccggcgc gggcctgcgt agcctggcag   7380
```

```
agccgtgggc cgacaccacc acgccggccg gccgcatggt gttgaccgtg ttcgccggca   7440
ttgccgagtt cgagcgttcc ctaatcatcg accgcacccg gagcgggcgc gaggccgcca   7500
aggcccgagg cgtgaagttt ggcccccgcc ctaccctcac cccggcacag atcgcgcacg   7560
cccgcgagct gatcgaccag gaaggccgca ccgtgaaaga ggcggctgca ctgcttggcg   7620
tgcatcgctc gaccctgtac cgcgcacttg agcgcagcga ggaagtgacg cccaccgagg   7680
ccaggcggcg cggtgccttc cgtgaggacg cattgaccga ggccgacgcc ctggcggccg   7740
ccgagaatga acgccaagag gaacaagcat gaaaccgcac caggacggcc aggacgaacc   7800
gtttttcatt accgaagaga tcgaggcgga gatgatcgcg gccgggtacg tgttcgagcc   7860
gcccgcgcac gtctcaaccg tgcggctgca tgaaatcctg gccggtttgt ctgatgccaa   7920
gctggcggcc tggccggcca gcttggccgc tgaagaaacc gagcgccgcc gtctaaaaag   7980
gtgatgtgta tttgagtaaa acagcttgcg tcatgcggtc gctgcgtata tgatgcgatg   8040
agtaaataaa caaatacgca aggggaacgc atgaaggtta tcgctgtact taaccagaaa   8100
ggcgggtcag gcaagacgac catcgcaacc catctagccc gcgccctgca actcgccggg   8160
gccgatgttc tgttagtcga ttccgatccc cagggcagtg cccgcgattg ggcggccgtg   8220
cgggaagatc aaccgctaac cgttgtcggc atcgaccgcc cgacgattga ccgcgacgtg   8280
aaggccatcg gccggcgcga cttcgtagtg atcgacggag cgccccaggc ggcggacttg   8340
gctgtgtccg cgatcaaggc agccgacttc gtgctgattc cggtgcagcc aagcccttac   8400
gacatatggg ccaccgccga cctggtggag ctggttaagc agcgcattga ggtcacggat   8460
ggaaggctac aagcggcctt tgtcgtgtcg cgggcgatca aaggcacgcg catcggcggt   8520
gaggttgccg aggcgctggc cgggtacgag ctgcccattc ttgagtcccg tatcacgcag   8580
cgcgtgagct acccaggcac tgccgccgcc ggcacaaccg ttcttgaatc agaacccgag   8640
ggcgacgctg cccgcgaggt ccaggcgctg gccgctgaaa ttaaatcaaa actcatttga   8700
gttaatgagg taaagagaaa atgagcaaaa gcacaaacac gctaagtgcc ggccgtccga   8760
gcgcacgcag cagcaaggct gcaacgttgg ccagcctggc agacacgcca gccatgaagc   8820
gggtcaactt tcagttgccg gcggaggatc acaccaagct gaagatgtac gcggtacgcc   8880
aaggcaagac cattaccgag ctgctatctg aatacatcgc gcagctacca gagtaaatga   8940
gcaaatgaat aaatgagtag atgaatttta gcggctaaag gaggcggcat ggaaaatcaa   9000
gaacaaccag gcaccgacgc cgtggaatgc cccatgtgtg gaggaacggg cggttggcca   9060
ggcgtaagcg gctgggttgt ctgccggccc tgcaatggca ctggaacccc caagcccgag   9120
gaatcggcgt gacggtcgca aaccatccgg cccggtacaa atcggcgcgg cgctgggtga   9180
tgacctggtg gagaagttga aggccgcgca ggccgcccag cggcaacgca tcgaggcaga   9240
agcacgcccc ggtgaatcgt ggcaagcggc cgctgatcga atccgcaaag aatcccggca   9300
accgccggca gccggtgcgc cgtcgattag gaagccgccc aagggcgacg agcaaccaga   9360
ttttttcgtt ccgatgctct atgacgtggg cacccgcgat agtcgcagca tcatggacgt   9420
ggccgttttc cgtctgtcga agcgtgaccg acgagctggc gaggtgatcc gctacgagct   9480
tccagacggg cacgtagagg tttccgcagg gccggccggc atggccagtg tgtgggatta   9540
cgacctggta ctgatggcgg tttcccatct aaccgaatcc atgaaccgat accgggaagg   9600
gaagggagac aagcccggcc gcgtgttccg tccacacgtt gcggacgtac tcaagttctg   9660
ccggcgagcc gatggcggaa agcagaaaga cgacctggta gaaacctgca ttcggttaaa   9720
caccacgcac gttgccatgc agcgtacgaa gaaggccaag aacggccgcc tggtgacggt   9780
```

```
atccgagggt gaagccttga ttagccgcta caagatcgta aagagcgaaa ccgggcggcc    9840
ggagtacatc gagatcgagc tagctgattg gatgtaccgc gagatcacag aaggcaagaa    9900
cccggacgtg ctgacggttc accccgatta ctttttgatc gatcccggca tcggccgttt    9960
tctctaccgc ctggcacgcc gcgccgcagg caaggcagaa gccagatggt tgttcaagac   10020
gatctacgaa cgcagtggca gcgccggaga gttcaagaag ttctgtttca ccgtgcgcaa   10080
gctgatcggg tcaaatgacc tgccggagta cgatttgaag gaggaggcgg ggcaggctgg   10140
cccgatccta gtcatgcgct accgcaacct gatcgagggc gaagcatccg ccggttccta   10200
atgtacggag cagatgctag ggcaaattgc cctagcaggg gaaaaaggtc gaaaaggtct   10260
ctttcctgtg gatagcacgt acattgggaa cccaaagccg tacattggga accggaaccc   10320
gtacattggg aacccaaagc cgtacattgg gaaccggtca cacatgtaag tgactgatat   10380
aaaagagaaa aaaggcgatt tttccgccta aaactcttta aaacttatta aaactcttaa   10440
aacccgcctg gcctgtgcat aactgtctgg ccagcgcaca gccgaagagc tgcaaaaagc   10500
gcctaccctt cggtcgctgc gctccctacg ccccgccgct tcgcgtcggc ctatcgcggc   10560
cgctggccgc tcaaaaatgg ctggcctacg gccaggcaat ctaccagggc gcggacaagc   10620
cgcgccgtcg ccactcgacc gccggcgccc acatcaaggc accctgcctc gcgcgtttcg   10680
gtgatgacgg tgaaaacctc tgacacatgc agctcccgga gacggtcaca gcttgtctgt   10740
aagcggatgc cgggagcaga caagcccgtc agggcgcgtc agcgggtgtt ggcgggtgtc   10800
ggggcgcagc catgacccag tcacgtagcg atagcggagt gtatactggc ttaactatgc   10860
ggcatcagag cagattgtac tgagagtgca ccatatgcgg tgtgaaatac cgcacagatg   10920
cgtaaggaga aaataccgca tcaggcgctc ttccgcttcc tcgctcactg actcgctgcg   10980
ctcggtcgtt cggctgcggc gagcggtatc agctcactca aaggcggtaa tacggttatc   11040
cacagaatca ggggataacg caggaaagaa catgtgagca aaaggccagc aaaaggccag   11100
gaaccgtaaa aaggccgcgt tgctggcgtt tttccatagg ctccgccccc ctgacgagca   11160
tcacaaaaat cgacgctcaa gtcagaggtg gcgaaacccg acaggactat aaagatacca   11220
ggcgtttccc cctggaagct ccctcgtgcg ctctcctgtt ccgaccctgc cgcttaccgg   11280
atacctgtcc gcctttctcc cttcgggaag cgtggcgctt tctcatagct cacgctgtag   11340
gtatctcagt tcggtgtagg tcgttcgctc caagctgggc tgtgtgcacg aaccccccgt   11400
tcagcccgac cgctgcgcct tatccggtaa ctatcgtctt gagtccaacc cggtaagaca   11460
cgacttatcg ccactggcag cagccactgg taacaggatt agcagagcga ggtatgtagg   11520
cggtgctaca gagttcttga agtggtggcc taactacggc tacactagaa ggacagtatt   11580
tggtatctgc gctctgctga agccagttac cttcggaaaa agagttggta gctcttgatc   11640
cggcaaacaa accaccgctg gtagcggtgg tttttttgtt tgcaagcagc agattacgcg   11700
cagaaaaaaa ggatctcaag aagatccgga aaacgcaagc gcaaagagaa agcaggtagc   11760
ttgcagtggg cttacatggc gatagctaga ctgggcggtt ttatggacag caagcgaacc   11820
ggaattgcc                                                           11829
```

<210> SEQ ID NO 27
<211> LENGTH: 12393
<212> TYPE: DNA
<213> ORGANISM: Artificial
<220> FEATURE:
<223> OTHER INFORMATION: pTVE469

<400> SEQUENCE: 27

```
agattcgaag ctcggtcccg tgggtgttct gtcgtctcgt tgtacaacga aatccattcc     60
cattccgcgc tcaagatggc ttcccctcgg cagttcatca gggctaaatc aatctagccg    120
acttgtccgg tgaaatgggc tgcactccaa cagaaacaat caaacaaaca tacacagcga    180
cttattcaca cgcgacaaat tacaacggta tatatcctgc cagtactcgg ccgtcgaccg    240
cggtaccccg gaattaagct tgcatgcctg caggcaattg gccgctgtac catgcatgat    300
ctggatttta gtactggatt ttggttttag gaattagaaa ttttattgat agaagtattt    360
tacaaataca aatacatact aagggtttct tatatgctca acacatgagc gaaaccctat    420
aggaacccta attcccttat ctgggaacta ctcacacatt attatggaga aaatagagag    480
agatagattt gtagagagag actggtgatt tcagcgtgtc caagcttgct agcttatgct    540
atagggaggc ataattgatg cttggcttga ataacagcat cacgatcacc agtatttttc    600
atgatatcgt cactaatctt cactgcttta gttccttcag cggaaaaaag cttaataaca    660
atattcatag gtttgctcac ttcactggga ttggaaactt tttggaagtc gctggtaaga    720
tttgtgccga tgccaaatgc agacttaatg ccacatttct cgcagtattt gtacagttcg    780
atacatctgt caacatttaa agcatcgcta tgaacaatta cttttgtgga aggatcgaca    840
cctattgatt tatagtgctt tacgactttt tcaatgtatt cctcagcaca accgctatct    900
tgacgaacac catggaaaac attggctaaa tcgtcggcag aattggctgt aaaagatttg    960
agaaacacat cagtagagaa tgtatccgtt aaggctatta aaagactagt accaaaagtt   1020
tggacccact ttaaggaagc aatacgattt gcttgtttat aattttgagt aatagctgca   1080
atgcccatat accactcgtg agcaaccgta ccagagacat ttagattata tttggcggcg   1140
aagtaaacat tagatgtacc aaggaaactt ccagggccct taaaatcctc ttgtgctttc   1200
atgagacctt ggagaacaat ttcctgggtg tgaggatcac gacgacgacg agtgccaaag   1260
tcagtaaagg cacatccggc tcggatgaga cgcttaccct tctcgtaagc tttttcaaac   1320
tgaccctcag gtgaccagtc cttatcgaca aatttaaaat aagattctga gacgagagca   1380
agcagtggaa tttcataaaa aatggtattc ttccagaggc cgtgaataaa gattgagaga   1440
tccttagttt cagaatcata attaagggaa attgaatttt caggatcaaa ttcgaactca   1500
tgcatgaatt cataaaatga ttcctttaaa taaggacagt tcttgcgaag ccattgctct   1560
tcttcaggaa gtaaatgtaa attccgtaag cctcttattt gttcccgtaa ccagttataa   1620
gcctcctgat ttaatgccat ttttggggac cggtttgtat acttatatga tacttgagca   1680
tccggataat gctctaaaac ggcttgaagc atggtgagtt tgtaaagatc cgtatcgagg   1740
atagagacaa cagccggttc acccatggtt ttggtttaat aagaagagaa aagagttctt   1800
ttgttatggc tgaagtaata gagaaatgag ctcgagtcct ctccaaatga aatgaacttc   1860
cttatataga ggaagggtct tgcgaaggat agtgggattg tgcgtcatcc cttacgtcag   1920
tggagatatc acatcaatcc acttgctttg aagacgtggt tggaacgtct tctttttcca   1980
cgatgctcct cgtgggtggg ggtccatctt tgggaccact gtcggcagag gcatcttgaa   2040
cgatagcctt tcctttatcg caatgatggc atttgtaggt gccaccttcc ttttctactg   2100
tccttttgat gaagtgacag atagctgggc aatggaatcc gaggaggttt cccgatatta   2160
ccctttgttg aaaagtctca atagcccttt ggtcttctga gactgtatct ttgatattct   2220
tggagtagac gagagtgtcg tgctccacca tgttgacgaa gattttcttc ttgtcattga   2280
gtcgtaaaag actctgtatg aactgttcgc cagtcttcac ggcgagttct gttagatcct   2340
```

```
cgatctgaat ttttgactcc atgtatggtg catatggcgc gccatatgcc cgggccctgt   2400
acagcggccg cgttaacgcg tatactctag agcgatcgcc cgggccggcc atttaaatga   2460
attcgagctc ggtacccaaa cgcggccgca agctataact tcgtatagca tacattatac   2520
gaagttattc gactctagag gatcccaatt cccatgcatg gagtcaaaga ttcaaataga   2580
ggacacttct cgaactcggc cgtcgaactc ggccgtcgag tacatggtcg ataagaaaag   2640
gcaatttgta gatgttaatt cccatcttga aagaaatata gtttaaatat ttattgataa   2700
aataacaagt caggtattat agtccaagca aaaacataaa tttattgatg caagtttaaa   2760
ttcagaaata tttcaataac tgattatatc agctggtaca ttgccgtaga tgaaagactg   2820
agtgcgatat tatgtgtaat acataaattg atgatatagc tagcttagct catcggggga   2880
tcctagacgc gtgagatcag atctcggtga cgggcaggac cggacggggc ggtaccggca   2940
ggctgaagtc cagctgccag aaacccacgt catgccagtt cccgtgcttg aagccggccg   3000
cccgcagcat gccgcggggg gcatatccga gcgcctcgtg catgcgcacg ctcgggtcgt   3060
tgggcagccc gatgacagcg accacgctct tgaagccctg tgcctccagg gacttcagca   3120
ggtgggtgta gagcgtggag cccagtcccg tccgctggtg gcggggggag acgtacacgg   3180
tcgactcggc cgtccagtcg taggcgttgc gtgccttcca ggggcccgcg taggcgatgc   3240
cggcgacctc gccgtccacc tcggcgacga gccagggata gcgctcccgc agacggacga   3300
ggtcgtccgt ccactcctgc ggttcctgcg gctcggtacg gaagttgacc gtgcttgtct   3360
cgatgtagtg gttgacgatg gtgcagaccg ccggcatgtc cgcctcggtg gcacggcgga   3420
tgtcggccgg gcgtcgttct gggtccattg ttcttcttta ctctttgtgt gactgaggtt   3480
tggtctagtg ctttggtcat ctatatataa tgataacaac aatgagaaca agctttggag   3540
tgatcggagg gtctaggata catgagattc aagtggacta ggatctacac cgttggattt   3600
tgagtgtgga tatgtgtgag gttaatttta cttggtaacg gccacaaagg cctaaggaga   3660
ggtgttgaga cccttatcgg cttgaaccgc tggaataatg ccacgtggaa gataattcca   3720
tgaatcttat cgttatctat gagtgaaatt gtgtgatggt ggagtggtgc ttgctcattt   3780
tacttgcctg gtggacttgg ccctttcctt atggggaatt tatattttac ttactataga   3840
gctttcatac ctttttttta ccttggattt agttaatata taatggtatg attcatgaat   3900
aaaaatggga aatttttgaa tttgtactgc taaatgcata agattaggtg aaactgtgga   3960
atatatattt ttttcattta aaagcaaaat ttgcctttta ctagaattat aaatatagaa   4020
aaatatataa cattcaaata aaaatgaaaa taagaacttt caaaaaacag aactatgttt   4080
aatgtgtaaa gattagtcgc acatcaagtc atctgttaca atatgttaca acaagtcata   4140
agcccaacaa agttagcacg tctaaataaa ctaaagagtc cacgaaaata ttacaaatca   4200
taagcccaac aaagttattg atcaaaaaaa aaaaacgccc aacaaagcta aacaaagtcc   4260
aaaaaaaact tctcaagtct ccatcttcct ttatgaacat tgaaaactat acacaaaaca   4320
agtcagataa atctctttct gggcctgtct tcccaacctc ctacatcact tccctatcgg   4380
attgaatgtt ttacttgtac cttttccgtt gcaatgatat tgatagtatg tttgtgaaaa   4440
ctaatagggt taacaatcga agtcatggaa tatggatttg gtccaagatt ttccgagagc   4500
tttctagtag aaagcccatc accagaaatt tactagtaaa ataaatcacc aattaggttt   4560
cttattatgt gccaaattca atataattat agaggatatt tcaaatgaaa acgtatgaat   4620
gttattagta aatggtcagg taagacatta aaaaaatcct acgtcagata ttcaacttta   4680
```

```
aaaattcgat cagtgtggaa ttgtacaaaa atttgggatc tactatatat atataatgct   4740
ttacaacact tggatttttt tttggaggct ggaattttta atctacatat ttgttttggc   4800
catgcaccaa ctcattgttt agtgtaatac tttgattttg tcaaatatat gtgttcgtgt   4860
atatttgtat aagaatttct ttgaccatat acacacacac atatatatat atatatatat   4920
attatatatc atgcactttt aattgaaaaa ataatatata tatatatagt gcattttttc   4980
taacaaccat atatgttgcg attgatctgc aaaaatactg ctagagtaat gaaaaatata   5040
atctattgct gaaattatct cagatgttaa gattttctta aagtaaattc tttcaaattt   5100
tagctaaaag tcttgtaata actaaagaat aatacacaat ctcgaccacg gaaaaaaaac   5160
acataataaa tttgaatttc gaccgcggta cccggaattg ggttataatt acctcaggtc   5220
gaggaattaa ttcggtacgt acctaataac ttcgtatagc atacattata cgaagttata   5280
tggatctcga ggcattacgg cattacggca ctcgcgaggg tcccaattcg agcatggagc   5340
catttacaat tgaatatatc ctgccgccgc tgccgctttg cacccggtgg agcttgcatg   5400
ttggtttcta cgcagaactg agccggttag gcagataatt tccattgaga actgagccat   5460
gtgcaccttc cccccaacac ggtgagcgac ggggcaacgg agtgatccac atgggacttt   5520
taaacatcat ccgtcggatg gcgttgcgag agaagcagtc gatccgtgag atcagccgac   5580
gcaccgggca ggcgcgcaac acgatcgcaa agtatttgaa cgcaggtaca atcgagccga   5640
cgttcacggt accggaacga ccaagcaagc tagcttagta aagccctcgc tagattttaa   5700
tgcggatgtt gcgattactt cgccaactat tgcgataaca agaaaaagcc agcctttcat   5760
gatatatctc ccaatttgtg tagggcttat tatgcacgct taaaaataat aaaagcagac   5820
ttgacctgat agtttggctg tgagcaatta tgtgcttagt gcatctaacg cttgagttaa   5880
gccgcgccgc gaagcggcgt cggcttgaac gaattgttag acattatttg ccgactacct   5940
tggtgatctc gcctttcacg tagtggacaa attcttccaa ctgatctgcg cgcgaggcca   6000
agcgatcttc ttcttgtcca agataagcct gtctagcttc aagtatgacg ggctgatact   6060
gggccggcag gcgctccatt gcccagtcgg cagcgacatc cttcggcgcg attttgccgg   6120
ttactgcgct gtaccaaatg cgggacaacg taagcactac atttcgctca tcgccagccc   6180
agtcgggcgg cgagttccat agcgttaagg tttcatttag cgcctcaaat agatcctgtt   6240
caggaaccgg atcaaagagt tcctccgccg ctggacctac caaggcaacg ctatgttctc   6300
ttgcttttgt cagcaagata gccagatcaa tgtcgatcgt ggctggctcg aagatacctg   6360
caagaatgtc attgcgctgc cattctccaa attgcagttc gcgcttagct ggataacgcc   6420
acggaatgat gtcgtcgtgc acaacaatgg tgacttctac agcgcggaga atctcgctct   6480
ctccagggga agccgaagtt tccaaaaggt cgttgatcaa agctcgccgc gttgtttcat   6540
caagccttac ggtcaccgta accagcaaat caatatcact gtgtggcttc aggccgccat   6600
ccactgcgga gccgtacaaa tgtacggcca gcaacgtcgg ttcgagatgg cgctcgatga   6660
cgccaactac ctctgatagt tgagtcgata cttcggcgat caccgcttcc ctcatgatgt   6720
ttaactttgt tttagggcga ctgccctgct gcgtaacatc gttgctgctc cataacatca   6780
aacatcgacc cacggcgtaa cgcgcttgct gcttggatgc ccgaggcata gactgtaccc   6840
caaaaaaaca gtcataacaa gccatgaaaa ccgccactgc gccgttacca ccgctgcgtt   6900
cggtcaaggt tctggaccag ttgcgtgagc gcatacgcta cttgcattac agcttacgaa   6960
ccgaacaggc ttatgtccac tgggttcgtg ccttcatccg tttccacggt gtgcgtcacc   7020
cggcaacctt gggcagcagc gaagtcgagg catttctgtc ctggctggcg aacgagcgca   7080
```

```
aggtttcggt ctccacgcat cgtcaggcat tggcggcctt gctgttcttc tacggcaagt   7140
gctgtgcacg gatctgccct ggcttcagga gatcggaaga cctcggccgt ccgggcgctt   7200
gccggtggtg ctgaccccgg atgaagtctc tagagctcta gagggttcgc atcctcggtt   7260
ttctggaagg cgagcatcgt ttgttcgccc agcttctgta tggaacgggc atgcggatca   7320
gtgagggttt gcaactgcgg gtcaaggatc tggatttcga tcacggcacg atcatcgtgc   7380
gggagggcaa gggctccaag gatcgggcct tgatgttacc cgagagcttg gcacccagcc   7440
tgcgcgagca gggatcgatc caacccctcc gctgctatag tgcagtcggc ttctgacgtt   7500
cagtgcagcc gtcttctgaa aacgacatgt cgcacaagtc ctaagttacg cgacaggctg   7560
ccgccctgcc cttttcctgg cgttttcttg tcgcgtgttt tagtcgcata aagtagaata   7620
cttgcgacta gaaccggaga cattacgcca tgaacaagag cgccgccgct ggcctgctgg   7680
gctatgcccg cgtcagcacc gacgaccagg acttgaccaa ccaacgggcc gaactgcacg   7740
cggccggctg caccaagctg ttttccgaga agatcaccgg caccaggcgc gaccgcccgg   7800
agctggccag gatgcttgac cacctacgcc ctggcgacgt tgtgacagtg accaggctag   7860
accgcctggc ccgcagcacc cgcgacctac tggacattgc cgagcgcatc caggaggccg   7920
gcgcgggcct gcgtagcctg gcagagccgt gggccgacac caccacgccg gccggccgca   7980
tggtgttgac cgtgttcgcc ggcattgccg agttcgagcg ttccctaatc atcgaccgca   8040
cccggagcgg gcgcgaggcc gccaaggccc gaggcgtgaa gtttggcccc cgccctaccc   8100
tcaccccggc acagatcgcg cacgcccgcg agctgatcga ccaggaaggc cgcaccgtga   8160
aagaggcggc tgcactgctt ggcgtgcatc gctcgaccct gtaccgcgca cttgagcgca   8220
gcgaggaagt gacgcccacc gaggccaggc ggcgcggtgc cttccgtgag gacgcattga   8280
ccgaggccga cgccctggcg gccgccgaga atgaacgcca agaggaacaa gcatgaaacc   8340
gcaccaggac ggccaggacg aaccgttttt cattaccgaa gagatcgagg cggagatgat   8400
cgcggccggg tacgtgttcg agccgcccgc gcacgtctca accgtgcggc tgcatgaaat   8460
cctggccggt ttgtctgatg ccaagctggc ggcctggccg gccagcttgg ccgctgaaga   8520
aaccgagcgc cgccgtctaa aaaggtgatg tgtatttgag taaaacagct tgcgtcatgc   8580
ggtcgctgcg tatatgatgc gatgagtaaa taaacaaata cgcaagggga acgcatgaag   8640
gttatcgctg tacttaacca gaaaggcggg tcaggcaaga cgaccatcgc aacccatcta   8700
gcccgcgccc tgcaactcgc cggggccgat gttctgttag tcgattccga tccccagggc   8760
agtgcccgcg attgggcggc cgtgcgggaa gatcaaccgc taaccgttgt cggcatcgac   8820
cgcccgacga ttgaccgcga cgtgaaggcc atcggccggc gcgacttcgt agtgatcgac   8880
ggagcgcccc aggcggcgga cttggctgtg tccgcgatca aggcagccga cttcgtgctg   8940
attccggtgc agccaagccc ttacgacata tgggccaccg ccgacctggt ggagctggtt   9000
aagcagcgca ttgaggtcac ggatggaagg ctacaagcgg cctttgtcgt gtcgcgggcg   9060
atcaaaggca cgcgcatcgg cggtgaggtt gccgaggcgc tggccgggta cgagctgccc   9120
attcttgagt cccgtatcac gcagcgcgtg agctacccag gcactgccgc cgccggcaca   9180
accgttcttg aatcagaacc cgagggcgac gctgcccgcg aggtccaggc gctggccgct   9240
gaaattaaat caaaactcat ttgagttaat gaggtaaaga gaaaatgagc aaaagcacaa   9300
acacgctaag tgccggccgt ccgagcgcac gcagcagcaa ggctgcaacg ttggccagcc   9360
tggcagacac gccagccatg aagcgggtca actttcagtt gccggcggag gatcacacca   9420
```

-continued

```
agctgaagat gtacgcggta cgccaaggca agaccattac cgagctgcta tctgaataca    9480
tcgcgcagct accagagtaa atgagcaaat gaataaatga gtagatgaat tttagcggct    9540
aaaggaggcg gcatggaaaa tcaagaacaa ccaggcaccg acgccgtgga atgccccatg    9600
tgtggaggaa cgggcggttg gccaggcgta agcggctggg ttgtctgccg gccctgcaat    9660
ggcactggaa cccccaagcc cgaggaatcg gcgtgacggt cgcaaaccat ccggcccggt    9720
acaaatcggc gcggcgctgg gtgatgacct ggtggagaag ttgaaggccg cgcaggccgc    9780
ccagcggcaa cgcatcgagg cagaagcacg ccccggtgaa tcgtggcaag cggccgctga    9840
tcgaatccgc aaagaatccc ggcaaccgcc ggcagccggt gcgccgtcga ttaggaagcc    9900
gcccaagggc gacgagcaac cagatttttt cgttccgatg ctctatgacg tgggcacccg    9960
cgatagtcgc agcatcatgg acgtggccgt tttccgtctg tcgaagcgtg accgacgagc   10020
tggcgaggtg atccgctacg agcttccaga cgggcacgta gaggtttccg cagggccggc   10080
cggcatggcc agtgtgtggg attacgacct ggtactgatg gcggtttccc atctaaccga   10140
atccatgaac cgataccggg aagggaaggg agacaagccc ggccgcgtgt tccgtccaca   10200
cgttgcggac gtactcaagt tctgccggcg agccgatggc ggaaagcaga aagacgacct   10260
ggtagaaacc tgcattcggt taaacaccac gcacgttgcc atgcagcgta cgaagaaggc   10320
caagaacggc cgcctggtga cggtatccga gggtgaagcc ttgattagcc gctacaagat   10380
cgtaaagagc gaaaccgggc ggccggagta catcgagatc gagctagctg attggatgta   10440
ccgcgagatc acagaaggca agaacccgga cgtgctgacg gttcaccccg attacttttt   10500
gatcgatccc ggcatcggcc gttttctcta ccgcctggca cgccgcgccg caggcaaggc   10560
agaagccaga tggttgttca agacgatcta cgaacgcagt ggcagcgccg gagagttcaa   10620
gaagttctgt ttcaccgtgc gcaagctgat cgggtcaaat gacctgccgg agtacgattt   10680
gaaggaggag gcggggcagg ctggcccgat cctagtcatg cgctaccgca acctgatcga   10740
gggcgaagca tccgccggtt cctaatgtac ggagcagatg ctagggcaaa ttgccctagc   10800
aggggaaaaa ggtcgaaaag gtctctttcc tgtggatagc acgtacattg ggaacccaaa   10860
gccgtacatt gggaaccgga acccgtacat tgggaaccca aagccgtaca ttgggaaccg   10920
gtcacacatg taagtgactg atataaaaga gaaaaaaggc gatttttccg cctaaaactc   10980
tttaaaactt attaaaactc ttaaaacccg cctggcctgt gcataactgt ctggccagcg   11040
cacagccgaa gagctgcaaa aagcgcctac ccttcggtcg ctgcgctccc tacgccccgc   11100
cgcttcgcgt cggcctatcg cggccgctgg ccgctcaaaa atggctggcc tacggccagg   11160
caatctacca gggcgcggac aagccgcgcc gtcgccactc gaccgccggc gcccacatca   11220
aggcaccctg cctcgcgcgt ttcggtgatg acggtgaaaa cctctgacac atgcagctcc   11280
cggagacggt cacagcttgt ctgtaagcgg atgccgggag cagacaagcc cgtcagggcg   11340
cgtcagcggg tgttggcggg tgtcggggcg cagccatgac ccagtcacgt agcgatagcg   11400
gagtgtatac tggcttaact atgcggcatc agagcagatt gtactgagag tgcaccatat   11460
gcggtgtgaa ataccgcaca gatgcgtaag gagaaaatac cgcatcaggc gctcttccgc   11520
ttcctcgctc actgactcgc tgcgctcggt cgttcggctg cggcgagcgg tatcagctca   11580
ctcaaaggcg gtaatacggt tatccacaga atcaggggat aacgcaggaa agaacatgtg   11640
agcaaaaggc cagcaaaagg ccaggaaccg taaaaaggcc gcgttgctgg cgtttttcca   11700
taggctccgc ccccctgacg agcatcacaa aaatcgacgc tcaagtcaga ggtggcgaaa   11760
cccgacagga ctataaagat accaggcgtt tccccctgga agctccctcg tgcgctctcc   11820
```

```
tgttccgacc ctgccgctta ccggatacct gtccgccttt ctcccttcgg gaagcgtggc  11880
gctttctcat agctcacgct gtaggtatct cagttcggtg taggtcgttc gctccaagct  11940
gggctgtgtg cacgaacccc ccgttcagcc cgaccgctgc gccttatccg gtaactatcg  12000
tcttgagtcc aacccggtaa gacacgactt atcgccactg gcagcagcca ctggtaacag  12060
gattagcaga gcgaggtatg taggcggtgc tacagagttc ttgaagtggt ggcctaacta  12120
cggctacact agaaggacag tatttggtat ctgcgctctg ctgaagccag ttaccttcgg  12180
aaaaagagtt ggtagctctt gatccggcaa acaaaccacc gctggtagcg gtggtttttt  12240
tgtttgcaag cagcagatta cgcgcagaaa aaaaggatct caagaagatc cggaaaacgc  12300
aagcgcaaag agaaagcagg tagcttgcag tgggcttaca tggcgatagc tagactgggc  12360
ggttttatgg acagcaagcg aaccggaatt gcc                               12393
```

<210> SEQ ID NO 28
<211> LENGTH: 12414
<212> TYPE: DNA
<213> ORGANISM: Artificial
<220> FEATURE:
<223> OTHER INFORMATION: pTVE 470

<400> SEQUENCE: 28

```
agattcgaag ctcggtcccg tgggtgttct gtcgtctcgt tgtacaacga aatccattcc     60
cattccgcgc tcaagatggc ttcccctcgg cagttcatca gggctaaatc aatctagccg    120
acttgtccgg tgaaatgggc tgcactccaa cagaaacaat caaacaaaca tacacagcga    180
cttattcaca cgcgacaaat tacaacggta tatatcctgc cagtactcgg ccgtcgaccg    240
cggtaccccg gaattaagct tgcatgcctg caggcaattg gccgctgtac catgcatgat    300
ctggatttta gtactggatt ttggttttag gaattagaaa ttttattgat agaagtattt    360
tacaaataca aatacatact aagggtttct tatatgctca acacatgagc gaaaccctat    420
aggaacccta attcccttat ctgggaacta ctcacacatt attatggaga aaatagagag    480
agatagattt gtagagagag actggtgatt tcagcgtgtc caagcttgct agcttatgct    540
atagggaggc ataattgatg cttggcttga ataacagcat cacgatcacc agtatttttc    600
atgatatcgt cactaatctt cactgcttta gttccttcag cggaaaaaag cttaataaca    660
atattcatag gtttgctcac ttcactggga ttggaaactt tttggaagtc gctggtaaga    720
tttgtgccga tgccaaatgc agacttaatg ccacatttct cgcagtattt gtacagttcg    780
atacatctgt caacatttaa agcatcgcta tgaacaatta cttttgtgga aggatcgaca    840
cctattgatt tatagtgctt tacgactttt tcaatgtatt cctcagcaca accgctatct    900
tgacgaacac catggaaaac attggctaaa tcgtcggcag aattggctgt aaaagatttg    960
agaaacacat cagtagagaa tgtatccgtt aaggctatta aaagactagt accaaaagtt   1020
tggacccact ttaaggaagc aatacgattt gcttgtttat aattttgagt aatagctgca   1080
atgcccatat accactcgtg agcaaccgta ccagagacat ttagattata tttggcggcg   1140
aagtaaacat tagatgtacc aaggaaactt ccagggccct taaaatcctc ttgtgctttc   1200
atgagacctt ggagaacaat ttcctgggtg tgaggatcac gacgacgacg agtgccaaag   1260
tcagtaaagg cacatccggc tcggatgaga cgcttaccct tctcgtaagc tttttcaaac   1320
tgaccctcag gtgaccagtc cttatcgaca aatttaaaat aagattctga gacgagagca   1380
agcagtggaa tttcataaaa aatggtattc ttccagaggc cgtgaataaa gattgagaga   1440
```

```
tccttagttt cagaatcata attaagggaa attgaatttt caggatcaaa ttcgaactca   1500
tgcatgaatt cataaaatga ttcctttaaa taaggacagt tcttgcgaag ccattgctct   1560
tcttcaggaa gtaaatgtaa attccgtaag cctcttattt gttcccgtaa ccagttataa   1620
gcctcctgat ttaatgccat ttttggggac cggtttgtat acttatatga tacttgagca   1680
tccggataat gctctaaaac ggcttgaagc atggtgagtt tgtaaagatc cgtatcgagg   1740
atagagacaa cagcaacctt gcgcttcttc ttgggcggtt cacccatggt tttggtttaa   1800
taagaagaga aaagagttct tttgttatgg ctgaagtaat agagaaatga gctcgagtcc   1860
tctccaaatg aaatgaactt ccttatatag aggaagggtc ttgcgaagga tagtgggatt   1920
gtgcgtcatc ccttacgtca gtggagatat cacatcaatc cacttgcttt gaagacgtgg   1980
ttggaacgtc ttcttttttcc acgatgctcc tcgtgggtgg gggtccatct ttgggaccac   2040
tgtcggcaga ggcatcttga acgatagcct ttcctttatc gcaatgatgg catttgtagg   2100
tgccaccttc cttttctact gtccttttga tgaagtgaca gatagctggg caatggaatc   2160
cgaggaggtt tcccgatatt accctttgtt gaaaagtctc aatagccctt tggtcttctg   2220
agactgtatc tttgatattc ttggagtaga cgagagtgtc gtgctccacc atgttgacga   2280
agattttctt cttgtcattg agtcgtaaaa gactctgtat gaactgttcg ccagtcttca   2340
cggcgagttc tgttagatcc tcgatctgaa tttttgactc catgtatggt gcatatggcg   2400
cgccatatgc ccgggccctg tacagcggcc gcgttaacgc gtatactcta gagcgatcgc   2460
ccgggccggc catttaaatg aattcgagct cggtacccaa acgcggccgc aagctataac   2520
ttcgtatagc atacattata cgaagttatt cgactctaga ggatcccaat tcccatgcat   2580
ggagtcaaag attcaaatag aggacacttc tcgaactcgg ccgtcgaact cggccgtcga   2640
gtacatggtc gataagaaaa ggcaatttgt agatgttaat tcccatcttg aaagaaatat   2700
agtttaaata tttattgata aaataacaag tcaggtatta tagtccaagc aaaaacataa   2760
atttattgat gcaagtttaa attcagaaat atttcaataa ctgattatat cagctggtac   2820
attgccgtag atgaaagact gagtgcgata ttatgtgtaa tacataaatt gatgatatag   2880
ctagcttagc tcatcggggg atcctagacg cgtgagatca gatctcggtg acgggcagga   2940
ccggacgggg cggtaccggc aggctgaagt ccagctgcca gaaacccacg tcatgccagt   3000
tcccgtgctt gaagccggcc gcccgcagca tgccgcgggg ggcatatccg agcgcctcgt   3060
gcatgcgcac gctcgggtcg ttgggcagcc cgatgacagc gaccacgctc ttgaagccct   3120
gtgcctccag ggacttcagc aggtgggtgt agagcgtgga gcccagtccc gtccgctggt   3180
ggcgggggga gacgtacacg gtcgactcgg ccgtccagtc gtaggcgttg cgtgccttcc   3240
aggggcccgc gtaggcgatg ccggcgacct cgccgtccac ctcggcgacg agccagggat   3300
agcgctcccg cagacggacg aggtcgtccg tccactcctg cggttcctgc ggctcggtac   3360
ggaagttgac cgtgcttgtc tcgatgtagt ggttgacgat ggtgcagacc gccggcatgt   3420
ccgcctcggt ggcacggcgg atgtcggccg ggcgtcgttc tgggtccatt gttcttcttt   3480
actctttgtg tgactgaggt ttggtctagt gctttggtca tctatatata atgataacaa   3540
caatgagaac aagctttgga gtgatcggag ggtctaggat acatgagatt caagtggact   3600
aggatctaca ccgttggatt ttgagtgtgg atatgtgtga ggttaatttt acttggtaac   3660
ggccacaaag gcctaaggag aggtgttgag acccttatcg gcttgaaccg ctggaataat   3720
gccacgtgga agataattcc atgaatctta tcgttatcta tgagtgaaat tgtgtgatgg   3780
tggagtggtg cttgctcatt ttacttgcct ggtggacttg gccctttcct tatggggaat   3840
```

```
ttatatttta cttactatag agctttcata cctttttttt accttggatt tagttaatat   3900
ataatggtat gattcatgaa taaaaatggg aaatttttga atttgtactg ctaaatgcat   3960
aagattaggt gaaactgtgg aatatatatt tttttcattt aaaagcaaaa tttgcctttt   4020
actagaatta taaatataga aaaatatata acattcaaat aaaaatgaaa ataagaactt   4080
tcaaaaaaca gaactatgtt taatgtgtaa agattagtcg cacatcaagt catctgttac   4140
aatatgttac aacaagtcat aagcccaaca aagttagcac gtctaaataa actaaagagt   4200
ccacgaaaat attacaaatc ataagcccaa caaagttatt gatcaaaaaa aaaaaacgcc   4260
caacaaagct aaacaaagtc caaaaaaaac ttctcaagtc tccatcttcc tttatgaaca   4320
ttgaaaacta tacacaaaac aagtcagata aatctctttc tgggcctgtc ttcccaacct   4380
cctacatcac ttccctatcg gattgaatgt tttacttgta ccttttccgt tgcaatgata   4440
ttgatagtat gtttgtgaaa actaataggg ttaacaatcg aagtcatgga atatggattt   4500
ggtccaagat tttccgagag ctttctagta gaaagcccat caccagaaat ttactagtaa   4560
aataaatcac caattaggtt tcttattatg tgccaaattc aatataatta tagaggatat   4620
ttcaaatgaa aacgtatgaa tgttattagt aaatggtcag gtaagacatt aaaaaaatcc   4680
tacgtcagat attcaacttt aaaaattcga tcagtgtgga attgtacaaa aatttgggat   4740
ctactatata tatataatgc tttacaacac ttggattttt ttttggaggc tggaattttt   4800
aatctacata tttgttttgg ccatgcacca actcattgtt tagtgtaata ctttgatttt   4860
gtcaaatata tgtgttcgtg tatatttgta taagaatttc tttgaccata tacacacaca   4920
catatatata tatatatata tattatatat catgcacttt taattgaaaa aataatatat   4980
atatatatag tgcatttttt ctaacaacca tatatgttgc gattgatctg caaaaatact   5040
gctagagtaa tgaaaaatat aatctattgc tgaaattatc tcagatgtta agattttctt   5100
aaagtaaatt ctttcaaatt ttagctaaaa gtcttgtaat aactaaagaa taatacacaa   5160
tctcgaccac ggaaaaaaaa cacataataa atttgaattt cgaccgcggt acccggaatt   5220
gggttataat tacctcaggt cgaggaatta attcggtacg tacctaataa cttcgtatag   5280
catacattat acgaagttat atggatctcg aggcattacg gcattacggc actcgcgagg   5340
gtcccaattc gagcatggag ccatttacaa ttgaatatat cctgccgccg ctgccgcttt   5400
gcacccggtg gagcttgcat gttggtttct acgcagaact gagccggtta ggcagataat   5460
ttccattgag aactgagcca tgtgcacctt ccccccaaca cggtgagcga cggggcaacg   5520
gagtgatcca catgggactt ttaaacatca tccgtcggat ggcgttgcga gagaagcagt   5580
cgatccgtga gatcagccga cgcaccgggc aggcgcgcaa cacgatcgca aagtatttga   5640
acgcaggtac aatcgagccg acgttcacgg taccggaacg accaagcaag ctagcttagt   5700
aaagccctcg ctagatttta atgcggatgt tgcgattact tcgccaacta ttgcgataac   5760
aagaaaaagc cagcctttca tgatatatct cccaatttgt gtagggctta ttatgcacgc   5820
ttaaaaataa taaaagcaga cttgacctga tagtttggct gtgagcaatt atgtgcttag   5880
tgcatctaac gcttgagtta agccgcgccg cgaagcggcg tcggcttgaa cgaattgtta   5940
gacattattt gccgactacc ttggtgatct cgcctttcac gtagtggaca aattcttcca   6000
actgatctgc gcgcgaggcc aagcgatctt cttcttgtcc aagataagcc tgtctagctt   6060
caagtatgac gggctgatac tgggccggca ggcgctccat tgcccagtcg gcagcgacat   6120
ccttcggcgc gattttgccg gttactgcgc tgtaccaaat gcgggacaac gtaagcacta   6180
```

```
catttcgctc atcgccagcc cagtcgggcg gcgagttcca tagcgttaag gtttcattta   6240
gcgcctcaaa tagatcctgt tcaggaaccg gatcaaagag ttcctccgcc gctggaccta   6300
ccaaggcaac gctatgttct cttgcttttg tcagcaagat agccagatca atgtcgatcg   6360
tggctggctc gaagatacct gcaagaatgt cattgcgctg ccattctcca aattgcagtt   6420
cgcgcttagc tggataacgc cacggaatga tgtcgtcgtg cacaacaatg gtgacttcta   6480
cagcgcggag aatctcgctc tctccagggg aagccgaagt ttccaaaagg tcgttgatca   6540
aagctcgccg cgttgtttca tcaagcctta cggtcaccgt aaccagcaaa tcaatatcac   6600
tgtgtggctt caggccgcca tccactgcgg agccgtacaa atgtacggcc agcaacgtcg   6660
gttcgagatg gcgctcgatg acgccaacta cctctgatag ttgagtcgat acttcggcga   6720
tcaccgcttc cctcatgatg tttaactttg ttttagggcg actgccctgc tgcgtaacat   6780
cgttgctgct ccataacatc aaacatcgac ccacggcgta acgcgcttgc tgcttggatg   6840
cccgaggcat agactgtacc ccaaaaaaac agtcataaca agccatgaaa accgccactg   6900
cgccgttacc accgctgcgt tcggtcaagg ttctggacca gttgcgtgag cgcatacgct   6960
acttgcatta cagcttacga accgaacagg cttatgtcca ctgggttcgt gccttcatcc   7020
gtttccacgg tgtgcgtcac ccggcaacct tgggcagcag cgaagtcgag gcatttctgt   7080
cctggctggc gaacgagcgc aaggtttcgg tctccacgca tcgtcaggca ttggcggcct   7140
tgctgttctt ctacggcaag tgctgtgcac ggatctgccc tggcttcagg agatcggaag   7200
acctcggccg tccgggcgct tgccggtggt gctgaccccg gatgaagtct ctagagctct   7260
agagggttcg catcctcggt tttctggaag gcgagcatcg tttgttcgcc cagcttctgt   7320
atggaacggg catgcggatc agtgagggtt tgcaactgcg ggtcaaggat ctggatttcg   7380
atcacggcac gatcatcgtg cgggagggca agggctccaa ggatcgggcc ttgatgttac   7440
ccgagagctt ggcacccagc ctgcgcgagc agggatcgat ccaacccctc cgctgctata   7500
gtgcagtcgg cttctgacgt tcagtgcagc cgtcttctga aaacgacatg tcgcacaagt   7560
cctaagttac gcgacaggct gccgccctgc cctttttcctg gcgttttctt gtcgcgtgtt   7620
ttagtcgcat aaagtagaat acttgcgact agaaccggag acattacgcc atgaacaaga   7680
gcgccgccgc tggcctgctg ggctatgccc gcgtcagcac cgacgaccag gacttgacca   7740
accaacgggc cgaactgcac gcggccggct gcaccaagct gttttccgag aagatcaccg   7800
gcaccaggcg cgaccgcccg gagctggcca ggatgcttga ccacctacgc cctggcgacg   7860
ttgtgacagt gaccaggcta gaccgcctgg cccgcagcac ccgcgaccta ctggacattg   7920
ccgagcgcat ccaggaggcc ggcgcgggcc tgcgtagcct ggcagagccg tgggccgaca   7980
ccaccacgcc ggccggccgc atggtgttga ccgtgttcgc cggcattgcc gagttcgagc   8040
gttccctaat catcgaccgc acccggagcg ggcgcgaggc cgccaaggcc cgaggcgtga   8100
agtttggccc ccgccctacc ctcaccccgg cacagatcgc gcacgcccgc gagctgatcg   8160
accaggaagg ccgcaccgtg aaagaggcgg ctgcactgct tggcgtgcat cgctcgaccc   8220
tgtaccgcgc acttgagcgc agcgaggaag tgacgcccac cgaggccagg cggcgcggtg   8280
ccttccgtga ggacgcattg accgaggccg acgccctggc ggccgccgag aatgaacgcc   8340
aagaggaaca agcatgaaac cgcaccagga cggccaggac gaaccgtttt tcattaccga   8400
agagatcgag gcggagatga tcgcggccgg gtacgtgttc gagccgcccg cgcacgtctc   8460
aaccgtgcgg ctgcatgaaa tcctggccgg tttgtctgat gccaagctgg cggcctggcc   8520
ggccagcttg gccgctgaag aaaccgagcg ccgccgtcta aaaaggtgat gtgtatttga   8580
```

```
gtaaaacagc ttgcgtcatg cggtcgctgc gtatatgatg cgatgagtaa ataaacaaat   8640
acgcaagggg aacgcatgaa ggttatcgct gtacttaacc agaaaggcgg gtcaggcaag   8700
acgaccatcg caacccatct agcccgcgcc ctgcaactcg ccggggccga tgttctgtta   8760
gtcgattccg atccccaggg cagtgcccgc gattgggcgg ccgtgcggga agatcaaccg   8820
ctaaccgttg tcggcatcga ccgcccgacg attgaccgcg acgtgaaggc catcggccgg   8880
cgcgacttcg tagtgatcga cggagcgccc caggcggcgg acttggctgt gtccgcgatc   8940
aaggcagccg acttcgtgct gattccggtg cagccaagcc cttacgacat atgggccacc   9000
gccgacctgg tggagctggt taagcagcgc attgaggtca cggatggaag gctacaagcg   9060
gcctttgtcg tgtcgcgggc gatcaaaggc acgcgcatcg gcggtgaggt tgccgaggcg   9120
ctggccgggt acgagctgcc cattcttgag tcccgtatca cgcagcgcgt gagctaccca   9180
ggcactgccg ccgccggcac aaccgttctt gaatcagaac ccgagggcga cgctgcccgc   9240
gaggtccagg cgctggccgc tgaaattaaa tcaaaactca tttgagttaa tgaggtaaag   9300
agaaaatgag caaaagcaca aacacgctaa gtgccggccg tccgagcgca cgcagcagca   9360
aggctgcaac gttggccagc ctggcagaca cgccagccat gaagcgggtc aactttcagt   9420
tgccggcgga ggatcacacc aagctgaaga tgtacgcggt acgccaaggc aagaccatta   9480
ccgagctgct atctgaatac atcgcgcagc taccagagta aatgagcaaa tgaataaatg   9540
agtagatgaa ttttagcggc taaaggaggc ggcatggaaa atcaagaaca accaggcacc   9600
gacgccgtgg aatgccccat gtgtggagga acgggcggtt ggccaggcgt aagcggctgg   9660
gttgtctgcc ggccctgcaa tggcactgga acccccaagc ccgaggaatc ggcgtgacgg   9720
tcgcaaacca tccggcccgg tacaaatcgg cgcggcgctg ggtgatgacc tggtggagaa   9780
gttgaaggcc gcgcaggccg cccagcggca acgcatcgag gcagaagcac gccccggtga   9840
atcgtggcaa gcggccgctg atcgaatccg caaagaatcc cggcaaccgc cggcagccgg   9900
tgcgccgtcg attaggaagc cgcccaaggg cgacgagcaa ccagattttt tcgttccgat   9960
gctctatgac gtgggcaccc gcgatagtcg cagcatcatg gacgtggccg ttttccgtct  10020
gtcgaagcgt gaccgacgag ctggcgaggt gatccgctac gagcttccag acgggcacgt  10080
agaggtttcc gcagggccgg ccggcatggc cagtgtgtgg gattacgacc tggtactgat  10140
ggcggtttcc catctaaccg aatccatgaa ccgataccgg gaagggaagg gagacaagcc  10200
cggccgcgtg ttccgtccac acgttgcgga cgtactcaag ttctgccggc gagccgatgg  10260
cggaaagcag aaagacgacc tggtagaaac ctgcattcgg ttaaacacca cgcacgttgc  10320
catgcagcgt acgaagaagg ccaagaacgg ccgcctggtg acggtatccg agggtgaagc  10380
cttgattagc cgctacaaga tcgtaaagag cgaaaccggg cggccggagt acatcgagat  10440
cgagctagct gattggatgt accgcgagat cacagaaggc aagaacccgg acgtgctgac  10500
ggttcacccc gattactttt tgatcgatcc cggcatcggc cgttttctct accgcctggc  10560
acgccgcgcc gcaggcaagg cagaagccag atggttgttc aagacgatct acgaacgcag  10620
tggcagcgcc ggagagttca agaagttctg tttcaccgtg cgcaagctga tcgggtcaaa  10680
tgacctgccg gagtacgatt tgaaggagga ggcggggcag gctggcccga tcctagtcat  10740
gcgctaccgc aacctgatcg agggcgaagc atccgccggt tcctaatgta cggagcagat  10800
gctagggcaa attgccctag caggggaaaa aggtcgaaaa ggtctctttc ctgtggatag  10860
cacgtacatt gggaacccaa agccgtacat tgggaaccgg aacccgtaca ttgggaaccc  10920
```

```
aaagccgtac attgggaacc ggtcacacat gtaagtgact gatataaaag agaaaaaagg  10980
cgatttttcc gcctaaaact ctttaaaact tattaaaact cttaaaaccc gcctggcctg  11040
tgcataactg tctggccagc gcacagccga agagctgcaa aaagcgccta cccttcggtc  11100
gctgcgctcc ctacgccccg ccgcttcgcg tcggcctatc gcggccgctg gccgctcaaa  11160
aatggctggc ctacggccag gcaatctacc agggcgcgga caagccgcgc cgtcgccact  11220
cgaccgccgg cgcccacatc aaggcaccct gcctcgcgcg tttcggtgat gacggtgaaa  11280
acctctgaca catgcagctc ccggagacgg tcacagcttg tctgtaagcg gatgccggga  11340
gcagacaagc ccgtcagggc gcgtcagcgg gtgttggcgg gtgtcggggc gcagccatga  11400
cccagtcacg tagcgatagc ggagtgtata ctggcttaac tatgcggcat cagagcagat  11460
tgtactgaga gtgcaccata tgcggtgtga aataccgcac agatgcgtaa ggagaaaata  11520
ccgcatcagg cgctcttccg cttcctcgct cactgactcg ctgcgctcgg tcgttcggct  11580
gcggcgagcg gtatcagctc actcaaaggc ggtaatacgg ttatccacag aatcagggga  11640
taacgcagga aagaacatgt gagcaaaagg ccagcaaaag gccaggaacc gtaaaaaggc  11700
cgcgttgctg gcgtttttcc ataggctccg cccccctgac gagcatcaca aaaatcgacg  11760
ctcaagtcag aggtggcgaa acccgacagg actataaaga taccaggcgt ttccccctgg  11820
aagctccctc gtgcgctctc ctgttccgac cctgccgctt accggatacc tgtccgcctt  11880
tctcccttcg ggaagcgtgg cgctttctca tagctcacgc tgtaggtatc tcagttcggt  11940
gtaggtcgtt cgctccaagc tgggctgtgt gcacgaaccc cccgttcagc ccgaccgctg  12000
cgccttatcc ggtaactatc gtcttgagtc caacccggta agacacgact tatcgccact  12060
ggcagcagcc actggtaaca ggattagcag agcgaggtat gtaggcggtg ctacagagtt  12120
cttgaagtgg tggcctaact acggctacac tagaaggaca gtatttggta tctgcgctct  12180
gctgaagcca gttaccttcg gaaaaagagt tggtagctct tgatccggca aacaaaccac  12240
cgctggtagc ggtggttttt ttgtttgcaa gcagcagatt acgcgcagaa aaaaaggatc  12300
tcaagaagat ccggaaaacg caagcgcaaa gagaaagcag gtagcttgca gtgggcttac  12360
atggcgatag ctagactggg cggttttatg gacagcaagc gaaccggaat tgcc        12414
```

<210> SEQ ID NO 29
<211> LENGTH: 12366
<212> TYPE: DNA
<213> ORGANISM: Artificial
<220> FEATURE:
<223> OTHER INFORMATION: pTVE496

<400> SEQUENCE: 29

```
agattcgaag ctcggtcccg tgggtgttct gtcgtctcgt tgtacaacga aatccattcc     60
cattccgcgc tcaagatggc ttcccctcgg cagttcatca gggctaaatc aatctagccg    120
acttgtccgg tgaaatgggc tgcactccaa cagaaacaat caaacaaaca tacacagcga    180
cttattcaca cgcgacaaat tacaacggta tatatcctgc cagtactcgg ccgtcgaccg    240
cggtaccccg gaattaagct tgcatgcctg caggcaattg gccgctgtac catgcatgat    300
ctggatttta gtactggatt ttggttttag gaattagaaa ttttattgat agaagtattt    360
tacaaataca aatacatact aagggtttct tatatgctca acacatgagc gaaaccctat    420
aggaacccta attcccttat ctgggaacta ctcacacatt attatggaga aaatagagag    480
agatagattt gtagagagag actggtgatt tcagcgtgtc caagcttgct agctcattct    540
ttgtttccaa gaacttgctt aacaggttcg gtttggtcca catatagtct atgttcttgg    600
```

```
atatacctga tgaccgaatt aggtaacaaa tattgtacag acatggcgcg tctgataaat    660
agacgaactt tcgtggaaga aatatcatta tagatgagtt gcttgatgat aagaatattc    720
cttctatgtt catacataat atcatgggat aacaaaaaag accttacatc agaaccagta    780
cgttcgacaa tcaaacaacc gtaattaccg agaatgtgat gtaaatcggc gtccgcccaa    840
acgtttggtt cacccattga ctctattagg tcaccaccag ccagcaacat tattttcaca    900
ccaatttttt ctccagtaac agtagctaca ccacctctct taatattgat ttcgtgattg    960
aaatgatcca agaccttggc agttcttgtg tatgaaggtt gcaatgactc ccatgcatcc   1020
accatcaacc aagatgaggt tctttcgcag gccaattcac acatacgtac tctatggtag   1080
gatggggcca agccttgctt ttgatagtta tcactaacag gggagtaata tccacctatg   1140
acttcaaacc ttgtttgttc agagattgca tctaaagcca tttcaaacat tcttagatgc   1200
aagtaggtga ttggtgaaaa agacccacat gctactatta ctaacggcag tttatttgga   1260
tccagtaatt ttttcgataa tctgtgtgag gggaattcgt agtcttccaa ggttcttgct   1320
tgacgaacga ttccatgtgg aacttcttct aaatcagcaa tctgatattt ctgaacacct   1380
ctagtttctg attctgtggt tgaatctgaa ccgtatctct ccttggatct aaaatccgcg   1440
tcatcatctt cggaagacac ttctgcggaa agtggttgaa agtcgtcttg gttcaatgga   1500
atatgctgat gttttttatc attgccttct ttacgactgt gatgatggtg atgatgatgc   1560
ttaggatgct tttcttcct cttaatatta aaaggtgcat ctatagagga attcgcatcg    1620
gctaagacgt atggaataat tggaatagat ttgggaattt tagattccgg gtcgggtgga   1680
ggaatcaatt cctcgtctgc agatggcggt ttgaaatccg gagctcttgt gggatccatg   1740
gttttggttt aataagaaga gaaaagagtt cttttgttat ggctgaagta atagagaaat   1800
gagctcgagt cctctccaaa tgaaatgaac ttccttatat agaggaaggg tcttgcgaag   1860
gatagtggga ttgtgcgtca tcccttacgt cagtggagat atcacatcaa tccacttgct   1920
ttgaagacgt ggttggaacg tcttcttttt ccacgatgct cctcgtgggt gggggtccat   1980
ctttgggacc actgtcggca gaggcatctt gaacgatagc ctttccttta tcgcaatgat   2040
ggcatttgta ggtgccacct tccttttcta ctgtcctttt gatgaagtga cagatagctg   2100
ggcaatggaa tccgaggagg tttcccgata ttaccctttg ttgaaaagtc tcaatagccc   2160
tttggtcttc tgagactgta tctttgatat tcttggagta gacgagagtg tcgtgctcca   2220
ccatgttgac gaagattttc ttcttgtcat tgagtcgtaa aagactctgt atgaactgtt   2280
cgccagtctt cacggcgagt tctgttagat cctcgatctg aatttttgac tccatgtatg   2340
gtgcatatgg cgcgccatat gcccgggccc tgtacagcgg ccgcgttaac gcgtatactc   2400
tagagcgatc gcccgggccg gccatttaaa tgaattcgag ctcggtaccc aaacgcggcc   2460
gcaagctata acttcgtata gcatacatta tacgaagtta ttcgactcta gaggatccca   2520
attcccatgc atggagtcaa agattcaaat agaggacact tctcgaactc ggccgtcgaa   2580
ctcggccgtc gagtacatgg tcgataagaa aaggcaattt gtagatgtta attcccatct   2640
tgaaagaaat atagtttaaa tatttattga taaaataaca agtcaggtat tatagtccaa   2700
gcaaaaacat aaatttattg atgcaagttt aaattcagaa atatttcaat aactgattat   2760
atcagctggt acattgccgt agatgaaaga ctgagtgcga tattatgtgt aatacataaa   2820
ttgatgatat agctagctta gctcatcggg ggatcctaga cgcgtgagat cagatctcgg   2880
tgacgggcag gaccggacgg ggcggtaccg gcaggctgaa gtccagctgc cagaaaccca   2940
```

```
cgtcatgcca gttcccgtgc ttgaagccgg ccgcccgcag catgccgcgg ggggcatatc   3000
cgagcgcctc gtgcatgcgc acgctcgggt cgttgggcag cccgatgaca gcgaccacgc   3060
tcttgaagcc ctgtgcctcc agggacttca gcaggtgggt gtagagcgtg gagcccagtc   3120
ccgtccgctg gtggcggggg gagacgtaca cggtcgactc ggccgtccag tcgtaggcgt   3180
tgcgtgcctt ccaggggccc gcgtaggcga tgccggcgac ctcgccgtcc acctcggcga   3240
cgagccaggg atagcgctcc cgcagacgga cgaggtcgtc cgtccactcc tgcggttcct   3300
gcggctcggt acggaagttg accgtgcttg tctcgatgta gtggttgacg atggtgcaga   3360
ccgccggcat gtccgcctcg gtggcacggc ggatgtcggc cgggcgtcgt tctgggtcca   3420
ttgttcttct ttactctttg tgtgactgag gtttggtcta gtgctttggt catctatata   3480
taatgataac aacaatgaga acaagctttg gagtgatcgg agggtctagg atacatgaga   3540
ttcaagtgga ctaggatcta caccgttgga ttttgagtgt ggatatgtgt gaggttaatt   3600
ttacttggta acggccacaa aggcctaagg agaggtgttg agacccttat cggcttgaac   3660
cgctggaata atgccacgtg gaagataatt ccatgaatct tatcgttatc tatgagtgaa   3720
attgtgtgat ggtggagtgg tgcttgctca ttttacttgc ctggtggact tggccctttc   3780
cttatgggga atttatattt tacttactat agagctttca tacctttttt ttaccttgga   3840
tttagttaat atataatggt atgattcatg aataaaaatg ggaaattttt gaatttgtac   3900
tgctaaatgc ataagattag gtgaaactgt ggaatatata ttttttttcat ttaaaagcaa   3960
aatttgcctt ttactagaat tataaatata gaaaaatata taacattcaa ataaaaatga   4020
aaataagaac tttcaaaaaa cagaactatg tttaatgtgt aaagattagt cgcacatcaa   4080
gtcatctgtt acaatatgtt acaacaagtc ataagcccaa caaagttagc acgtctaaat   4140
aaactaaaga gtccacgaaa atattacaaa tcataagccc aacaaagtta ttgatcaaaa   4200
aaaaaaaacg cccaacaaag ctaaacaaag tccaaaaaaa acttctcaag tctccatctt   4260
cctttatgaa cattgaaaac tatacacaaa acaagtcaga taaatctctt tctgggcctg   4320
tcttcccaac ctcctacatc acttccctat cggattgaat gttttacttg tacctttttcc   4380
gttgcaatga tattgatagt atgtttgtga aaactaatag ggttaacaat cgaagtcatg   4440
gaatatggat ttggtccaag attttccgag agctttctag tagaaagccc atcaccagaa   4500
atttactagt aaaataaatc accaattagg tttcttatta tgtgccaaat tcaatataat   4560
tatagaggat atttcaaatg aaaacgtatg aatgttatta gtaaatggtc aggtaagaca   4620
ttaaaaaaat cctacgtcag atattcaact ttaaaaattc gatcagtgtg gaattgtaca   4680
aaaatttggg atctactata tatatataat gctttacaac acttggattt tttttggag   4740
gctggaattt ttaatctaca tatttgtttt ggccatgcac caactcattg tttagtgtaa   4800
tactttgatt ttgtcaaata tatgtgttcg tgtatatttg tataagaatt tctttgacca   4860
tatacacaca cacatatata tatatatata tatattatat atcatgcact tttaattgaa   4920
aaaataatat atatatatat agtgcatttt ttctaacaac catatatgtt gcgattgatc   4980
tgcaaaaata ctgctagagt aatgaaaaat ataatctatt gctgaaatta tctcagatgt   5040
taagattttc ttaaagtaaa ttctttcaaa ttttagctaa aagtcttgta ataactaaag   5100
aataatacac aatctcgacc acggaaaaaa aacacataat aaatttgaat ttcgaccgcg   5160
gtacccggaa ttgggttata attacctcag gtcgaggaat taattcggta cgtacctaat   5220
aacttcgtat agcatacatt atacgaagtt atatggatct cgaggcatta cggcattacg   5280
gcactcgcga gggtcccaat tcgagcatgg agccatttac aattgaatat atcctgccgc   5340
```

```
cgctgccgct ttgcacccgg tggagcttgc atgttggttt ctacgcagaa ctgagccggt   5400
taggcagata atttccattg agaactgagc catgtgcacc ttccccccaa cacggtgagc   5460
gacggggcaa cggagtgatc cacatgggac ttttaaacat catccgtcgg atggcgttgc   5520
gagagaagca gtcgatccgt gagatcagcc gacgcaccgg gcaggcgcgc aacacgatcg   5580
caaagtattt gaacgcaggt acaatcgagc cgacgttcac ggtaccggaa cgaccaagca   5640
agctagctta gtaaagccct cgctagattt taatgcggat gttgcgatta cttcgccaac   5700
tattgcgata acaagaaaaa gccagccttt catgatatat ctcccaattt gtgtagggct   5760
tattatgcac gcttaaaaat aataaaagca gacttgacct gatagtttgg ctgtgagcaa   5820
ttatgtgctt agtgcatcta acgcttgagt taagccgcgc cgcgaagcgg cgtcggcttg   5880
aacgaattgt tagacattat ttgccgacta ccttggtgat ctcgcctttc acgtagtgga   5940
caaattcttc caactgatct gcgcgcgagg ccaagcgatc ttcttcttgt ccaagataag   6000
cctgtctagc ttcaagtatg acgggctgat actgggccgg caggcgctcc attgcccagt   6060
cggcagcgac atccttcggc gcgattttgc cggttactgc gctgtaccaa atgcgggaca   6120
acgtaagcac tacatttcgc tcatcgccag cccagtcggg cggcgagttc catagcgtta   6180
aggtttcatt tagcgcctca aatagatcct gttcaggaac cggatcaaag agttcctccg   6240
ccgctggacc taccaaggca acgctatgtt ctcttgcttt tgtcagcaag atagccagat   6300
caatgtcgat cgtggctggc tcgaagatac ctgcaagaat gtcattgcgc tgccattctc   6360
caaattgcag ttcgcgctta gctggataac gccacggaat gatgtcgtcg tgcacaacaa   6420
tggtgacttc tacagcgcgg agaatctcgc tctctccagg ggaagccgaa gtttccaaaa   6480
ggtcgttgat caaagctcgc cgcgttgttt catcaagcct tacggtcacc gtaaccagca   6540
aatcaatatc actgtgtggc ttcaggccgc catccactgc ggagccgtac aaatgtacgg   6600
ccagcaacgt cggttcgaga tggcgctcga tgacgccaac tacctctgat agttgagtcg   6660
atacttcggc gatcaccgct tccctcatga tgtttaactt tgttttaggg cgactgccct   6720
gctgcgtaac atcgttgctg ctccataaca tcaaacatcg acccacggcg taacgcgctt   6780
gctgcttgga tgcccgaggc atagactgta ccccaaaaaa acagtcataa caagccatga   6840
aaaccgccac tgcgccgtta ccaccgctgc gttcggtcaa ggttctggac cagttgcgtg   6900
agcgcatacg ctacttgcat tacagcttac gaaccgaaca ggcttatgtc cactgggttc   6960
gtgccttcat ccgtttccac ggtgtgcgtc acccggcaac cttgggcagc agcgaagtcg   7020
aggcatttct gtcctggctg gcgaacgagc gcaaggtttc ggtctccacg catcgtcagg   7080
cattggcggc cttgctgttc ttctacggca agtgctgtgc acggatctgc cctggcttca   7140
ggagatcgga agacctcggc cgtccgggcg cttgccggtg gtgctgaccc cggatgaagt   7200
ctctagagct ctagagggtt cgcatcctcg gttttctgga aggcgagcat cgtttgttcg   7260
cccagcttct gtatggaacg ggcatgcgga tcagtgaggg tttgcaactg cgggtcaagg   7320
atctggattt cgatcacggc acgatcatcg tgcgggaggg caagggctcc aaggatcggg   7380
ccttgatgtt acccgagagc ttggcaccca gcctgcgcga gcagggatcg atccaacccc   7440
tccgctgcta tagtgcagtc ggcttctgac gttcagtgca gccgtcttct gaaaacgaca   7500
tgtcgcacaa gtcctaagtt acgcgacagg ctgccgccct gcccttttcc tggcgttttc   7560
ttgtcgcgtg ttttagtcgc ataaagtaga atacttgcga ctagaaccgg agacattacg   7620
ccatgaacaa gagcgccgcc gctggcctgc tgggctatgc ccgcgtcagc accgacgacc   7680
```

-continued

```
aggacttgac caaccaacgg gccgaactgc acgcggccgg ctgcaccaag ctgttttccg   7740

agaagatcac cggcaccagg cgcgaccgcc cggagctggc caggatgctt gaccacctac   7800

gccctggcga cgttgtgaca gtgaccaggc tagaccgcct ggcccgcagc acccgcgacc   7860

tactggacat tgccgagcgc atccaggagg ccggcgcggg cctgcgtagc ctggcagagc   7920

cgtgggccga caccaccacg ccggccggcc gcatggtgtt gaccgtgttc gccggcattg   7980

ccgagttcga gcgttcccta atcatcgacc gcacccggag cgggcgcgag gccgccaagg   8040

cccgaggcgt gaagtttggc ccccgcccta ccctcacccc ggcacagatc gcgcacgccc   8100

gcgagctgat cgaccaggaa ggccgcaccg tgaaagaggc ggctgcactg cttggcgtgc   8160

atcgctcgac cctgtaccgc gcacttgagc gcagcgagga agtgacgccc accgaggcca   8220

ggcggcgcgg tgccttccgt gaggacgcat tgaccgaggc cgacgccctg gcggccgccg   8280

agaatgaacg ccaagaggaa caagcatgaa accgcaccag gacggccagg acgaaccgtt   8340

tttcattacc gaagagatcg aggcggagat gatcgcggcc gggtacgtgt tcgagccgcc   8400

cgcgcacgtc tcaaccgtgc ggctgcatga aatcctggcc ggtttgtctg atgccaagct   8460

ggcggcctgg ccggccagct tggccgctga agaaaccgag cgccgccgtc taaaaaggtg   8520

atgtgtattt gagtaaaaca gcttgcgtca tgcggtcgct gcgtatatga tgcgatgagt   8580

aaataaacaa atacgcaagg ggaacgcatg aaggttatcg ctgtacttaa ccagaaaggc   8640

gggtcaggca agacgaccat cgcaacccat ctagcccgcg ccctgcaact cgccggggcc   8700

gatgttctgt tagtcgattc cgatccccag ggcagtgccc gcgattgggc ggccgtgcgg   8760

gaagatcaac cgctaaccgt tgtcggcatc gaccgcccga cgattgaccg cgacgtgaag   8820

gccatcggcc ggcgcgactt cgtagtgatc gacggagcgc cccaggcggc ggacttggct   8880

gtgtccgcga tcaaggcagc cgacttcgtg ctgattccgg tgcagccaag cccttacgac   8940

atatgggcca ccgccgacct ggtggagctg gttaagcagc gcattgaggt cacggatgga   9000

aggctacaag cggcctttgt cgtgtcgcgg gcgatcaaag gcacgcgcat cggcggtgag   9060

gttgccgagg cgctggccgg gtacgagctg cccattcttg agtcccgtat cacgcagcgc   9120

gtgagctacc caggcactgc cgccgccggc acaaccgttc ttgaatcaga acccgagggc   9180

gacgctgccc gcgaggtcca ggcgctggcc gctgaaatta aatcaaaact catttgagtt   9240

aatgaggtaa agagaaaatg agcaaaagca caaacacgct aagtgccggc cgtccgagcg   9300

cacgcagcag caaggctgca acgttggcca gcctggcaga cacgccagcc atgaagcggg   9360

tcaactttca gttgccggcg gaggatcaca ccaagctgaa gatgtacgcg gtacgccaag   9420

gcaagaccat taccgagctg ctatctgaat acatcgcgca gctaccagag taaatgagca   9480

aatgaataaa tgagtagatg aattttagcg gctaaaggag gcggcatgga aaatcaagaa   9540

caaccaggca ccgacgccgt ggaatgcccc atgtgtggag gaacgggcgg ttggccaggc   9600

gtaagcggct gggttgtctg ccggccctgc aatggcactg gaacccccaa gcccgaggaa   9660

tcggcgtgac ggtcgcaaac catccggccc ggtacaaatc ggcgcggcgc tgggtgatga   9720

cctggtggag aagttgaagg ccgcgcaggc cgcccagcgg caacgcatcg aggcagaagc   9780

acgccccggt gaatcgtggc aagcggccgc tgatcgaatc cgcaaagaat cccggcaacc   9840

gccggcagcc ggtgcgccgt cgattaggaa gccgcccaag ggcgacgagc aaccagattt   9900

tttcgttccg atgctctatg acgtgggcac ccgcgatagt cgcagcatca tggacgtggc   9960

cgttttccgt ctgtcgaagc gtgaccgacg agctggcgag gtgatccgct acgagcttcc  10020

agacgggcac gtagaggttt ccgcagggcc ggccggcatg gccagtgtgt gggattacga  10080
```

```
cctggtactg atggcggttt cccatctaac cgaatccatg aaccgatacc gggaagggaa  10140
gggagacaag cccggccgcg tgttccgtcc acacgttgcg gacgtactca agttctgccg  10200
gcgagccgat ggcggaaagc agaaagacga cctggtagaa acctgcattc ggttaaacac  10260
cacgcacgtt gccatgcagc gtacgaagaa ggccaagaac ggccgcctgg tgacggtatc  10320
cgagggtgaa gccttgatta gccgctacaa gatcgtaaag agcgaaaccg ggcggccgga  10380
gtacatcgag atcgagctag ctgattggat gtaccgcgag atcacagaag gcaagaaccc  10440
ggacgtgctg acggttcacc ccgattactt tttgatcgat cccggcatcg gccgttttct  10500
ctaccgcctg gcacgccgcg ccgcaggcaa ggcagaagcc agatggttgt tcaagacgat  10560
ctacgaacgc agtggcagcg ccggagagtt caagaagttc tgtttcaccg tgcgcaagct  10620
gatcgggtca aatgacctgc cggagtacga tttgaaggag gaggcggggc aggctggccc  10680
gatcctagtc atgcgctacc gcaacctgat cgagggcgaa gcatccgccg gttcctaatg  10740
tacggagcag atgctagggc aaattgccct agcaggggaa aaaggtcgaa aaggtctctt  10800
tcctgtggat agcacgtaca ttgggaaccc aaagccgtac attgggaacc ggaacccgta  10860
cattgggaac ccaaagccgt acattgggaa ccggtcacac atgtaagtga ctgatataaa  10920
agagaaaaaa ggcgattttt ccgcctaaaa ctctttaaaa cttattaaaa ctcttaaaac  10980
ccgcctggcc tgtgcataac tgtctggcca gcgcacagcc gaagagctgc aaaaagcgcc  11040
tacccttcgg tcgctgcgct ccctacgccc cgccgcttcg cgtcggccta tcgcggccgc  11100
tggccgctca aaaatggctg gcctacggcc aggcaatcta ccagggcgcg gacaagccgc  11160
gccgtcgcca ctcgaccgcc ggcgcccaca tcaaggcacc ctgcctcgcg cgtttcggtg  11220
atgacggtga aaacctctga cacatgcagc tcccggagac ggtcacagct tgtctgtaag  11280
cggatgccgg gagcagacaa gcccgtcagg gcgcgtcagc gggtgttggc gggtgtcggg  11340
gcgcagccat gacccagtca cgtagcgata gcggagtgta tactggctta actatgcggc  11400
atcagagcag attgtactga gagtgcacca tatgcggtgt gaaataccgc acagatgcgt  11460
aaggagaaaa taccgcatca ggcgctcttc cgcttcctcg ctcactgact cgctgcgctc  11520
ggtcgttcgg ctgcggcgag cggtatcagc tcactcaaag gcggtaatac ggttatccac  11580
agaatcaggg gataacgcag gaaagaacat gtgagcaaaa ggccagcaaa aggccaggaa  11640
ccgtaaaaag gccgcgttgc tggcgttttt ccataggctc cgcccccctg acgagcatca  11700
caaaaatcga cgctcaagtc agaggtggcg aaacccgaca ggactataaa gataccaggc  11760
gtttccccct ggaagctccc tcgtgcgctc tcctgttccg accctgccgc ttaccggata  11820
cctgtccgcc tttctccctt cgggaagcgt ggcgctttct catagctcac gctgtaggta  11880
tctcagttcg gtgtaggtcg ttcgctccaa gctgggctgt gtgcacgaac cccccgttca  11940
gcccgaccgc tgcgccttat ccggtaacta tcgtcttgag tccaacccgg taagacacga  12000
cttatcgcca ctggcagcag ccactggtaa caggattagc agagcgaggt atgtaggcgg  12060
tgctacagag ttcttgaagt ggtggcctaa ctacggctac actagaagga cagtatttgg  12120
tatctgcgct ctgctgaagc cagttacctt cggaaaaaga gttggtagct cttgatccgg  12180
caaacaaacc accgctggta gcggtggttt ttttgtttgc aagcagcaga ttacgcgcag  12240
aaaaaaagga tctcaagaag atccggaaaa cgcaagcgca aagagaaagc aggtagcttg  12300
cagtgggctt acatggcgat agctagactg ggcggtttta tggacagcaa gcgaaccgga  12360
attgcc                                                             12366
```

<210> SEQ ID NO 30
<211> LENGTH: 12384
<212> TYPE: DNA
<213> ORGANISM: Artificial
<220> FEATURE:
<223> OTHER INFORMATION: pTVE497

<400> SEQUENCE: 30

```
agattcgaag ctcggtcccg tgggtgttct gtcgtctcgt tgtacaacga aatccattcc     60
cattccgcgc tcaagatggc ttcccctcgg cagttcatca gggctaaatc aatctagccg    120
acttgtccgg tgaaatgggc tgcactccaa cagaaacaat caaacaaaca tacacagcga    180
cttattcaca cgcgacaaat tacaacggta tatatcctgc cagtactcgg ccgtcgaccg    240
cggtaccccg gaattaagct tgcatgcctg caggcaattg gccgctgtac catgcatgat    300
ctggatttta gtactggatt ttggttttag gaattagaaa ttttattgat agaagtattt    360
tacaaataca aatacatact aagggtttct tatatgctca acacatgagc gaaaccctat    420
aggaacccta attcccttat ctgggaacta ctcacacatt attatggaga aaatagagag    480
agatagattt gtagagagag actggtgatt tcagcgtgtc caagcttgct agctcattct    540
ttgtttccaa gaacttgctt aacaggttcg gtttggtcca catatagtct atgttcttgg    600
atatacctga tgaccgaatt aggtaacaaa tattgtacag acatggcgcg tctgataaat    660
agacgaactt tcgtggaaga aatatcatta tagatgagtt gcttgatgat aagaatattc    720
cttctatgtt catacataat atcatgggat aacaaaaaag accttacatc agaaccagta    780
cgttcgacaa tcaaacaacc gtaattaccg agaatgtgat gtaaatcggc gtccgcccaa    840
acgtttggtt cacccattga ctctattagg tcaccaccag ccagcaacat tattttcaca    900
ccaatttttt ctccagtaac agtagctaca ccacctctct taatattgat ttcgtgattg    960
aaatgatcca agaccttggc agttcttgtg tatgaaggtt gcaatgactc ccatgcatcc   1020
accatcaacc aagatgaggt tctttcgcag gccaattcac acatacgtac tctatggtag   1080
gatggggcca agccttgctt ttgatagtta tcactaacag gggagtaata tccacctatg   1140
acttcaaacc ttgtttgttc agagattgca tctaaagcca tttcaaacat tcttagatgc   1200
aagtaggtga ttggtgaaaa agacccacat gctactatta ctaacggcag tttatttgga   1260
tccagtaatt ttttcgataa tctgtgtgag gggaattcgt agtcttccaa ggttcttgct   1320
tgacgaacga ttccatgtgg aacttcttct aaatcagcaa tctgatattt ctgaacacct   1380
ctagtttctg attctgtggt tgaatctgaa ccgtatctct ccttggatct aaaatccgcg   1440
tcatcatctt cggaagacac ttctgcggaa agtggttgaa agtcgtcttg gttcaatgga   1500
atatgctgat gtttttatc attgccttct ttacgactgt gatgatggtg atgatgatgc   1560
ttaggatgct ttttcttcct cttaatatta aaaggtgcat ctatagagga attcgcatcg   1620
gctaagacgt atggaataat tggaatagat ttgggaattt tagattccgg gtcgggtgga   1680
ggaatcaatt cctcgtctgc agatggcggt ttgaaatccg gagctcttgt aaccttgcgc   1740
ttcttcttgg gatccatggt tttggtttaa taagaagaga aaagagttct tttgttatgg   1800
ctgaagtaat agagaaatga gctcgagtcc tctccaaatg aaatgaactt ccttatatag   1860
aggaagggtc ttgcgaagga tagtgggatt gtgcgtcatc ccttacgtca gtggagatat   1920
cacatcaatc cacttgcttt gaagacgtgg ttggaacgtc ttcttttcc acgatgctcc   1980
tcgtgggtgg gggtccatct ttgggaccac tgtcggcaga ggcatcttga acgatagcct   2040
ttcctttatc gcaatgatgg catttgtagg tgccaccttc cttttctact gtccttttga   2100
```

```
tgaagtgaca gatagctggg caatggaatc cgaggaggtt tcccgatatt accctttgtt   2160
gaaaagtctc aatagccctt tggtcttctg agactgtatc tttgatattc ttggagtaga   2220
cgagagtgtc gtgctccacc atgttgacga agattttctt cttgtcattg agtcgtaaaa   2280
gactctgtat gaactgttcg ccagtcttca cggcgagttc tgttagatcc tcgatctgaa   2340
tttttgactc catgtatggt gcatatggcg cgccatatgc ccgggccctg tacagcggcc   2400
gcgttaacgc gtatactcta gagcgatcgc ccgggccggc catttaaatg aattcgagct   2460
cggtacccaa acgcggccgc aagctataac ttcgtatagc atacattata cgaagttatt   2520
cgactctaga ggatcccaat tcccatgcat ggagtcaaag attcaaatag aggacacttc   2580
tcgaactcgg ccgtcgaact cggccgtcga gtacatggtc gataagaaaa ggcaatttgt   2640
agatgttaat tcccatcttg aaagaaatat agtttaaata tttattgata aaataacaag   2700
tcaggtatta tagtccaagc aaaaacataa atttattgat gcaagtttaa attcagaaat   2760
atttcaataa ctgattatat cagctggtac attgccgtag atgaaagact gagtgcgata   2820
ttatgtgtaa tacataaatt gatgatatag ctagcttagc tcatcggggg atcctagacg   2880
cgtgagatca gatctcggtg acgggcagga ccggacgggg cggtaccggc aggctgaagt   2940
ccagctgcca gaaacccacg tcatgccagt tcccgtgctt gaagccggcc gcccgcagca   3000
tgccgcgggg ggcatatccg agcgcctcgt gcatgcgcac gctcgggtcg ttgggcagcc   3060
cgatgacagc gaccacgctc ttgaagccct gtgcctccag ggacttcagc aggtgggtgt   3120
agagcgtgga gcccagtccc gtccgctggt ggcgggggga gacgtacacg gtcgactcgg   3180
ccgtccagtc gtaggcgttg cgtgccttcc aggggcccgc gtaggcgatg ccggcgacct   3240
cgccgtccac ctcggcgacg agccagggat agcgctcccg cagacggacg aggtcgtccg   3300
tccactcctg cggttcctgc ggctcggtac ggaagttgac cgtgcttgtc tcgatgtagt   3360
ggttgacgat ggtgcagacc gccggcatgt ccgcctcggt ggcacggcgg atgtcggccg   3420
ggcgtcgttc tgggtccatt gttcttcttt actctttgtg tgactgaggt ttggtctagt   3480
gctttggtca tctatatata atgataacaa caatgagaac aagctttgga gtgatcggag   3540
ggtctaggat acatgagatt caagtggact aggatctaca ccgttggatt ttgagtgtgg   3600
atatgtgtga ggttaatttt acttggtaac ggccacaaag gcctaaggag aggtgttgag   3660
acccttatcg gcttgaaccg ctggaataat gccacgtgga agataattcc atgaatctta   3720
tcgttatcta tgagtgaaat tgtgtgatgg tggagtggtg cttgctcatt ttacttgcct   3780
ggtggacttg gccctttcct tatggggaat ttatatttta cttactatag agctttcata   3840
cctttttttt accttggatt tagttaatat ataatggtat gattcatgaa taaaaatggg   3900
aaatttttga atttgtactg ctaaatgcat aagattaggt gaaactgtgg aatatatatt   3960
tttttcattt aaaagcaaaa tttgcctttt actagaatta taaatataga aaaatatata   4020
acattcaaat aaaaatgaaa ataagaactt tcaaaaaaca gaactatgtt taatgtgtaa   4080
agattagtcg cacatcaagt catctgttac aatatgttac aacaagtcat aagcccaaca   4140
aagttagcac gtctaaataa actaaagagt ccacgaaaat attacaaatc ataagcccaa   4200
caaagttatt gatcaaaaaa aaaaaacgcc caacaaagct aaacaaagtc caaaaaaaac   4260
ttctcaagtc tccatcttcc tttatgaaca ttgaaaacta tacacaaaac aagtcagata   4320
aatctctttc tgggcctgtc ttcccaacct cctacatcac ttccctatcg gattgaatgt   4380
tttacttgta ccttttccgt tgcaatgata ttgatagtat gtttgtgaaa actaataggg   4440
```

```
ttaacaatcg aagtcatgga atatggattt ggtccaagat tttccgagag ctttctagta   4500
gaaagcccat caccagaaat ttactagtaa aataaatcac caattaggtt tcttattatg   4560
tgccaaattc aatataatta tagaggatat ttcaaatgaa aacgtatgaa tgttattagt   4620
aaatggtcag gtaagacatt aaaaaaatcc tacgtcagat attcaacttt aaaaattcga   4680
tcagtgtgga attgtacaaa aatttgggat ctactatata tatataatgc tttacaacac   4740
ttggattttt ttttggaggc tggaattttt aatctacata tttgttttgg ccatgcacca   4800
actcattgtt tagtgtaata ctttgatttt gtcaaatata tgtgttcgtg tatatttgta   4860
taagaatttc tttgaccata tacacacaca catatatata tatatatata tattatatat   4920
catgcacttt taattgaaaa aataatatat atatatatag tgcatttttt ctaacaacca   4980
tatatgttgc gattgatctg caaaaatact gctagagtaa tgaaaaatat aatctattgc   5040
tgaaattatc tcagatgtta agattttctt aaagtaaatt ctttcaaatt ttagctaaaa   5100
gtcttgtaat aactaaagaa taatacacaa tctcgaccac ggaaaaaaaa cacataataa   5160
atttgaattt cgaccgcggt acccggaatt gggttataat tacctcaggt cgaggaatta   5220
attcggtacg tacctaataa cttcgtatag catacattat acgaagttat atggatctcg   5280
aggcattacg gcattacggc actcgcgagg gtcccaattc gagcatggag ccatttacaa   5340
ttgaatatat cctgccgccg ctgccgcttt gcacccggtg gagcttgcat gttggtttct   5400
acgcagaact gagccggtta ggcagataat ttccattgag aactgagcca tgtgcacctt   5460
ccccccaaca cggtgagcga cggggcaacg gagtgatcca catgggactt ttaaacatca   5520
tccgtcggat ggcgttgcga gagaagcagt cgatccgtga gatcagccga cgcaccgggc   5580
aggcgcgcaa cacgatcgca aagtatttga acgcaggtac aatcgagccg acgttcacgg   5640
taccggaacg accaagcaag ctagcttagt aaagccctcg ctagatttta atgcggatgt   5700
tgcgattact tcgccaacta ttgcgataac aagaaaaagc cagcctttca tgatatatct   5760
cccaatttgt gtagggctta ttatgcacgc ttaaaaataa taaaagcaga cttgacctga   5820
tagtttggct gtgagcaatt atgtgcttag tgcatctaac gcttgagtta agccgcgccg   5880
cgaagcggcg tcggcttgaa cgaattgtta gacattattt gccgactacc ttggtgatct   5940
cgcctttcac gtagtggaca aattcttcca actgatctgc gcgcgaggcc aagcgatctt   6000
cttcttgtcc aagataagcc tgtctagctt caagtatgac gggctgatac tgggccggca   6060
ggcgctccat tgcccagtcg gcagcgacat ccttcggcgc gattttgccg gttactgcgc   6120
tgtaccaaat gcgggacaac gtaagcacta catttcgctc atcgccagcc cagtcgggcg   6180
gcgagttcca tagcgttaag gtttcattta gcgcctcaaa tagatcctgt tcaggaaccg   6240
gatcaaagag ttcctccgcc gctggaccta ccaaggcaac gctatgttct cttgcttttg   6300
tcagcaagat agccagatca atgtcgatcg tggctggctc gaagatacct gcaagaatgt   6360
cattgcgctg ccattctcca aattgcagtt cgcgcttagc tggataacgc cacggaatga   6420
tgtcgtcgtg cacaacaatg gtgacttcta cagcgcggag aatctcgctc tctccagggg   6480
aagccgaagt ttccaaaagg tcgttgatca aagctcgccg cgttgtttca tcaagcctta   6540
cggtcaccgt aaccagcaaa tcaatatcac tgtgtggctt caggccgcca tccactgcgg   6600
agccgtacaa atgtacggcc agcaacgtcg gttcgagatg gcgctcgatg acgccaacta   6660
cctctgatag ttgagtcgat acttcggcga tcaccgcttc cctcatgatg tttaactttg   6720
ttttagggcg actgccctgc tgcgtaacat cgttgctgct ccataacatc aaacatcgac   6780
ccacggcgta acgcgcttgc tgcttggatg cccgaggcat agactgtacc ccaaaaaaac   6840
```

```
agtcataaca agccatgaaa accgccactg cgccgttacc accgctgcgt tcggtcaagg   6900
ttctggacca gttgcgtgag cgcatacgct acttgcatta cagcttacga accgaacagg   6960
cttatgtcca ctgggttcgt gccttcatcc gtttccacgg tgtgcgtcac ccggcaacct   7020
tgggcagcag cgaagtcgag gcatttctgt cctggctggc gaacgagcgc aaggtttcgg   7080
tctccacgca tcgtcaggca ttggcggcct tgctgttctt ctacggcaag tgctgtgcac   7140
ggatctgccc tggcttcagg agatcggaag acctcggccg tccgggcgct tgccggtggt   7200
gctgaccccg gatgaagtct ctagagctct agagggttcg catcctcggt tttctggaag   7260
gcgagcatcg tttgttcgcc cagcttctgt atggaacggg catgcggatc agtgagggtt   7320
tgcaactgcg ggtcaaggat ctggatttcg atcacggcac gatcatcgtg cgggagggca   7380
agggctccaa ggatcgggcc ttgatgttac ccgagagctt ggcacccagc ctgcgcgagc   7440
agggatcgat ccaacccctc cgctgctata gtgcagtcgg cttctgacgt tcagtgcagc   7500
cgtcttctga aaacgacatg tcgcacaagt cctaagttac gcgacaggct gccgccctgc   7560
ccttttcctg gcgttttctt gtcgcgtgtt ttagtcgcat aaagtagaat acttgcgact   7620
agaaccggag acattacgcc atgaacaaga gcgccgccgc tggcctgctg ggctatgccc   7680
gcgtcagcac cgacgaccag gacttgacca accaacgggc cgaactgcac gcggccggct   7740
gcaccaagct gttttccgag aagatcaccg gcaccaggcg cgaccgcccg gagctggcca   7800
ggatgcttga ccacctacgc cctggcgacg ttgtgacagt gaccaggcta gaccgcctgg   7860
cccgcagcac ccgcgaccta ctggacattg ccgagcgcat ccaggaggcc ggcgcgggcc   7920
tgcgtagcct ggcagagccg tgggccgaca ccaccacgcc ggccggccgc atggtgttga   7980
ccgtgttcgc cggcattgcc gagttcgagc gttccctaat catcgaccgc acccggagcg   8040
ggcgcgaggc cgccaaggcc cgaggcgtga agtttggccc ccgccctacc ctcaccccgg   8100
cacagatcgc gcacgcccgc gagctgatcg accaggaagg ccgcaccgtg aaagaggcgg   8160
ctgcactgct tggcgtgcat cgctcgaccc tgtaccgcgc acttgagcgc agcgaggaag   8220
tgacgcccac cgaggccagg cggcgcggtg ccttccgtga ggacgcattg accgaggccg   8280
acgccctggc ggccgccgag aatgaacgcc aagaggaaca agcatgaaac cgcaccagga   8340
cggccaggac gaaccgtttt tcattaccga agagatcgag gcggagatga tcgcggccgg   8400
gtacgtgttc gagccgcccg cgcacgtctc aaccgtgcgg ctgcatgaaa tcctggccgg   8460
tttgtctgat gccaagctgg cggcctggcc ggccagcttg gccgctgaag aaaccgagcg   8520
ccgccgtcta aaaaggtgat gtgtatttga gtaaaacagc ttgcgtcatg cggtcgctgc   8580
gtatatgatg cgatgagtaa ataaacaaat acgcaagggg aacgcatgaa ggttatcgct   8640
gtacttaacc agaaaggcgg gtcaggcaag acgaccatcg caacccatct agcccgcgcc   8700
ctgcaactcg ccggggccga tgttctgtta gtcgattccg atccccaggg cagtgcccgc   8760
gattgggcgg ccgtgcggga agatcaaccg ctaaccgttg tcggcatcga ccgcccgacg   8820
attgaccgcg acgtgaaggc catcggccgg cgcgacttcg tagtgatcga cggagcgccc   8880
caggcggcgg acttggctgt gtccgcgatc aaggcagccg acttcgtgct gattccggtg   8940
cagccaagcc cttacgacat atgggccacc gccgacctgg tggagctggt taagcagcgc   9000
attgaggtca cggatggaag gctacaagcg gcctttgtcg tgtcgcgggc gatcaaaggc   9060
acgcgcatcg gcggtgaggt tgccgaggcg ctggccgggt acgagctgcc cattcttgag   9120
tcccgtatca cgcagcgcgt gagctaccca ggcactgccg ccgccggcac aaccgttctt   9180
```

```
gaatcagaac ccgagggcga cgctgcccgc gaggtccagg cgctggccgc tgaaattaaa   9240
tcaaaactca tttgagttaa tgaggtaaag agaaaatgag caaaagcaca aacacgctaa   9300
gtgccggccg tccgagcgca cgcagcagca aggctgcaac gttggccagc ctggcagaca   9360
cgccagccat gaagcgggtc aactttcagt tgccggcgga ggatcacacc aagctgaaga   9420
tgtacgcggt acgccaaggc aagaccatta ccgagctgct atctgaatac atcgcgcagc   9480
taccagagta aatgagcaaa tgaataaatg agtagatgaa ttttagcggc taaaggaggc   9540
ggcatggaaa atcaagaaca accaggcacc gacgccgtgg aatgccccat gtgtggagga   9600
acgggcggtt ggccaggcgt aagcggctgg gttgtctgcc ggccctgcaa tggcactgga   9660
acccccaagc ccgaggaatc ggcgtgacgg tcgcaaacca tccggcccgg tacaaatcgg   9720
cgcggcgctg ggtgatgacc tggtggagaa gttgaaggcc gcgcaggccg cccagcggca   9780
acgcatcgag gcagaagcac gccccggtga atcgtggcaa gcggccgctg atcgaatccg   9840
caaagaatcc cggcaaccgc cggcagccgg tgcgccgtcg attaggaagc cgcccaaggg   9900
cgacgagcaa ccagattttt tcgttccgat gctctatgac gtgggcaccc gcgatagtcg   9960
cagcatcatg gacgtggccg ttttccgtct gtcgaagcgt gaccgacgag ctggcgaggt  10020
gatccgctac gagcttccag acgggcacgt agaggtttcc gcagggccgg ccggcatggc  10080
cagtgtgtgg gattacgacc tggtactgat ggcggtttcc catctaaccg aatccatgaa  10140
ccgataccgg gaagggaagg gagacaagcc cggccgcgtg ttccgtccac acgttgcgga  10200
cgtactcaag ttctgccggc gagccgatgg cggaaagcag aaagacgacc tggtagaaac  10260
ctgcattcgg ttaaacacca cgcacgttgc catgcagcgt acgaagaagg ccaagaacgg  10320
ccgcctggtg acggtatccg agggtgaagc cttgattagc cgctacaaga tcgtaaagag  10380
cgaaaccggg cggccggagt acatcgagat cgagctagct gattggatgt accgcgagat  10440
cacagaaggc aagaacccgg acgtgctgac ggttcacccc gattactttt tgatcgatcc  10500
cggcatcggc cgttttctct accgcctggc acgccgcgcc gcaggcaagg cagaagccag  10560
atggttgttc aagacgatct acgaacgcag tggcagcgcc ggagagttca agaagttctg  10620
tttcaccgtg cgcaagctga tcgggtcaaa tgacctgccg gagtacgatt tgaaggagga  10680
ggcggggcag gctggcccga tcctagtcat gcgctaccgc aacctgatcg agggcgaagc  10740
atccgccggt tcctaatgta cggagcagat gctagggcaa attgccctag caggggaaaa  10800
aggtcgaaaa ggtctctttc ctgtggatag cacgtacatt gggaacccaa agccgtacat  10860
tgggaaccgg aacccgtaca ttgggaaccc aaagccgtac attgggaacc ggtcacacat  10920
gtaagtgact gatataaaag agaaaaaagg cgatttttcc gcctaaaact ctttaaaact  10980
tattaaaact cttaaaaccc gcctggcctg tgcataactg tctggccagc gcacagccga  11040
agagctgcaa aaagcgccta cccttcggtc gctgcgctcc ctacgccccg ccgcttcgcg  11100
tcggcctatc gcggccgctg gccgctcaaa aatggctggc ctacggccag gcaatctacc  11160
agggcgcgga caagccgcgc cgtcgccact cgaccgccgg cgcccacatc aaggcaccct  11220
gcctcgcgcg tttcggtgat gacggtgaaa acctctgaca catgcagctc ccggagacgg  11280
tcacagcttg tctgtaagcg gatgccggga gcagacaagc ccgtcagggc gcgtcagcgg  11340
gtgttggcgg gtgtcggggc gcagccatga cccagtcacg tagcgatagc ggagtgtata  11400
ctggcttaac tatgcggcat cagagcagat tgtactgaga gtgcaccata tgcggtgtga  11460
aataccgcac agatgcgtaa ggagaaaata ccgcatcagg cgctcttccg cttcctcgct  11520
cactgactcg ctgcgctcgg tcgttcggct gcggcgagcg gtatcagctc actcaaaggc  11580
```

```
ggtaatacgg ttatccacag aatcagggga taacgcagga aagaacatgt gagcaaaagg  11640

ccagcaaaag gccaggaacc gtaaaaaggc cgcgttgctg gcgtttttcc ataggctccg  11700

cccccctgac gagcatcaca aaaatcgacg ctcaagtcag aggtggcgaa acccgacagg  11760

actataaaga taccaggcgt ttccccctgg aagctccctc gtgcgctctc ctgttccgac  11820

cctgccgctt accggatacc tgtccgcctt tctcccttcg ggaagcgtgg cgctttctca  11880

tagctcacgc tgtaggtatc tcagttcggt gtaggtcgtt cgctccaagc tgggctgtgt  11940

gcacgaaccc cccgttcagc ccgaccgctg cgccttatcc ggtaactatc gtcttgagtc  12000

caacccggta agacacgact tatcgccact ggcagcagcc actggtaaca ggattagcag  12060

agcgaggtat gtaggcggtg ctacagagtt cttgaagtgg tggcctaact acggctacac  12120

tagaaggaca gtatttggta tctgcgctct gctgaagcca gttaccttcg gaaaaagagt  12180

tggtagctct tgatccggca aacaaaccac cgctggtagc ggtggttttt ttgtttgcaa  12240

gcagcagatt acgcgcagaa aaaaaggatc tcaagaagat ccggaaaacg caagcgcaaa  12300

gagaaagcag gtagcttgca gtgggcttac atggcgatag ctagactggg cggttttatg  12360

gacagcaagc gaaccggaat tgcc                                          12384
```

<210> SEQ ID NO 31
<211> LENGTH: 12348
<212> TYPE: DNA
<213> ORGANISM: Artificial
<220> FEATURE:
<223> OTHER INFORMATION: pTVE 500

<400> SEQUENCE: 31

```
agattcgaag ctcggtcccg tgggtgttct gtcgtctcgt tgtacaacga aatccattcc     60

cattccgcgc tcaagatggc ttcccctcgg cagttcatca gggctaaatc aatctagccg    120

acttgtccgg tgaaatgggc tgcactccaa cagaaacaat caaacaaaca tacacagcga    180

cttattcaca cgcgacaaat tacaacggta tatatcctgc cagtactcgg ccgtcgaccg    240

cggtaccccg gaattaagct tgcatgcctg caggcaattg gccgctgtac catgcatgat    300

ctggatttta gtactggatt ttggttttag gaattagaaa ttttattgat agaagtattt    360

tacaaataca aatacatact aagggtttct tatatgctca acacatgagc gaaaccctat    420

aggaacccta attcccttat ctgggaacta ctcacacatt attatggaga aaatagagag    480

agatagattt gtagagagag actggtgatt tcagcgtgtc caagcttgct agctcactct    540

ttgctatcca agacctgctt gaccggttca ctttgattaa tgtatagatt atactcttgg    600

atgtaacgga tgacagagtt tggaagaaga tattgaactg acattccacg tctgatgaaa    660

agccgcactt tcgtagagga aatatcattg taaataagtt gtttgataat aaggatattt    720

cttctgtgtt catacatgat atcatgggaa agcgagaagg acctaacatc agaaccagtc    780

ctttccacga tcaaacatcc ataattaccc aaaatatggt gcaggtctga atcagcccac    840

acatgaggct cgcccatgga ttcgataaga tcaccgcctg ccaataacat gatttttacg    900

cccatttttt caccatctac agtcatgatt ccacctctct tgatatttat ttcatgattg    960

aaatggtcca agacttttgc tgtccttgta taacttgatt gtaaagattc ccaggcatca   1020

accattaacc aagatgatgt ccgctcgcat gctaattcgc acatgcggac acgatgataa   1080

gctggggcta accctcgctt ttgatagtta tcacttactg gagaaaaata accaccaacc   1140

acttcaaaac gcgtttgctc attgatatca tctaaagcca tttcaaacat tctcaaatgt   1200
```

```
aggtatgtta tgggagaaaa tgatccacaa gcaacgatga tcagaggcag tttttcagga   1260
tcttgtaact ttttcgtcaa tctgtgtaca ggaaattcgt aatcttcaat agttctggct   1320
tgtcttacaa ttgtgtgagg aacttcttcc aaatcagcaa tttggctctt cagtaccccc   1380
aaattcccag tcatcgtaac atcctgtaga gtagcgtcaa ttccattcga ttgcccttca   1440
ctttcctcct ccgatgatac atcccgagat agtggctgga agtcactagt atttaatgga   1500
atatggtcca ttcggttgct tgagttggcg ttttttttcc ttgacgacag ggttttgtaa   1560
atgtcgagat tgaaaggagc atcgatcgaa gaattataat cagctaaaac atatggaact   1620
atgggtccag attttggcat cgtatgtgtt ggatctggcg gtggttgtag ttcttcattt   1680
ggctgtggcg gtttaaaatc gggtgctttg gtgggatcca tggttttggt ttaataagaa   1740
gagaaaagag ttcttttgtt atggctgaag taatagagaa atgagctcga gtcctctcca   1800
aatgaaatga acttccttat atagaggaag ggtcttgcga aggatagtgg gattgtgcgt   1860
catcccttac gtcagtggag atatcacatc aatccacttg ctttgaagac gtggttggaa   1920
cgtcttcttt ttccacgatg ctcctcgtgg gtgggggtcc atctttggga ccactgtcgg   1980
cagaggcatc ttgaacgata gcctttcctt tatcgcaatg atggcatttg taggtgccac   2040
cttccttttc tactgtcctt ttgatgaagt gacagatagc tgggcaatgg aatccgagga   2100
ggtttcccga tattaccctt tgttgaaaag tctcaatagc cctttggtct tctgagactg   2160
tatctttgat attcttggag tagacgagag tgtcgtgctc caccatgttg acgaagattt   2220
tcttcttgtc attgagtcgt aaaagactct gtatgaactg ttcgccagtc ttcacggcga   2280
gttctgttag atcctcgatc tgaatttttg actccatgta tggtgcatat ggcgcgccat   2340
atgcccgggc cctgtacagc ggccgcgtta acgcgtatac tctagagcga tcgcccgggc   2400
cggccattta aatgaattcg agctcggtac ccaaacgcgg ccgcaagcta taacttcgta   2460
tagcatacat tatacgaagt tattcgactc tagaggatcc caattcccat gcatggagtc   2520
aaagattcaa atagaggaca cttctcgaac tcggccgtcg aactcggccg tcgagtacat   2580
ggtcgataag aaaaggcaat ttgtagatgt taattcccat cttgaaagaa atatagttta   2640
aatatttatt gataaaataa caagtcaggt attatagtcc aagcaaaaac ataaatttat   2700
tgatgcaagt ttaaattcag aaatatttca ataactgatt atatcagctg gtacattgcc   2760
gtagatgaaa gactgagtgc gatattatgt gtaatacata aattgatgat atagctagct   2820
tagctcatcg gggggatccta gacgcgtgag atcagatctc ggtgacgggc aggaccggac   2880
ggggcggtac cggcaggctg aagtccagct gccagaaacc cacgtcatgc cagttcccgt   2940
gcttgaagcc ggccgcccgc agcatgccgc ggggggcata tccgagcgcc tcgtgcatgc   3000
gcacgctcgg gtcgttgggc agcccgatga cagcgaccac gctcttgaag ccctgtgcct   3060
ccagggactt cagcaggtgg gtgtagagcg tggagcccag tcccgtccgc tggtggcggg   3120
gggagacgta cacggtcgac tcggccgtcc agtcgtaggc gttgcgtgcc ttccaggggc   3180
ccgcgtaggc gatgccggcg acctcgccgt ccacctcggc gacgagccag ggatagcgct   3240
cccgcagacg gacgaggtcg tccgtccact cctgcggttc ctgcggctcg gtacggaagt   3300
tgaccgtgct tgtctcgatg tagtggttga cgatggtgca gaccgccggc atgtccgcct   3360
cggtggcacg gcggatgtcg gccgggcgtc gttctgggtc cattgttctt ctttactctt   3420
tgtgtgactg aggtttggtc tagtgctttg gtcatctata tataatgata acaacaatga   3480
gaacaagctt tggagtgatc ggagggtcta ggatacatga gattcaagtg gactaggatc   3540
tacaccgttg gattttgagt gtggatatgt gtgaggttaa ttttacttgg taacggccac   3600
```

```
aaaggcctaa ggagaggtgt tgagaccctt atcggcttga accgctggaa taatgccacg   3660
tggaagataa ttccatgaat cttatcgtta tctatgagtg aaattgtgtg atggtggagt   3720
ggtgcttgct cattttactt gcctggtgga cttggccctt tccttatggg gaatttatat   3780
tttacttact atagagcttt catacctttt ttttaccttg gatttagtta atatataatg   3840
gtatgattca tgaataaaaa tgggaaattt ttgaatttgt actgctaaat gcataagatt   3900
aggtgaaact gtggaatata tatttttttc atttaaaagc aaaatttgcc ttttactaga   3960
attataaata tagaaaaata tataacattc aaataaaaat gaaaataaga actttcaaaa   4020
aacagaacta tgtttaatgt gtaaagatta gtcgcacatc aagtcatctg ttacaatatg   4080
ttacaacaag tcataagccc aacaaagtta gcacgtctaa ataaactaaa gagtccacga   4140
aaatattaca aatcataagc ccaacaaagt tattgatcaa aaaaaaaaaa cgcccaacaa   4200
agctaaacaa agtccaaaaa aaacttctca agtctccatc ttcctttatg aacattgaaa   4260
actatacaca aaacaagtca gataaatctc tttctgggcc tgtcttccca acctcctaca   4320
tcacttccct atcggattga atgttttact tgtacctttt ccgttgcaat gatattgata   4380
gtatgtttgt gaaaactaat agggttaaca atcgaagtca tggaatatgg atttggtcca   4440
agattttccg agagctttct agtagaaagc ccatcaccag aaatttacta gtaaaataaa   4500
tcaccaatta ggtttcttat tatgtgccaa attcaatata attatagagg atatttcaaa   4560
tgaaaacgta tgaatgttat tagtaaatgg tcaggtaaga cattaaaaaa atcctacgtc   4620
agatattcaa ctttaaaaat tcgatcagtg tggaattgta caaaaatttg ggatctacta   4680
tatatatata atgctttaca acacttggat ttttttttgg aggctggaat ttttaatcta   4740
catatttgtt ttggccatgc accaactcat tgtttagtgt aatactttga ttttgtcaaa   4800
tatatgtgtt cgtgtatatt tgtataagaa tttctttgac catatacaca cacacatata   4860
tatatatata tatatattat atatcatgca cttttaattg aaaaaataat atatatatat   4920
atagtgcatt ttttctaaca accatatatg ttgcgattga tctgcaaaaa tactgctaga   4980
gtaatgaaaa atataatcta ttgctgaaat tatctcagat gttaagattt tcttaaagta   5040
aattctttca aattttagct aaaagtcttg taataactaa agaataatac acaatctcga   5100
ccacggaaaa aaaacacata ataaatttga atttcgaccg cggtacccgg aattgggtta   5160
taattacctc aggtcgagga attaattcgg tacgtaccta ataacttcgt atagcataca   5220
ttatacgaag ttatatggat ctcgaggcat tacggcatta cggcactcgc gagggtccca   5280
attcgagcat ggagccattt acaattgaat atatcctgcc gccgctgccg ctttgcaccc   5340
ggtggagctt gcatgttggt ttctacgcag aactgagccg gttaggcaga taatttccat   5400
tgagaactga gccatgtgca ccttcccccc aacacggtga gcgacggggc aacggagtga   5460
tccacatggg acttttaaac atcatccgtc ggatggcgtt gcgagagaag cagtcgatcc   5520
gtgagatcag ccgacgcacc gggcaggcgc gcaacacgat cgcaaagtat ttgaacgcag   5580
gtacaatcga gccgacgttc acggtaccgg aacgaccaag caagctagct tagtaaagcc   5640
ctcgctagat tttaatgcgg atgttgcgat tacttcgcca actattgcga taacaagaaa   5700
aagccagcct ttcatgatat atctcccaat ttgtgtaggg cttattatgc acgcttaaaa   5760
ataataaaag cagacttgac ctgatagttt ggctgtgagc aattatgtgc ttagtgcatc   5820
taacgcttga gttaagccgc gccgcgaagc ggcgtcggct tgaacgaatt gttagacatt   5880
atttgccgac taccttggtg atctcgcctt tcacgtagtg gacaaattct tccaactgat   5940
```

-continued

```
ctgcgcgcga ggccaagcga tcttcttctt gtccaagata agcctgtcta gcttcaagta   6000
tgacgggctg atactgggcc ggcaggcgct ccattgccca gtcggcagcg acatccttcg   6060
gcgcgatttt gccggttact gcgctgtacc aaatgcggga caacgtaagc actacatttc   6120
gctcatcgcc agcccagtcg ggcggcgagt tccatagcgt taaggtttca tttagcgcct   6180
caaatagatc ctgttcagga accggatcaa agagttcctc cgccgctgga cctaccaagg   6240
caacgctatg ttctcttgct tttgtcagca agatagccag atcaatgtcg atcgtggctg   6300
gctcgaagat acctgcaaga atgtcattgc gctgccattc tccaaattgc agttcgcgct   6360
tagctggata acgccacgga atgatgtcgt cgtgcacaac aatggtgact tctacagcgc   6420
ggagaatctc gctctctcca ggggaagccg aagtttccaa aaggtcgttg atcaaagctc   6480
gccgcgttgt ttcatcaagc cttacggtca ccgtaaccag caaatcaata tcactgtgtg   6540
gcttcaggcc gccatccact gcggagccgt acaaatgtac ggccagcaac gtcggttcga   6600
gatggcgctc gatgacgcca actacctctg atagttgagt cgatacttcg gcgatcaccg   6660
cttccctcat gatgtttaac tttgttttag ggcgactgcc ctgctgcgta acatcgttgc   6720
tgctccataa catcaaacat cgacccacgg cgtaacgcgc ttgctgcttg gatgcccgag   6780
gcatagactg taccccaaaa aaacagtcat aacaagccat gaaaaccgcc actgcgccgt   6840
taccaccgct gcgttcggtc aaggttctgg accagttgcg tgagcgcata cgctacttgc   6900
attacagctt acgaaccgaa caggcttatg tccactgggt tcgtgccttc atccgtttcc   6960
acggtgtgcg tcacccggca accttgggca gcagcgaagt cgaggcattt ctgtcctggc   7020
tggcgaacga gcgcaaggtt tcggtctcca cgcatcgtca ggcattggcg gccttgctgt   7080
tcttctacgg caagtgctgt gcacggatct gccctggctt caggagatcg gaagacctcg   7140
gccgtccggg cgcttgccgg tggtgctgac cccggatgaa gtctctagag ctctagaggg   7200
ttcgcatcct cggttttctg gaaggcgagc atcgtttgtt cgcccagctt ctgtatggaa   7260
cgggcatgcg gatcagtgag ggtttgcaac tgcgggtcaa ggatctggat ttcgatcacg   7320
gcacgatcat cgtgcgggag ggcaagggct ccaaggatcg ggccttgatg ttacccgaga   7380
gcttggcacc cagcctgcgc gagcagggat cgatccaacc cctccgctgc tatagtgcag   7440
tcggcttctg acgttcagtg cagccgtctt ctgaaaacga catgtcgcac aagtcctaag   7500
ttacgcgaca ggctgccgcc ctgccctttt cctggcgttt tcttgtcgcg tgttttagtc   7560
gcataaagta gaatacttgc gactagaacc ggagacatta cgccatgaac aagagcgccg   7620
ccgctggcct gctgggctat gcccgcgtca gcaccgacga ccaggacttg accaaccaac   7680
gggccgaact gcacgcggcc ggctgcacca agctgttttc cgagaagatc accggcacca   7740
ggcgcgaccg cccggagctg gccaggatgc ttgaccacct acgccctggc gacgttgtga   7800
cagtgaccag gctagaccgc ctggcccgca gcacccgcga cctactggac attgccgagc   7860
gcatccagga ggccggcgcg ggcctgcgta gcctggcaga gccgtgggcc gacaccacca   7920
cgccggccgg ccgcatggtg ttgaccgtgt tcgccggcat tgccgagttc gagcgttccc   7980
taatcatcga ccgcacccgg agcgggcgcg aggccgccaa ggcccgaggc gtgaagtttg   8040
gcccccgccc taccctcacc ccggcacaga tcgcgcacgc ccgcgagctg atcgaccagg   8100
aaggccgcac cgtgaaagag gcggctgcac tgcttggcgt gcatcgctcg accctgtacc   8160
gcgcacttga gcgcagcgag gaagtgacgc ccaccgaggc caggcggcgc ggtgccttcc   8220
gtgaggacgc attgaccgag gccgacgccc tggcggccgc cgagaatgaa cgccaagagg   8280
aacaagcatg aaaccgcacc aggacggcca ggacgaaccg tttttcatta ccgaagagat   8340
```

```
cgaggcggag atgatcgcgg ccgggtacgt gttcgagccg cccgcgcacg tctcaaccgt   8400
gcggctgcat gaaatcctgg ccggtttgtc tgatgccaag ctggcggcct ggccggccag   8460
cttggccgct gaagaaaccg agcgccgccg tctaaaaagg tgatgtgtat ttgagtaaaa   8520
cagcttgcgt catgcggtcg ctgcgtatat gatgcgatga gtaaataaac aaatacgcaa   8580
ggggaacgca tgaaggttat cgctgtactt aaccagaaag gcgggtcagg caagacgacc   8640
atcgcaaccc atctagcccg cgccctgcaa ctcgccgggg ccgatgttct gttagtcgat   8700
tccgatcccc agggcagtgc ccgcgattgg gcggccgtgc gggaagatca accgctaacc   8760
gttgtcggca tcgaccgccc gacgattgac cgcgacgtga aggccatcgg ccggcgcgac   8820
ttcgtagtga tcgacggagc gccccaggcg gcggacttgg ctgtgtccgc gatcaaggca   8880
gccgacttcg tgctgattcc ggtgcagcca agcccttacg acatatgggc caccgccgac   8940
ctggtggagc tggttaagca gcgcattgag gtcacggatg gaaggctaca agcggccttt   9000
gtcgtgtcgc gggcgatcaa aggcacgcgc atcggcggtg aggttgccga ggcgctggcc   9060
gggtacgagc tgcccattct tgagtcccgt atcacgcagc gcgtgagcta cccaggcact   9120
gccgccgccg gcacaaccgt tcttgaatca gaacccgagg gcgacgctgc ccgcgaggtc   9180
caggcgctgg ccgctgaaat taaatcaaaa ctcatttgag ttaatgaggt aaagagaaaa   9240
tgagcaaaag cacaaacacg ctaagtgccg gccgtccgag cgcacgcagc agcaaggctg   9300
caacgttggc cagcctggca gacacgccag ccatgaagcg ggtcaacttt cagttgccgg   9360
cggaggatca caccaagctg aagatgtacg cggtacgcca aggcaagacc attaccgagc   9420
tgctatctga atacatcgcg cagctaccag agtaaatgag caaatgaata aatgagtaga   9480
tgaattttag cggctaaagg aggcggcatg gaaaatcaag aacaaccagg caccgacgcc   9540
gtggaatgcc ccatgtgtgg aggaacgggc ggttggccag gcgtaagcgg ctgggttgtc   9600
tgccggccct gcaatggcac tggaaccccc aagcccgagg aatcggcgtg acggtcgcaa   9660
accatccggc ccggtacaaa tcggcgcggc gctgggtgat gacctggtgg agaagttgaa   9720
ggccgcgcag gccgcccagc ggcaacgcat cgaggcagaa gcacgccccg gtgaatcgtg   9780
gcaagcggcc gctgatcgaa tccgcaaaga atcccggcaa ccgccggcag ccggtgcgcc   9840
gtcgattagg aagccgccca agggcgacga gcaaccagat tttttcgttc cgatgctcta   9900
tgacgtgggc acccgcgata gtcgcagcat catggacgtg gccgttttcc gtctgtcgaa   9960
gcgtgaccga cgagctggcg aggtgatccg ctacgagctt ccagacgggc acgtagaggt  10020
ttccgcaggg ccggccggca tggccagtgt gtgggattac gacctggtac tgatggcggt  10080
ttcccatcta accgaatcca tgaaccgata ccgggaaggg aagggagaca agcccggccg  10140
cgtgttccgt ccacacgttg cggacgtact caagttctgc cggcgagccg atggcggaaa  10200
gcagaaagac gacctggtag aaacctgcat tcggttaaac accacgcacg ttgccatgca  10260
gcgtacgaag aaggccaaga acggccgcct ggtgacggta tccgagggtg aagccttgat  10320
tagccgctac aagatcgtaa agagcgaaac cgggcggccg gagtacatcg agatcgagct  10380
agctgattgg atgtaccgcg agatcacaga aggcaagaac ccggacgtgc tgacggttca  10440
ccccgattac tttttgatcg atcccggcat cggccgtttt ctctaccgcc tggcacgccg  10500
cgccgcaggc aaggcagaag ccagatggtt gttcaagacg atctacgaac gcagtggcag  10560
cgccggagag ttcaagaagt tctgtttcac cgtgcgcaag ctgatcgggt caaatgacct  10620
gccggagtac gatttgaagg aggaggcggg gcaggctggc ccgatcctag tcatgcgcta  10680
```

```
ccgcaacctg atcgagggcg aagcatccgc cggttcctaa tgtacggagc agatgctagg  10740
gcaaattgcc ctagcagggg aaaaaggtcg aaaaggtctc tttcctgtgg atagcacgta  10800
cattgggaac ccaaagccgt acattgggaa ccggaacccg tacattggga acccaaagcc  10860
gtacattggg aaccggtcac acatgtaagt gactgatata aaagagaaaa aaggcgattt  10920
ttccgcctaa aactctttaa aacttattaa aactcttaaa acccgcctgg cctgtgcata  10980
actgtctggc cagcgcacag ccgaagagct gcaaaaagcg cctacccttc ggtcgctgcg  11040
ctccctacgc cccgccgctt cgcgtcggcc tatcgcggcc gctggccgct caaaaatggc  11100
tggcctacgg ccaggcaatc taccagggcg cggacaagcc gcgccgtcgc cactcgaccg  11160
ccggcgccca catcaaggca ccctgcctcg cgcgtttcgg tgatgacggt gaaaacctct  11220
gacacatgca gctcccggag acggtcacag cttgtctgta agcggatgcc gggagcagac  11280
aagcccgtca gggcgcgtca gcgggtgttg gcgggtgtcg gggcgcagcc atgacccagt  11340
cacgtagcga tagcggagtg tatactggct taactatgcg gcatcagagc agattgtact  11400
gagagtgcac catatgcggt gtgaaatacc gcacagatgc gtaaggagaa aataccgcat  11460
caggcgctct tccgcttcct cgctcactga ctcgctgcgc tcggtcgttc ggctgcggcg  11520
agcggtatca gctcactcaa aggcggtaat acggttatcc acagaatcag gggataacgc  11580
aggaaagaac atgtgagcaa aaggccagca aaaggccagg aaccgtaaaa aggccgcgtt  11640
gctggcgttt ttccataggc tccgcccccc tgacgagcat cacaaaaatc gacgctcaag  11700
tcagaggtgg cgaaacccga caggactata aagataccag gcgtttcccc ctggaagctc  11760
cctcgtgcgc tctcctgttc cgaccctgcc gcttaccgga tacctgtccg cctttctccc  11820
ttcgggaagc gtggcgcttt ctcatagctc acgctgtagg tatctcagtt cggtgtaggt  11880
cgttcgctcc aagctgggct gtgtgcacga accccccgtt cagcccgacc gctgcgcctt  11940
atccggtaac tatcgtcttg agtccaaccc ggtaagacac gacttatcgc cactggcagc  12000
agccactggt aacaggatta gcagagcgag gtatgtaggc ggtgctacag agttcttgaa  12060
gtggtggcct aactacggct acactagaag gacagtattt ggtatctgcg ctctgctgaa  12120
gccagttacc ttcggaaaaa gagttggtag ctcttgatcc ggcaaacaaa ccaccgctgg  12180
tagcggtggt ttttttgttt gcaagcagca gattacgcgc agaaaaaaag gatctcaaga  12240
agatccggaa aacgcaagcg caaagagaaa gcaggtagct tgcagtgggc ttacatggcg  12300
atagctagac tgggcggttt tatggacagc aagcgaaccg gaattgcc              12348
```

<210> SEQ ID NO 32
<211> LENGTH: 12366
<212> TYPE: DNA
<213> ORGANISM: Artificial
<220> FEATURE:
<223> OTHER INFORMATION: pTVE 501

<400> SEQUENCE: 32

```
agattcgaag ctcggtcccg tgggtgttct gtcgtctcgt tgtacaacga aatccattcc     60
cattccgcgc tcaagatggc ttcccctcgg cagttcatca gggctaaatc aatctagccg    120
acttgtccgg tgaaatgggc tgcactccaa cagaaacaat caaacaaaca tacacagcga    180
cttattcaca cgcgacaaat tacaacggta tatatcctgc cagtactcgg ccgtcgaccg    240
cggtaccccg gaattaagct tgcatgcctg caggcaattg gccgctgtac catgcatgat    300
ctggatttta gtactggatt ttggttttag gaattagaaa ttttattgat agaagtattt    360
tacaaataca aatacatact aagggtttct tatatgctca acacatgagc gaaaccctat    420
```

```
aggaacccta attcccttat ctgggaacta ctcacacatt attatggaga aaatagagag    480
agatagattt gtagagagag actggtgatt tcagcgtgtc caagcttgct agctcactct    540
ttgctatcca agacctgctt gaccggttca ctttgattaa tgtatagatt atactcttgg    600
atgtaacgga tgacagagtt tggaagaaga tattgaactg acattccacg tctgatgaaa    660
agccgcactt tcgtagagga aatatcattg taaataagtt gtttgataat aaggatattt    720
cttctgtgtt catacatgat atcatgggaa agcgagaagg acctaacatc agaaccagtc    780
ctttccacga tcaaacatcc ataattaccc aaaatatggt gcaggtctga atcagcccac    840
acatgaggct cgcccatgga ttcgataaga tcaccgcctg ccaataacat gatttttacg    900
cccatttttt caccatctac agtcatgatt ccacctctct tgatatttat ttcatgattg    960
aaatggtcca agacttttgc tgtccttgta taacttgatt gtaaagattc ccaggcatca   1020
accattaacc aagatgatgt ccgctcgcat gctaattcgc acatgcggac acgatgataa   1080
gctggggcta accctcgctt ttgatagtta tcacttactg gagaaaaata accaccaacc   1140
acttcaaaac gcgtttgctc attgatatca tctaaagcca tttcaaacat tctcaaatgt   1200
aggtatgtta tgggagaaaa tgatccacaa gcaacgatga tcagaggcag tttttcagga   1260
tcttgtaact ttttcgtcaa tctgtgtaca ggaaattcgt aatcttcaat agttctggct   1320
tgtcttacaa ttgtgtgagg aacttcttcc aaatcagcaa tttggctctt cagtaccccc   1380
aaattcccag tcatcgtaac atcctgtaga gtagcgtcaa ttccattcga ttgcccttca   1440
ctttcctcct ccgatgatac atcccgagat agtggctgga agtcactagt atttaatgga   1500
atatggtcca ttcggttgct tgagttggcg tttttttcc ttgacgacag ggttttgtaa    1560
atgtcgagat tgaaaggagc atcgatcgaa gaattataat cagctaaaac atatggaact   1620
atgggtccag attttggcat cgtatgtgtt ggatctggcg gtggttgtag ttcttcattt   1680
ggctgtggcg gtttaaaatc gggtgctttg gtaaccttgc gcttcttctt gggatccatg   1740
gttttggttt aataagaaga gaaaagagtt cttttgttat ggctgaagta atagagaaat   1800
gagctcgagt cctctccaaa tgaaatgaac ttccttatat agaggaaggg tcttgcgaag   1860
gatagtggga ttgtgcgtca tcccttacgt cagtggagat atcacatcaa tccacttgct   1920
ttgaagacgt ggttggaacg tcttcttttt ccacgatgct cctcgtgggt gggggtccat   1980
ctttgggacc actgtcggca gaggcatctt gaacgatagc ctttccttta tcgcaatgat   2040
ggcatttgta ggtgccacct tccttttcta ctgtcctttt gatgaagtga cagatagctg   2100
ggcaatggaa tccgaggagg tttcccgata ttaccctttg ttgaaaagtc tcaatagccc   2160
tttggtcttc tgagactgta tctttgatat tcttggagta gacgagagtg tcgtgctcca   2220
ccatgttgac gaagattttc ttcttgtcat tgagtcgtaa aagactctgt atgaactgtt   2280
cgccagtctt cacggcgagt tctgttagat cctcgatctg aatttttgac tccatgtatg   2340
gtgcatatgg cgcgccatat gcccgggccc tgtacagcgg ccgcgttaac gcgtatactc   2400
tagagcgatc gcccgggccg gccatttaaa tgaattcgag ctcggtaccc aaacgcggcc   2460
gcaagctata acttcgtata gcatacatta tacgaagtta ttcgactcta gaggatccca   2520
attcccatgc atggagtcaa agattcaaat agaggacact tctcgaactc ggccgtcgaa   2580
ctcggccgtc gagtacatgg tcgataagaa aaggcaattt gtagatgtta attcccatct   2640
tgaaagaaat atagtttaaa tatttattga taaaataaca agtcaggtat tatagtccaa   2700
gcaaaaacat aaatttattg atgcaagttt aaattcagaa atatttcaat aactgattat   2760
```

```
atcagctggt acattgccgt agatgaaaga ctgagtgcga tattatgtgt aatacataaa   2820
ttgatgatat agctagctta gctcatcggg ggatcctaga cgcgtgagat cagatctcgg   2880
tgacgggcag gaccggacgg ggcggtaccg gcaggctgaa gtccagctgc cagaaaccca   2940
cgtcatgcca gttcccgtgc ttgaagccgg ccgcccgcag catgccgcgg ggggcatatc   3000
cgagcgcctc gtgcatgcgc acgctcgggt cgttgggcag cccgatgaca gcgaccacgc   3060
tcttgaagcc ctgtgcctcc agggacttca gcaggtgggt gtagagcgtg gagcccagtc   3120
ccgtccgctg gtggcggggg gagacgtaca cggtcgactc ggccgtccag tcgtaggcgt   3180
tgcgtgcctt ccaggggccc gcgtaggcga tgccggcgac ctcgccgtcc acctcggcga   3240
cgagccaggg atagcgctcc cgcagacgga cgaggtcgtc cgtccactcc tgcggttcct   3300
gcggctcggt acggaagttg accgtgcttg tctcgatgta gtggttgacg atggtgcaga   3360
ccgccggcat gtccgcctcg gtggcacggc ggatgtcggc cgggcgtcgt tctgggtcca   3420
ttgttcttct ttactctttg tgtgactgag gtttggtcta gtgctttggt catctatata   3480
taatgataac aacaatgaga acaagctttg gagtgatcgg agggtctagg atacatgaga   3540
ttcaagtgga ctaggatcta caccgttgga ttttgagtgt ggatatgtgt gaggttaatt   3600
ttacttggta acggccacaa aggcctaagg agaggtgttg agacccttat cggcttgaac   3660
cgctggaata atgccacgtg gaagataatt ccatgaatct tatcgttatc tatgagtgaa   3720
attgtgtgat ggtggagtgg tgcttgctca ttttacttgc ctggtggact tggccctttc   3780
cttatgggga atttatattt tacttactat agagctttca tacctttttt ttaccttgga   3840
tttagttaat atataatggt atgattcatg aataaaaatg ggaaattttt gaatttgtac   3900
tgctaaatgc ataagattag gtgaaactgt ggaatatata tttttttcat ttaaaagcaa   3960
aatttgcctt ttactagaat tataaatata gaaaaatata taacattcaa ataaaaatga   4020
aaataagaac tttcaaaaaa cagaactatg tttaatgtgt aaagattagt cgcacatcaa   4080
gtcatctgtt acaatatgtt acaacaagtc ataagcccaa caaagttagc acgtctaaat   4140
aaactaaaga gtccacgaaa atattacaaa tcataagccc aacaaagtta ttgatcaaaa   4200
aaaaaaaacg cccaacaaag ctaaacaaag tccaaaaaaa acttctcaag tctccatctt   4260
cctttatgaa cattgaaaac tatacacaaa acaagtcaga taaatctctt tctgggcctg   4320
tcttcccaac ctcctacatc acttccctat cggattgaat gttttacttg taccttttcc   4380
gttgcaatga tattgatagt atgtttgtga aaactaatag ggttaacaat cgaagtcatg   4440
gaatatggat ttggtccaag attttccgag agctttctag tagaaagccc atcaccagaa   4500
atttactagt aaaataaatc accaattagg tttcttatta tgtgccaaat tcaatataat   4560
tatagaggat atttcaaatg aaaacgtatg aatgttatta gtaaatggtc aggtaagaca   4620
ttaaaaaaat cctacgtcag atattcaact ttaaaaattc gatcagtgtg gaattgtaca   4680
aaaatttggg atctactata tatatataat gctttacaac acttggattt ttttttggag   4740
gctggaattt ttaatctaca tatttgtttt ggccatgcac caactcattg tttagtgtaa   4800
tactttgatt ttgtcaaata tatgtgttcg tgtatatttg tataagaatt tctttgacca   4860
tatacacaca cacatatata tatatatata tatattatat atcatgcact tttaattgaa   4920
aaaataatat atatatatat agtgcatttt ttctaacaac catatatgtt gcgattgatc   4980
tgcaaaaata ctgctagagt aatgaaaaat ataatctatt gctgaaatta tctcagatgt   5040
taagattttc ttaaagtaaa ttctttcaaa ttttagctaa aagtcttgta ataactaaag   5100
aataatacac aatctcgacc acggaaaaaa aacacataat aaatttgaat ttcgaccgcg   5160
```

```
gtacccggaa ttgggttata attacctcag gtcgaggaat taattcggta cgtacctaat   5220
aacttcgtat agcatacatt atacgaagtt atatggatct cgaggcatta cggcattacg   5280
gcactcgcga gggtcccaat tcgagcatgg agccatttac aattgaatat atcctgccgc   5340
cgctgccgct ttgcacccgg tggagcttgc atgttggttt ctacgcagaa ctgagccggt   5400
taggcagata atttccattg agaactgagc catgtgcacc ttccccccaa cacggtgagc   5460
gacggggcaa cggagtgatc cacatgggac ttttaaacat catccgtcgg atggcgttgc   5520
gagagaagca gtcgatccgt gagatcagcc gacgcaccgg gcaggcgcgc aacacgatcg   5580
caaagtattt gaacgcaggt acaatcgagc cgacgttcac ggtaccggaa cgaccaagca   5640
agctagctta gtaaagccct cgctagattt taatgcggat gttgcgatta cttcgccaac   5700
tattgcgata acaagaaaaa gccagccttt catgatatat ctcccaattt gtgtagggct   5760
tattatgcac gcttaaaaat aataaaagca gacttgacct gatagtttgg ctgtgagcaa   5820
ttatgtgctt agtgcatcta acgcttgagt taagccgcgc cgcgaagcgg cgtcggcttg   5880
aacgaattgt tagacattat ttgccgacta ccttggtgat ctcgcctttc acgtagtgga   5940
caaattcttc caactgatct gcgcgcgagg ccaagcgatc ttcttcttgt ccaagataag   6000
cctgtctagc ttcaagtatg acgggctgat actgggccgg caggcgctcc attgcccagt   6060
cggcagcgac atccttcggc gcgattttgc cggttactgc gctgtaccaa atgcgggaca   6120
acgtaagcac tacatttcgc tcatcgccag cccagtcggg cggcgagttc catagcgtta   6180
aggtttcatt tagcgcctca aatagatcct gttcaggaac cggatcaaag agttcctccg   6240
ccgctggacc taccaaggca acgctatgtt ctcttgcttt tgtcagcaag atagccagat   6300
caatgtcgat cgtggctggc tcgaagatac ctgcaagaat gtcattgcgc tgccattctc   6360
caaattgcag ttcgcgctta gctggataac gccacggaat gatgtcgtcg tgcacaacaa   6420
tggtgacttc tacagcgcgg agaatctcgc tctctccagg ggaagccgaa gtttccaaaa   6480
ggtcgttgat caaagctcgc cgcgttgttt catcaagcct tacggtcacc gtaaccagca   6540
aatcaatatc actgtgtggc ttcaggccgc catccactgc ggagccgtac aaatgtacgg   6600
ccagcaacgt cggttcgaga tggcgctcga tgacgccaac tacctctgat agttgagtcg   6660
atacttcggc gatcaccgct tccctcatga tgtttaactt tgttttaggg cgactgccct   6720
gctgcgtaac atcgttgctg ctccataaca tcaaacatcg acccacggcg taacgcgctt   6780
gctgcttgga tgcccgaggc atagactgta ccccaaaaaa acagtcataa caagccatga   6840
aaaccgccac tgcgccgtta ccaccgctgc gttcggtcaa ggttctggac cagttgcgtg   6900
agcgcatacg ctacttgcat tacagcttac gaaccgaaca ggcttatgtc cactgggttc   6960
gtgccttcat ccgtttccac ggtgtgcgtc acccggcaac cttgggcagc agcgaagtcg   7020
aggcatttct gtcctggctg gcgaacgagc gcaaggtttc ggtctccacg catcgtcagg   7080
cattggcggc cttgctgttc ttctacggca agtgctgtgc acggatctgc cctggcttca   7140
ggagatcgga agacctcggc cgtccgggcg cttgccggtg gtgctgaccc cggatgaagt   7200
ctctagagct ctagagggtt cgcatcctcg gttttctgga aggcgagcat cgtttgttcg   7260
cccagcttct gtatggaacg ggcatgcgga tcagtgaggg tttgcaactg cgggtcaagg   7320
atctggattt cgatcacggc acgatcatcg tgcgggaggg caagggctcc aaggatcggg   7380
ccttgatgtt acccgagagc ttggcaccca gcctgcgcga gcagggatcg atccaacccc   7440
tccgctgcta tagtgcagtc ggcttctgac gttcagtgca gccgtcttct gaaaacgaca   7500
```

```
tgtcgcacaa gtcctaagtt acgcgacagg ctgccgccct gccctttcc tggcgttttc    7560
ttgtcgcgtg ttttagtcgc ataaagtaga atacttgcga ctagaaccgg agacattacg    7620
ccatgaacaa gagcgccgcc gctggcctgc tgggctatgc ccgcgtcagc accgacgacc    7680
aggacttgac caaccaacgg gccgaactgc acgcggccgg ctgcaccaag ctgttttccg    7740
agaagatcac cggcaccagg cgcgaccgcc cggagctggc caggatgctt gaccacctac    7800
gccctggcga cgttgtgaca gtgaccaggc tagaccgcct ggcccgcagc acccgcgacc    7860
tactggacat tgccgagcgc atccaggagg ccggcgcggg cctgcgtagc ctggcagagc    7920
cgtgggccga caccaccacg ccggccggcc gcatggtgtt gaccgtgttc gccggcattg    7980
ccgagttcga gcgttcccta atcatcgacc gcacccggag cgggcgcgag gccgccaagg    8040
cccgaggcgt gaagtttggc ccccgcccta ccctcacccc ggcacagatc gcgcacgccc    8100
gcgagctgat cgaccaggaa ggccgcaccg tgaaagaggc ggctgcactg cttggcgtgc    8160
atcgctcgac cctgtaccgc gcacttgagc gcagcgagga agtgacgccc accgaggcca    8220
ggcggcgcgg tgccttccgt gaggacgcat tgaccgaggc cgacgccctg gcggccgccg    8280
agaatgaacg ccaagaggaa caagcatgaa accgcaccag gacggccagg acgaaccgtt    8340
tttcattacc gaagagatcg aggcggagat gatcgcggcc gggtacgtgt tcgagccgcc    8400
cgcgcacgtc tcaaccgtgc ggctgcatga aatcctggcc ggtttgtctg atgccaagct    8460
ggcggcctgg ccggccagct tggccgctga agaaaccgag cgccgccgtc taaaaaggtg    8520
atgtgtattt gagtaaaaca gcttgcgtca tgcggtcgct gcgtatatga tgcgatgagt    8580
aaataaacaa atacgcaagg ggaacgcatg aaggttatcg ctgtacttaa ccagaaaggc    8640
gggtcaggca agacgaccat cgcaacccat ctagcccgcg ccctgcaact cgccggggcc    8700
gatgttctgt tagtcgattc cgatccccag ggcagtgccc gcgattgggc ggccgtgcgg    8760
gaagatcaac cgctaaccgt tgtcggcatc gaccgcccga cgattgaccg cgacgtgaag    8820
gccatcggcc ggcgcgactt cgtagtgatc gacggagcgc cccaggcggc ggacttggct    8880
gtgtccgcga tcaaggcagc cgacttcgtg ctgattccgg tgcagccaag cccttacgac    8940
atatgggcca ccgccgacct ggtggagctg gttaagcagc gcattgaggt cacggatgga    9000
aggctacaag cggcctttgt cgtgtcgcgg gcgatcaaag gcacgcgcat cggcggtgag    9060
gttgccgagg cgctggccgg gtacgagctg cccattcttg agtcccgtat cacgcagcgc    9120
gtgagctacc caggcactgc cgccgccggc acaaccgttc ttgaatcaga acccgagggc    9180
gacgctgccc gcgaggtcca ggcgctggcc gctgaaatta aatcaaaact catttgagtt    9240
aatgaggtaa agagaaaatg agcaaaagca caaacacgct aagtgccggc cgtccgagcg    9300
cacgcagcag caaggctgca acgttggcca gcctggcaga cacgccagcc atgaagcggg    9360
tcaactttca gttgccggcg gaggatcaca ccaagctgaa gatgtacgcg gtacgccaag    9420
gcaagaccat taccgagctg ctatctgaat acatcgcgca gctaccagag taaatgagca    9480
aatgaataaa tgagtagatg aattttagcg gctaaaggag gcggcatgga aaatcaagaa    9540
caaccaggca ccgacgccgt ggaatgcccc atgtgtggag gaacgggcgg ttggccaggc    9600
gtaagcggct gggttgtctg ccggccctgc aatggcactg gaacccccaa gcccgaggaa    9660
tcggcgtgac ggtcgcaaac catccggccc ggtacaaatc ggcgcggcgc tgggtgatga    9720
cctggtggag aagttgaagg ccgcgcaggc cgcccagcgg caacgcatcg aggcagaagc    9780
acgccccggt gaatcgtggc aagcggccgc tgatcgaatc cgcaaagaat cccggcaacc    9840
gccggcagcc ggtgcgccgt cgattaggaa gccgcccaag ggcgacgagc aaccagattt    9900
```

```
tttcgttccg atgctctatg acgtgggcac ccgcgatagt cgcagcatca tggacgtggc   9960
cgttttccgt ctgtcgaagc gtgaccgacg agctggcgag gtgatccgct acgagcttcc  10020
agacgggcac gtagaggttt ccgcagggcc ggccggcatg gccagtgtgt gggattacga  10080
cctggtactg atggcggttt cccatctaac cgaatccatg aaccgatacc gggaagggaa  10140
gggagacaag cccggccgcg tgttccgtcc acacgttgcg gacgtactca agttctgccg  10200
gcgagccgat ggcggaaagc agaaagacga cctggtagaa acctgcattc ggttaaacac  10260
cacgcacgtt gccatgcagc gtacgaagaa ggccaagaac ggccgcctgg tgacggtatc  10320
cgagggtgaa gccttgatta gccgctacaa gatcgtaaag agcgaaaccg ggcggccgga  10380
gtacatcgag atcgagctag ctgattggat gtaccgcgag atcacagaag gcaagaaccc  10440
ggacgtgctg acggttcacc ccgattactt tttgatcgat cccggcatcg gccgttttct  10500
ctaccgcctg gcacgccgcg ccgcaggcaa ggcagaagcc agatggttgt tcaagacgat  10560
ctacgaacgc agtggcagcg ccggagagtt caagaagttc tgtttcaccg tgcgcaagct  10620
gatcgggtca aatgacctgc cggagtacga tttgaaggag gaggcggggc aggctggccc  10680
gatcctagtc atgcgctacc gcaacctgat cgagggcgaa gcatccgccg gttcctaatg  10740
tacggagcag atgctagggc aaattgccct agcaggggaa aaaggtcgaa aaggtctctt  10800
tcctgtggat agcacgtaca ttgggaaccc aaagccgtac attgggaacc ggaacccgta  10860
cattgggaac ccaaagccgt acattgggaa ccggtcacac atgtaagtga ctgatataaa  10920
agagaaaaaa ggcgattttt ccgcctaaaa ctctttaaaa cttattaaaa ctcttaaaac  10980
ccgcctggcc tgtgcataac tgtctggcca gcgcacagcc gaagagctgc aaaaagcgcc  11040
tacccttcgg tcgctgcgct ccctacgccc cgccgcttcg cgtcggccta tcgcggccgc  11100
tggccgctca aaaatggctg gcctacggcc aggcaatcta ccagggcgcg gacaagccgc  11160
gccgtcgcca ctcgaccgcc ggcgcccaca tcaaggcacc ctgcctcgcg cgtttcggtg  11220
atgacggtga aaacctctga cacatgcagc tcccggagac ggtcacagct tgtctgtaag  11280
cggatgccgg gagcagacaa gcccgtcagg gcgcgtcagc gggtgttggc gggtgtcggg  11340
gcgcagccat gacccagtca cgtagcgata gcggagtgta tactggctta actatgcggc  11400
atcagagcag attgtactga gagtgcacca tatgcggtgt gaaataccgc acagatgcgt  11460
aaggagaaaa taccgcatca ggcgctcttc cgcttcctcg ctcactgact cgctgcgctc  11520
ggtcgttcgg ctgcggcgag cggtatcagc tcactcaaag gcggtaatac ggttatccac  11580
agaatcaggg gataacgcag gaaagaacat gtgagcaaaa ggccagcaaa aggccaggaa  11640
ccgtaaaaag gccgcgttgc tggcgttttt ccataggctc cgcccccctg acgagcatca  11700
caaaaatcga cgctcaagtc agaggtggcg aaacccgaca ggactataaa gataccaggc  11760
gtttccccct ggaagctccc tcgtgcgctc tcctgttccg accctgccgc ttaccggata  11820
cctgtccgcc tttctccctt cgggaagcgt ggcgctttct catagctcac gctgtaggta  11880
tctcagttcg gtgtaggtcg ttcgctccaa gctgggctgt gtgcacgaac cccccgttca  11940
gcccgaccgc tgcgccttat ccggtaacta tcgtcttgag tccaacccgg taagacacga  12000
cttatcgcca ctggcagcag ccactggtaa caggattagc agagcgaggt atgtaggcgg  12060
tgctacagag ttcttgaagt ggtggcctaa ctacggctac actagaagga cagtatttgg  12120
tatctgcgct ctgctgaagc cagttacctt cggaaaaaga gttggtagct cttgatccgg  12180
caaacaaacc accgctggta gcggtggttt ttttgtttgc aagcagcaga ttacgcgcag  12240
```

aaaaaaagga tctcaagaag atccggaaaa cgcaagcgca aagagaaagc aggtagcttg 12300
cagtgggctt acatggcgat agctagactg ggcggtttta tggacagcaa gcgaaccgga 12360
attgcc 12366

<210> SEQ ID NO 33
<211> LENGTH: 13305
<212> TYPE: DNA
<213> ORGANISM: Artificial
<220> FEATURE:
<223> OTHER INFORMATION: pTVE502

<400> SEQUENCE: 33
agattcgaag ctcggtcccg tgggtgttct gtcgtctcgt tgtacaacga aatccattcc 60
cattccgcgc tcaagatggc ttcccctcgg cagttcatca gggctaaatc aatctagccg 120
acttgtccgg tgaaatgggc tgcactccaa cagaaacaat caaacaaaca tacacagcga 180
cttattcaca cgcgacaaat tacaacggta tatatcctgc cagtactcgg ccgtcgaccg 240
cggtaccccg gaattaagct tgcatgcctg caggcaattg gccgctgtac catgcatgat 300
ctggatttta gtactggatt ttggttttag gaattagaaa ttttattgat agaagtattt 360
tacaaataca aatacatact aagggtttct tatatgctca acacatgagc gaaaccctat 420
aggaacccta attcccttat ctgggaacta ctcacacatt attatggaga aaatagagag 480
agatagattt gtagagagag actggtgatt tcagcgtgtc caagcttgct agcctaatca 540
atagacataa tgtcaagcgt tgagccttta tgtgcttcac actgctcgac aacttcatca 600
atttttcttg aagcccatgg aaatcttggg ttgattaaga aaggacgtaa gtcaaatctg 660
ttgtcttctg gtgaatactg ttcagcatga taactaggag ttaaaacagt ttgcttgtgt 720
ctgttgatgg catagaagaa gaaaaatctt ttcacctttt cagatatttg acgaggtgtt 780
aactttgggg accattgatg aagaagtttt aagaacatag aataaggacc acatttttca 840
acctttctta ggtaaccaaa cacgcccaat tcttcatacg tcatccccat atctatctca 900
tccgattgaa cgtaatcttt agtcataggt tctaattctg cagttggtgt agcgtttaaa 960
aagtcattca agattggcat gttatattgt tttgatgcgt aggcaatgaa tcttttcaag 1020
tcagtttttg aaataccccc aatagggttg atatctgcgg aggagcagtc atattttgtt 1080
agatacccac gtaagcactc atcaacattt gcgctaccaa gtactaacaa tccacccgag 1140
tttgggatac cacgaaccca cggcaacagt tgcgcaaaaa gataagaaag aaccattctt 1200
agacgcgcct ggatgttttg taaagccaag ttctcgattt gagatccccc aaatattttg 1260
tatattggtt ttttgccagt ggctacttcg aataaggaca ccacactgga taccaatgag 1320
tccatcttta aatccacgtg gtaagatcca attgcattgg aaaggtcctt tgctctgttt 1380
cttgtctcct tggatgaatt ttccgtaccc atgaaacagg agtgaaatat ttttgaggct 1440
agatcctgtg gactgtctgg aatccaatca tcgccgctac gtgttatctt acgaacgtct 1500
ttgataactt gctcatttcc attttgagca gcgtcggtca ctaaacggca catagagtgg 1560
acaatcattg cagttgcaca agagtcaatg cccccagata agggaaggaa aaaccctgtt 1620
ccgttacaac gtcttaaata atcccacatc cagcaagcag gtcccagtgc aatttcttcc 1680
tcaggagagt gatagaaagg ctcgcggact tttgttggac acactgtagg atcaaatctg 1740
gaggtcatta aagccaattc tacaggaata tcaatacgct tgaactttat ttctgccaag 1800
gaggcttgta ggccacgaga catgacagct gcacgataac tcctcacctc ttctaggtcc 1860
acagtagcag taactacttc cacatcatct agcgaaaatt gtgaaccttg ggctacaatt 1920

```
gtaccattga tggcaattag tgcacagcca tcataatata atctgtcacc atcacaacct   1980
ctttgatttg catacaagta aacaccacca caacgtttag tggcatttaa aattaggtct   2040
aacctttat ttaacttacg cagttcatga tgagaaccag atgagtttgt catgatttcc    2100
acaccatcta aagacatggc gatgtggggg gattgaggtg taaacaattc ttcacaagtt   2160
tctgtaccaa tgcatgtatc caatgaattt atcacagcgt ccccaaatgg cacaagtctc   2220
tggccggtaa ctttctgaat ctcaggtgga aggataaagt cctccaccac gccaggtttc   2280
atccaaggtg tgaaaaatct catttcccta tagttaccat cattagctaa ccaaatctta   2340
ggtcttatga acaatatctc accatccaag gataacaaac gacaattata acgaacattc   2400
ttgtgtagaa cgggcatacc aatgtcaagt attaatccat gggtttcttt attcttaatg   2460
atttgagcat acatttccca tgaatgaagg caaacgtcat tttctaaaaa atgatctaaa   2520
catccgtagc cagttatttc cagttctggg ccgacacgta acctggcacc cctctctttg   2580
gcaatcttaa tggactgtag gatacggtct ctattacctt caaaatctag ggcccattga   2640
ttcaagttgc atgtagctaa agtgataaga tgtgccatgg ttttggttta ataagaagag   2700
aaaagagttc ttttgttatg gctgaagtaa tagagaaatg agctcgagtc ctctccaaat   2760
gaaatgaact tccttatata gaggaagggt cttgcgaagg atagtgggat tgtgcgtcat   2820
cccttacgtc agtggagata tcacatcaat ccacttgctt tgaagacgtg gttggaacgt   2880
cttctttttc cacgatgctc ctcgtgggtg ggggtccatc tttgggacca ctgtcggcag   2940
aggcatcttg aacgatagcc tttcctttat cgcaatgatg gcatttgtag gtgccacctt   3000
ccttttctac tgtccttttg atgaagtgac agatagctgg gcaatggaat ccgaggaggt   3060
ttcccgatat taccctttgt tgaaaagtct caatagccct ttggtcttct gagactgtat   3120
ctttgatatt cttggagtag acgagagtgt cgtgctccac catgttgacg aagattttct   3180
tcttgtcatt gagtcgtaaa agactctgta tgaactgttc gccagtcttc acggcgagtt   3240
ctgttagatc ctcgatctga atttttgact ccatgtatgg tgcatatggc gcgccatatg   3300
cccgggccct gtacagcggc cgcgttaacg cgtatactct agagcgatcg cccgggccgg   3360
ccatttaaat gaattcgagc tcggtaccca aacgcggccg caagctataa cttcgtatag   3420
catacattat acgaagttat tcgactctag aggatcccaa ttcccatgca tggagtcaaa   3480
gattcaaata gaggacactt ctcgaactcg gccgtcgaac tcggccgtcg agtacatggt   3540
cgataagaaa aggcaatttg tagatgttaa ttcccatctt gaaagaaata tagtttaaat   3600
atttattgat aaaataacaa gtcaggtatt atagtccaag caaaaacata aatttattga   3660
tgcaagttta aattcagaaa tatttcaata actgattata tcagctggta cattgccgta   3720
gatgaaagac tgagtgcgat attatgtgta atacataaat tgatgatata gctagcttag   3780
ctcatcgggg gatcctagac gcgtgagatc agatctcggt gacgggcagg accggacggg   3840
gcggtaccgg caggctgaag tccagctgcc agaaacccac gtcatgccag ttcccgtgct   3900
tgaagccggc cgcccgcagc atgccgcggg gggcatatcc gagcgcctcg tgcatgcgca   3960
cgctcgggtc gttgggcagc ccgatgacag cgaccacgct cttgaagccc tgtgcctcca   4020
gggacttcag caggtgggtg tagagcgtgg agcccagtcc cgtccgctgg tggcgggggg   4080
agacgtacac ggtcgactcg gccgtccagt cgtaggcgtt gcgtgccttc caggggcccg   4140
cgtaggcgat gccggcgacc tcgccgtcca cctcggcgac gagccaggga tagcgctccc   4200
gcagacggac gaggtcgtcc gtccactcct gcggttcctg cggctcggta cggaagttga   4260
```

```
ccgtgcttgt ctcgatgtag tggttgacga tggtgcagac cgccggcatg tccgcctcgg   4320
tggcacggcg gatgtcggcc gggcgtcgtt ctgggtccat tgttcttctt tactctttgt   4380
gtgactgagg tttggtctag tgctttggtc atctatatat aatgataaca acaatgagaa   4440
caagctttgg agtgatcgga gggtctagga tacatgagat tcaagtggac taggatctac   4500
accgttggat tttgagtgtg gatatgtgtg aggttaattt tacttggtaa cggccacaaa   4560
ggcctaagga gaggtgttga gacccttatc ggcttgaacc gctggaataa tgccacgtgg   4620
aagataattc catgaatctt atcgttatct atgagtgaaa ttgtgtgatg gtggagtggt   4680
gcttgctcat tttacttgcc tggtggactt ggccctttcc ttatggggaa tttatatttt   4740
acttactata gagctttcat accttttttt taccttggat ttagttaata tataatggta   4800
tgattcatga ataaaaatgg gaaatttttg aatttgtact gctaaatgca taagattagg   4860
tgaaactgtg gaatatatat ttttttcatt taaaagcaaa atttgccttt tactagaatt   4920
ataaatatag aaaaatatat aacattcaaa taaaaatgaa aataagaact ttcaaaaaac   4980
agaactatgt ttaatgtgta aagattagtc gcacatcaag tcatctgtta caatatgtta   5040
caacaagtca taagcccaac aaagttagca cgtctaaata aactaaagag tccacgaaaa   5100
tattacaaat cataagccca acaaagttat tgatcaaaaa aaaaaaacgc ccaacaaagc   5160
taaacaaagt ccaaaaaaaa cttctcaagt ctccatcttc ctttatgaac attgaaaact   5220
atacacaaaa caagtcagat aaatctcttt ctgggcctgt cttcccaacc tcctacatca   5280
cttccctatc ggattgaatg ttttacttgt accttttccg ttgcaatgat attgatagta   5340
tgtttgtgaa aactaatagg gttaacaatc gaagtcatgg aatatggatt tggtccaaga   5400
ttttccgaga gctttctagt agaaagccca tcaccagaaa tttactagta aaataaatca   5460
ccaattaggt ttcttattat gtgccaaatt caatataatt atagaggata tttcaaatga   5520
aaacgtatga atgttattag taaatggtca ggtaagacat taaaaaaatc ctacgtcaga   5580
tattcaactt taaaaattcg atcagtgtgg aattgtacaa aaatttggga tctactatat   5640
atatataatg ctttacaaca cttggatttt tttttggagg ctggaatttt taatctacat   5700
atttgttttg gccatgcacc aactcattgt ttagtgtaat actttgattt tgtcaaatat   5760
atgtgttcgt gtatatttgt ataagaattt ctttgaccat atacacacac acatatatat   5820
atatatatat atattatata tcatgcactt ttaattgaaa aaataatata tatatatata   5880
gtgcattttt tctaacaacc atatatgttg cgattgatct gcaaaaatac tgctagagta   5940
atgaaaaata taatctattg ctgaaattat ctcagatgtt aagattttct taaagtaaat   6000
tctttcaaat tttagctaaa agtcttgtaa taactaaaga ataatacaca atctcgacca   6060
cggaaaaaaa acacataata aatttgaatt tcgaccgcgg tacccggaat tgggttataa   6120
ttacctcagg tcgaggaatt aattcggtac gtacctaata acttcgtata gcatacatta   6180
tacgaagtta tatggatctc gaggcattac ggcattacgg cactcgcgag ggtcccaatt   6240
cgagcatgga gccatttaca attgaatata tcctgccgcc gctgccgctt tgcacccggt   6300
ggagcttgca tgttggtttc tacgcagaac tgagccggtt aggcagataa tttccattga   6360
gaactgagcc atgtgcacct tccccccaac acggtgagcg acggggcaac ggagtgatcc   6420
acatgggact tttaaacatc atccgtcgga tggcgttgcg agagaagcag tcgatccgtg   6480
agatcagccg acgcaccggg caggcgcgca acacgatcgc aaagtatttg aacgcaggta   6540
caatcgagcc gacgttcacg gtaccggaac gaccaagcaa gctagcttag taaagccctc   6600
gctagatttt aatgcggatg ttgcgattac ttcgccaact attgcgataa caagaaaaag   6660
```

```
ccagcctttc atgatatatc tcccaatttg tgtagggctt attatgcacg cttaaaaata   6720
ataaaagcag acttgacctg atagtttggc tgtgagcaat tatgtgctta gtgcatctaa   6780
cgcttgagtt aagccgcgcc gcgaagcggc gtcggcttga acgaattgtt agacattatt   6840
tgccgactac cttggtgatc tcgcctttca cgtagtggac aaattcttcc aactgatctg   6900
cgcgcgaggc caagcgatct tcttcttgtc caagataagc ctgtctagct tcaagtatga   6960
cgggctgata ctgggccggc aggcgctcca ttgcccagtc ggcagcgaca tccttcggcg   7020
cgattttgcc ggttactgcg ctgtaccaaa tgcgggacaa cgtaagcact acatttcgct   7080
catcgccagc ccagtcgggc ggcgagttcc atagcgttaa ggtttcattt agcgcctcaa   7140
atagatcctg ttcaggaacc ggatcaaaga gttcctccgc cgctggacct accaaggcaa   7200
cgctatgttc tcttgctttt gtcagcaaga tagccagatc aatgtcgatc gtggctggct   7260
cgaagatacc tgcaagaatg tcattgcgct gccattctcc aaattgcagt tcgcgcttag   7320
ctggataacg ccacggaatg atgtcgtcgt gcacaacaat ggtgacttct acagcgcgga   7380
gaatctcgct ctctccaggg gaagccgaag tttccaaaag gtcgttgatc aaagctcgcc   7440
gcgttgtttc atcaagcctt acggtcaccg taaccagcaa atcaatatca ctgtgtggct   7500
tcaggccgcc atccactgcg gagccgtaca aatgtacggc cagcaacgtc ggttcgagat   7560
ggcgctcgat gacgccaact acctctgata gttgagtcga tacttcggcg atcaccgctt   7620
ccctcatgat gtttaacttt gttttagggc gactgccctg ctgcgtaaca tcgttgctgc   7680
tccataacat caaacatcga cccacggcgt aacgcgcttg ctgcttggat gcccgaggca   7740
tagactgtac cccaaaaaaa cagtcataac aagccatgaa aaccgccact gcgccgttac   7800
caccgctgcg ttcggtcaag gttctggacc agttgcgtga gcgcatacgc tacttgcatt   7860
acagcttacg aaccgaacag gcttatgtcc actgggttcg tgccttcatc cgtttccacg   7920
gtgtgcgtca cccggcaacc ttgggcagca gcgaagtcga ggcatttctg tcctggctgg   7980
cgaacgagcg caaggtttcg gtctccacgc atcgtcaggc attggcggcc ttgctgttct   8040
tctacggcaa gtgctgtgca cggatctgcc ctggcttcag gagatcggaa gacctcggcc   8100
gtccgggcgc ttgccggtgg tgctgacccc ggatgaagtc tctagagctc tagagggttc   8160
gcatcctcgg ttttctggaa ggcgagcatc gtttgttcgc ccagcttctg tatggaacgg   8220
gcatgcggat cagtgagggt ttgcaactgc gggtcaagga tctggatttc gatcacggca   8280
cgatcatcgt gcgggagggc aagggctcca aggatcgggc cttgatgtta cccgagagct   8340
tggcacccag cctgcgcgag cagggatcga tccaacccct ccgctgctat agtgcagtcg   8400
gcttctgacg ttcagtgcag ccgtcttctg aaaacgacat gtcgcacaag tcctaagtta   8460
cgcgacaggc tgccgccctg ccctttttcct ggcgttttct tgtcgcgtgt tttagtcgca   8520
taaagtagaa tacttgcgac tagaaccgga gacattacgc catgaacaag agcgccgccg   8580
ctggcctgct gggctatgcc cgcgtcagca ccgacgacca ggacttgacc aaccaacggg   8640
ccgaactgca cgcggccggc tgcaccaagc tgttttccga gaagatcacc ggcaccaggc   8700
gcgaccgccc ggagctggcc aggatgcttg accacctacg ccctggcgac gttgtgacag   8760
tgaccaggct agaccgcctg gcccgcagca cccgcgacct actggacatt gccgagcgca   8820
tccaggaggc cggcgcgggc ctgcgtagcc tggcagagcc gtgggccgac accaccacgc   8880
cggccggccg catggtgttg accgtgttcg ccggcattgc cgagttcgag cgttccctaa   8940
tcatcgaccg cacccggagc gggcgcgagg ccgccaaggc ccgaggcgtg aagtttggcc   9000
```

```
cccgccctac cctcaccccg gcacagatcg cgcacgcccg cgagctgatc gaccaggaag   9060
gccgcaccgt gaaagaggcg gctgcactgc ttggcgtgca tcgctcgacc ctgtaccgcg   9120
cacttgagcg cagcgaggaa gtgacgccca ccgaggccag gcggcgcggt gccttccgtg   9180
aggacgcatt gaccgaggcc gacgccctgg cggccgccga gaatgaacgc caagaggaac   9240
aagcatgaaa ccgcaccagg acggccagga cgaaccgttt ttcattaccg aagagatcga   9300
ggcggagatg atcgcggccg ggtacgtgtt cgagccgccc gcgcacgtct caaccgtgcg   9360
gctgcatgaa atcctggccg gtttgtctga tgccaagctg gcggcctggc cggccagctt   9420
ggccgctgaa gaaaccgagc gccgccgtct aaaaaggtga tgtgtatttg agtaaaacag   9480
cttgcgtcat gcggtcgctg cgtatatgat gcgatgagta aataaacaaa tacgcaaggg   9540
gaacgcatga aggttatcgc tgtacttaac cagaaaggcg ggtcaggcaa gacgaccatc   9600
gcaacccatc tagcccgcgc cctgcaactc gccggggccg atgttctgtt agtcgattcc   9660
gatccccagg gcagtgcccg cgattgggcg gccgtgcggg aagatcaacc gctaaccgtt   9720
gtcggcatcg accgcccgac gattgaccgc gacgtgaagg ccatcggccg gcgcgacttc   9780
gtagtgatcg acggagcgcc ccaggcggcg gacttggctg tgtccgcgat caaggcagcc   9840
gacttcgtgc tgattccggt gcagccaagc ccttacgaca tatgggccac cgccgacctg   9900
gtggagctgg ttaagcagcg cattgaggtc acggatggaa ggctacaagc ggcctttgtc   9960
gtgtcgcggg cgatcaaagg cacgcgcatc ggcggtgagg ttgccgaggc gctggccggg  10020
tacgagctgc ccattcttga gtcccgtatc acgcagcgcg tgagctaccc aggcactgcc  10080
gccgccggca caaccgttct tgaatcagaa cccgagggcg acgctgcccg cgaggtccag  10140
gcgctggccg ctgaaattaa atcaaaactc atttgagtta atgaggtaaa gagaaaatga  10200
gcaaaagcac aaacacgcta agtgccggcc gtccgagcgc acgcagcagc aaggctgcaa  10260
cgttggccag cctggcagac acgccagcca tgaagcgggt caactttcag ttgccggcgg  10320
aggatcacac caagctgaag atgtacgcgg tacgccaagg caagaccatt accgagctgc  10380
tatctgaata catcgcgcag ctaccagagt aaatgagcaa atgaataaat gagtagatga  10440
attttagcgg ctaaaggagg cggcatggaa aatcaagaac aaccaggcac cgacgccgtg  10500
gaatgcccca tgtgtggagg aacgggcggt tggccaggcg taagcggctg ggttgtctgc  10560
cggccctgca atggcactgg aacccccaag cccgaggaat cggcgtgacg gtcgcaaacc  10620
atccggcccg gtacaaatcg gcgcggcgct gggtgatgac ctggtggaga agttgaaggc  10680
cgcgcaggcc gcccagcggc aacgcatcga ggcagaagca cgccccggtg aatcgtggca  10740
agcggccgct gatcgaatcc gcaaagaatc ccggcaaccg ccggcagccg gtgcgccgtc  10800
gattaggaag ccgcccaagg gcgacgagca accagatttt ttcgttccga tgctctatga  10860
cgtgggcacc cgcgatagtc gcagcatcat ggacgtggcc gttttccgtc tgtcgaagcg  10920
tgaccgacga gctggcgagg tgatccgcta cgagcttcca gacgggcacg tagaggtttc  10980
cgcagggccg gccggcatgg ccagtgtgtg ggattacgac ctggtactga tggcggtttc  11040
ccatctaacc gaatccatga accgataccg ggaagggaag ggagacaagc ccggccgcgt  11100
gttccgtcca cacgttgcgg acgtactcaa gttctgccgg cgagccgatg gcggaaagca  11160
gaaagacgac ctggtagaaa cctgcattcg gttaaacacc acgcacgttg ccatgcagcg  11220
tacgaagaag gccaagaacg gccgcctggt gacggtatcc gagggtgaag ccttgattag  11280
ccgctacaag atcgtaaaga gcgaaaccgg gcggccggag tacatcgaga tcgagctagc  11340
tgattggatg taccgcgaga tcacagaagg caagaacccg gacgtgctga cggttcaccc  11400
```

```
cgattacttt ttgatcgatc ccggcatcgg ccgttttctc taccgcctgg cacgccgcgc  11460
cgcaggcaag gcagaagcca gatggttgtt caagacgatc tacgaacgca gtggcagcgc  11520
cggagagttc aagaagttct gtttcaccgt gcgcaagctg atcgggtcaa atgacctgcc  11580
ggagtacgat ttgaaggagg aggcggggca ggctggcccg atcctagtca tgcgctaccg  11640
caacctgatc gagggcgaag catccgccgg ttcctaatgt acggagcaga tgctagggca  11700
aattgcccta gcaggggaaa aaggtcgaaa aggtctcttt cctgtggata gcacgtacat  11760
tgggaaccca aagccgtaca ttgggaaccg gaacccgtac attgggaacc caaagccgta  11820
cattgggaac cggtcacaca tgtaagtgac tgatataaaa gagaaaaaag gcgatttttc  11880
cgcctaaaac tctttaaaac ttattaaaac tcttaaaacc cgcctggcct gtgcataact  11940
gtctggccag cgcacagccg aagagctgca aaaagcgcct acccttcggt cgctgcgctc  12000
cctacgcccc gccgcttcgc gtcggcctat cgcggccgct ggccgctcaa aaatggctgg  12060
cctacggcca ggcaatctac cagggcgcgg acaagccgcg ccgtcgccac tcgaccgccg  12120
gcgcccacat caaggcaccc tgcctcgcgc gtttcggtga tgacggtgaa aacctctgac  12180
acatgcagct cccggagacg gtcacagctt gtctgtaagc ggatgccggg agcagacaag  12240
cccgtcaggg cgcgtcagcg ggtgttggcg ggtgtcgggg cgcagccatg acccagtcac  12300
gtagcgatag cggagtgtat actggcttaa ctatgcggca tcagagcaga ttgtactgag  12360
agtgcaccat atgcggtgtg aaataccgca cagatgcgta aggagaaaat accgcatcag  12420
gcgctcttcc gcttcctcgc tcactgactc gctgcgctcg gtcgttcggc tgcggcgagc  12480
ggtatcagct cactcaaagg cggtaatacg gttatccaca gaatcagggg ataacgcagg  12540
aaagaacatg tgagcaaaag gccagcaaaa ggccaggaac cgtaaaaagg ccgcgttgct  12600
ggcgtttttc cataggctcc gcccccctga cgagcatcac aaaaatcgac gctcaagtca  12660
gaggtggcga aacccgacag gactataaag ataccaggcg tttccccctg gaagctccct  12720
cgtgcgctct cctgttccga ccctgccgct taccggatac ctgtccgcct ttctcccttc  12780
gggaagcgtg gcgctttctc atagctcacg ctgtaggtat ctcagttcgg tgtaggtcgt  12840
tcgctccaag ctgggctgtg tgcacgaacc ccccgttcag cccgaccgct gcgccttatc  12900
cggtaactat cgtcttgagt ccaacccggt aagacacgac ttatcgccac tggcagcagc  12960
cactggtaac aggattagca gagcgaggta tgtaggcggt gctacagagt tcttgaagtg  13020
gtggcctaac tacggctaca ctagaaggac agtatttggt atctgcgctc tgctgaagcc  13080
agttaccttc ggaaaaagag ttggtagctc ttgatccggc aaacaaacca ccgctggtag  13140
cggtggtttt tttgtttgca agcagcagat tacgcgcaga aaaaaaggat ctcaagaaga  13200
tccggaaaac gcaagcgcaa agagaaagca ggtagcttgc agtgggctta catggcgata  13260
gctagactgg gcggttttat ggacagcaag cgaaccggaa ttgcc                 13305
```

<210> SEQ ID NO 34
<211> LENGTH: 13326
<212> TYPE: DNA
<213> ORGANISM: Artificial
<220> FEATURE:
<223> OTHER INFORMATION: pTVE503

<400> SEQUENCE: 34

```
agattcgaag ctcggtcccg tgggtgttct gtcgtctcgt tgtacaacga aatccattcc     60
cattccgcgc tcaagatggc ttcccctcgg cagttcatca gggctaaatc aatctagccg    120
```

```
acttgtccgg tgaaatgggc tgcactccaa cagaaacaat caaacaaaca tacacagcga    180
cttattcaca cgcgacaaat tacaacggta tatatcctgc cagtactcgg ccgtcgaccg    240
cggtaccccg gaattaagct tgcatgcctg caggcaattg gccgctgtac catgcatgat    300
ctggatttta gtactggatt ttggttttag gaattagaaa ttttattgat agaagtattt    360
tacaaataca aatacatact aagggtttct tatatgctca acacatgagc gaaaccctat    420
aggaacccta attcccttat ctgggaacta ctcacacatt attatggaga aaatagagag    480
agatagattt gtagagagag actggtgatt tcagcgtgtc caagcttgct agcctaatca    540
atagacataa tgtcaagcgt tgagccttta tgtgcttcac actgctcgac aacttcatca    600
atttttcttg aagcccatgg aaatcttggg ttgattaaga aaggacgtaa gtcaaatctg    660
ttgtcttctg gtgaatactg ttcagcatga taactaggag ttaaaacagt ttgcttgtgt    720
ctgttgatgg catagaagaa gaaaaatctt ttcacctttt cagatatttg acgaggtgtt    780
aactttgggg accattgatg aagaagtttt aagaacatag aataaggacc acatttttca    840
acctttctta ggtaaccaaa cacgcccaat tcttcatacg tcatccccat atctatctca    900
tccgattgaa cgtaatcttt agtcataggt tctaattctg cagttggtgt agcgtttaaa    960
aagtcattca agattggcat gttatattgt tttgatgcgt aggcaatgaa tcttttcaag   1020
tcagtttttg aaataccccc aatagggttg atatctgcgg aggagcagtc atattttgtt   1080
agatacccac gtaagcactc atcaacattt gcgctaccaa gtactaacaa tccacccgag   1140
tttgggatac cacgaaccca cggcaacagt tgcgcaaaaa gataagaaag aaccattctt   1200
agacgcgcct ggatgttttg taaagccaag ttctcgattt gagatccccc aaatattttg   1260
tatattggtt ttttgccagt ggctacttcg aataaggaca ccacactgga taccaatgag   1320
tccatcttta aatccacgtg gtaagatcca attgcattgg aaaggtcctt tgctctgttt   1380
cttgtctcct tggatgaatt ttccgtaccc atgaaacagg agtgaaatat ttttgaggct   1440
agatcctgtg gactgtctgg aatccaatca tcgccgctac gtgttatctt acgaacgtct   1500
ttgataactt gctcatttcc attttgagca gcgtcggtca ctaaacggca catagagtgg   1560
acaatcattg cagttgcaca agagtcaatg cccccagata agggaaggaa aaaccctgtt   1620
ccgttacaac gtcttaaata atcccacatc cagcaagcag gtcccagtgc aatttcttcc   1680
tcaggagagt gatagaaagg ctcgcggact tttgttggac acactgtagg atcaaatctg   1740
gaggtcatta aagccaattc tacaggaata tcaatacgct tgaactttat ttctgccaag   1800
gaggcttgta ggccacgaga catgacagct gcacgataac tcctcacctc ttctaggtcc   1860
acagtagcag taactacttc cacatcatct agcgaaaatt gtgaaccttg ggctacaatt   1920
gtaccattga tggcaattag tgcacagcca tcataatata atctgtcacc atcacaacct   1980
ctttgatttg catacaagta aacaccacca caacgtttag tggcatttaa aattaggtct   2040
aaccttttat ttaacttacg cagttcatga tgagaaccag atgagtttgt catgatttcc   2100
acaccatcta aagacatggc gatgtggggg gattgaggtg taaacaattc ttcacaagtt   2160
tctgtaccaa tgcatgtatc caatgaattt atcacagcgt ccccaaatgg cacaagtctc   2220
tggccggtaa ctttctgaat ctcaggtgga aggataaagt cctccaccac gccaggtttc   2280
atccaaggtg tgaaaaatct catttcccta tagttaccat cattagctaa ccaaatctta   2340
ggtcttatga acaatatctc accatccaag gataacaaac gacaattata acgaacattc   2400
ttgtgtagaa cgggcatacc aatgtcaagt attaatccat gggtttcttt attcttaatg   2460
atttgagcat acatttccca tgaatgaagg caaacgtcat tttctaaaaa atgatctaaa   2520
```

```
catccgtagc cagttatttc cagttctggg ccgacacgta acctggcacc cctctctttg   2580
gcaatcttaa tggactgtag gatacggtct ctattacctt caaaatctag ggcccattga   2640
ttcaagttgc atgtagctaa agtgataaga accttgcgct tcttcttggg atgtgccatg   2700
gttttggttt aataagaaga gaaaagagtt cttttgttat ggctgaagta atagagaaat   2760
gagctcgagt cctctccaaa tgaaatgaac ttccttatat agaggaaggg tcttgcgaag   2820
gatagtggga ttgtgcgtca tcccttacgt cagtggagat atcacatcaa tccacttgct   2880
ttgaagacgt ggttggaacg tcttcttttt ccacgatgct cctcgtgggt gggggtccat   2940
ctttgggacc actgtcggca gaggcatctt gaacgatagc ctttccttta tcgcaatgat   3000
ggcatttgta ggtgccacct tccttttcta ctgtcctttt gatgaagtga cagatagctg   3060
ggcaatggaa tccgaggagg tttcccgata ttaccctttg ttgaaaagtc tcaatagccc   3120
tttggtcttc tgagactgta tctttgatat tcttggagta gacgagagtg tcgtgctcca   3180
ccatgttgac gaagattttc ttcttgtcat tgagtcgtaa aagactctgt atgaactgtt   3240
cgccagtctt cacggcgagt tctgttagat cctcgatctg aatttttgac tccatgtatg   3300
gtgcatatgg cgcgccatat gcccgggccc tgtacagcgg ccgcgttaac gcgtatactc   3360
tagagcgatc gcccgggccg gccatttaaa tgaattcgag ctcggtaccc aaacgcggcc   3420
gcaagctata acttcgtata gcatacatta tacgaagtta ttcgactcta gaggatccca   3480
attcccatgc atggagtcaa agattcaaat agaggacact tctcgaactc ggccgtcgaa   3540
ctcggccgtc gagtacatgg tcgataagaa aaggcaattt gtagatgtta attcccatct   3600
tgaaagaaat atagtttaaa tatttattga taaaataaca agtcaggtat tatagtccaa   3660
gcaaaaacat aaatttattg atgcaagttt aaattcagaa atatttcaat aactgattat   3720
atcagctggt acattgccgt agatgaaaga ctgagtgcga tattatgtgt aatacataaa   3780
ttgatgatat agctagctta gctcatcggg ggatcctaga cgcgtgagat cagatctcgg   3840
tgacgggcag gaccggacgg ggcggtaccg gcaggctgaa gtccagctgc cagaaaccca   3900
cgtcatgcca gttcccgtgc ttgaagccgg ccgcccgcag catgccgcgg ggggcatatc   3960
cgagcgcctc gtgcatgcgc acgctcgggt cgttgggcag cccgatgaca gcgaccacgc   4020
tcttgaagcc ctgtgcctcc agggacttca gcaggtgggt gtagagcgtg gagcccagtc   4080
ccgtccgctg gtggcggggg gagacgtaca cggtcgactc ggccgtccag tcgtaggcgt   4140
tgcgtgcctt ccaggggccc gcgtaggcga tgccggcgac ctcgccgtcc acctcggcga   4200
cgagccaggg atagcgctcc cgcagacgga cgaggtcgtc cgtccactcc tgcggttcct   4260
gcggctcggt acggaagttg accgtgcttg tctcgatgta gtggttgacg atggtgcaga   4320
ccgccggcat gtccgcctcg gtggcacggc ggatgtcggc cgggcgtcgt tctgggtcca   4380
ttgttcttct ttactctttg tgtgactgag gtttggtcta gtgctttggt catctatata   4440
taatgataac aacaatgaga acaagctttg gagtgatcgg agggtctagg atacatgaga   4500
ttcaagtgga ctaggatcta caccgttgga ttttgagtgt ggatatgtgt gaggttaatt   4560
ttacttggta acggccacaa aggcctaagg agaggtgttg agacccttat cggcttgaac   4620
cgctggaata atgccacgtg gaagataatt ccatgaatct tatcgttatc tatgagtgaa   4680
attgtgtgat ggtggagtgg tgcttgctca ttttacttgc ctggtggact tggccctttc   4740
cttatgggga atttatattt tacttactat agagctttca tacctttttt ttaccttgga   4800
tttagttaat atataatggt atgattcatg aataaaaatg ggaaattttt gaatttgtac   4860
```

-continued

```
tgctaaatgc ataagattag gtgaaactgt ggaatatata ttttttttcat ttaaaagcaa   4920
aatttgcctt ttactagaat tataaatata gaaaaatata taacattcaa ataaaaatga   4980
aaataagaac tttcaaaaaa cagaactatg tttaatgtgt aaagattagt cgcacatcaa   5040
gtcatctgtt acaatatgtt acaacaagtc ataagcccaa caaagttagc acgtctaaat   5100
aaactaaaga gtccacgaaa atattacaaa tcataagccc aacaaagtta ttgatcaaaa   5160
aaaaaaaacg cccaacaaag ctaaacaaag tccaaaaaaa acttctcaag tctccatctt   5220
cctttatgaa cattgaaaac tatacacaaa acaagtcaga taaatctctt tctgggcctg   5280
tcttcccaac ctcctacatc acttccctat cggattgaat gttttacttg tacctttttcc   5340
gttgcaatga tattgatagt atgtttgtga aaactaatag ggttaacaat cgaagtcatg   5400
gaatatggat ttggtccaag attttccgag agctttctag tagaaagccc atcaccagaa   5460
atttactagt aaaataaatc accaattagg tttcttatta tgtgccaaat tcaatataat   5520
tatagaggat atttcaaatg aaaacgtatg aatgttatta gtaaatggtc aggtaagaca   5580
ttaaaaaaat cctacgtcag atattcaact ttaaaaattc gatcagtgtg gaattgtaca   5640
aaaatttggg atctactata tatatataat gctttacaac acttggattt ttttttggag   5700
gctggaattt ttaatctaca tatttgtttt ggccatgcac caactcattg tttagtgtaa   5760
tactttgatt ttgtcaaata tatgtgttcg tgtatatttg tataagaatt tctttgacca   5820
tatacacaca cacatatata tatatatata tatattatat atcatgcact tttaattgaa   5880
aaaataatat atatatatat agtgcatttt ttctaacaac catatatgtt gcgattgatc   5940
tgcaaaaata ctgctagagt aatgaaaaat ataatctatt gctgaaatta tctcagatgt   6000
taagattttc ttaaagtaaa ttctttcaaa ttttagctaa aagtcttgta ataactaaag   6060
aataatacac aatctcgacc acggaaaaaa aacacataat aaatttgaat ttcgaccgcg   6120
gtacccggaa ttgggttata attacctcag gtcgaggaat taattcggta cgtacctaat   6180
aacttcgtat agcatacatt atacgaagtt atatggatct cgaggcatta cggcattacg   6240
gcactcgcga gggtcccaat tcgagcatgg agccatttac aattgaatat atcctgccgc   6300
cgctgccgct ttgcacccgg tggagcttgc atgttggttt ctacgcagaa ctgagccggt   6360
taggcagata atttccattg agaactgagc catgtgcacc ttcccccccaa cacggtgagc   6420
gacggggcaa cggagtgatc cacatgggac ttttaaacat catccgtcgg atggcgttgc   6480
gagagaagca gtcgatccgt gagatcagcc gacgcaccgg gcaggcgcgc aacacgatcg   6540
caaagtattt gaacgcaggt acaatcgagc cgacgttcac ggtaccggaa cgaccaagca   6600
agctagctta gtaaagccct cgctagattt taatgcggat gttgcgatta cttcgccaac   6660
tattgcgata acaagaaaaa gccagccttt catgatatat ctcccaattt gtgtagggct   6720
tattatgcac gcttaaaaat aataaaagca gacttgacct gatagtttgg ctgtgagcaa   6780
ttatgtgctt agtgcatcta acgcttgagt taagccgcgc cgcgaagcgg cgtcggcttg   6840
aacgaattgt tagacattat ttgccgacta ccttggtgat ctcgcctttc acgtagtgga   6900
caaattcttc caactgatct gcgcgcgagg ccaagcgatc ttcttcttgt ccaagataag   6960
cctgtctagc ttcaagtatg acgggctgat actgggccgg caggcgctcc attgcccagt   7020
cggcagcgac atccttcggc gcgattttgc cggttactgc gctgtaccaa atgcgggaca   7080
acgtaagcac tacatttcgc tcatcgccag cccagtcggg cggcgagttc catagcgtta   7140
aggtttcatt tagcgcctca aatagatcct gttcaggaac cggatcaaag agttcctccg   7200
ccgctggacc taccaaggca acgctatgtt ctcttgcttt tgtcagcaag atagccagat   7260
```

-continued caatgtcgat cgtggctggc tcgaagatac ctgcaagaat gtcattgcgc tgccattctc 7320
caaattgcag ttcgcgctta gctggataac gccacggaat gatgtcgtcg tgcacaacaa 7380
tggtgacttc tacagcgcgg agaatctcgc tctctccagg ggaagccgaa gtttccaaaa 7440
ggtcgttgat caaagctcgc cgcgttgttt catcaagcct tacggtcacc gtaaccagca 7500
aatcaatatc actgtgtggc ttcaggccgc catccactgc ggagccgtac aaatgtacgg 7560
ccagcaacgt cggttcgaga tggcgctcga tgacgccaac tacctctgat agttgagtcg 7620
atacttcggc gatcaccgct tccctcatga tgtttaactt tgttttaggg cgactgccct 7680
gctgcgtaac atcgttgctg ctccataaca tcaaacatcg acccacggcg taacgcgctt 7740
gctgcttgga tgcccgaggc atagactgta ccccaaaaaa acagtcataa caagccatga 7800
aaaccgccac tgcgccgtta ccaccgctgc gttcggtcaa ggttctggac cagttgcgtg 7860
agcgcatacg ctacttgcat tacagcttac gaaccgaaca ggcttatgtc cactgggttc 7920
gtgccttcat ccgtttccac ggtgtgcgtc acccggcaac cttgggcagc agcgaagtcg 7980
aggcatttct gtcctggctg gcgaacgagc gcaaggtttc ggtctccacg catcgtcagg 8040
cattggcggc cttgctgttc ttctacggca agtgctgtgc acggatctgc cctggcttca 8100
ggagatcgga agacctcggc cgtccgggcg cttgccggtg gtgctgaccc cggatgaagt 8160
ctctagagct ctagagggtt cgcatcctcg gttttctgga aggcgagcat cgtttgttcg 8220
cccagcttct gtatggaacg ggcatgcgga tcagtgaggg tttgcaactg cgggtcaagg 8280
atctggattt cgatcacggc acgatcatcg tgcgggaggg caagggctcc aaggatcggg 8340
ccttgatgtt acccgagagc ttggcaccca gcctgcgcga gcagggatcg atccaacccc 8400
tccgctgcta tagtgcagtc ggcttctgac gttcagtgca gccgtcttct gaaaacgaca 8460
tgtcgcacaa gtcctaagtt acgcgacagg ctgccgccct gcccttttcc tggcgttttc 8520
ttgtcgcgtg ttttagtcgc ataaagtaga atacttgcga ctagaaccgg agacattacg 8580
ccatgaacaa gagcgccgcc gctggcctgc tgggctatgc ccgcgtcagc accgacgacc 8640
aggacttgac caaccaacgg gccgaactgc acgcggccgg ctgcaccaag ctgttttccg 8700
agaagatcac cggcaccagg cgcgaccgcc cggagctggc caggatgctt gaccacctac 8760
gccctggcga cgttgtgaca gtgaccaggc tagaccgcct ggcccgcagc acccgcgacc 8820
tactggacat tgccgagcgc atccaggagg ccggcgcggg cctgcgtagc ctggcagagc 8880
cgtgggccga caccaccacg ccggccggcc gcatggtgtt gaccgtgttc gccggcattg 8940
ccgagttcga gcgttcccta atcatcgacc gcacccggag cgggcgcgag gccgccaagg 9000
cccgaggcgt gaagtttggc ccccgcccta ccctcacccc ggcacagatc gcgcacgccc 9060
gcgagctgat cgaccaggaa ggccgcaccg tgaaagaggc ggctgcactg cttggcgtgc 9120
atcgctcgac cctgtaccgc gcacttgagc gcagcgagga agtgacgccc accgaggcca 9180
ggcggcgcgg tgccttccgt gaggacgcat tgaccgaggc cgacgccctg gcggccgccg 9240
agaatgaacg ccaagaggaa caagcatgaa accgcaccag gacggccagg acgaaccgtt 9300
tttcattacc gaagagatcg aggcggagat gatcgcggcc gggtacgtgt tcgagccgcc 9360
cgcgcacgtc tcaaccgtgc ggctgcatga aatcctggcc ggtttgtctg atgccaagct 9420
ggcggcctgg ccggccagct tggccgctga agaaaccgag cgccgccgtc taaaaaggtg 9480
atgtgtattt gagtaaaaca gcttgcgtca tgcggtcgct gcgtatatga tgcgatgagt 9540
aaataaacaa atacgcaagg ggaacgcatg aaggttatcg ctgtacttaa ccagaaaggc 9600

```
gggtcaggca agacgaccat cgcaacccat ctagcccgcg ccctgcaact cgccggggcc   9660
gatgttctgt tagtcgattc cgatccccag ggcagtgccc gcgattgggc ggccgtgcgg   9720
gaagatcaac cgctaaccgt tgtcggcatc gaccgcccga cgattgaccg cgacgtgaag   9780
gccatcggcc ggcgcgactt cgtagtgatc gacggagcgc cccaggcggc ggacttggct   9840
gtgtccgcga tcaaggcagc cgacttcgtg ctgattccgg tgcagccaag cccttacgac   9900
atatgggcca ccgccgacct ggtggagctg gttaagcagc gcattgaggt cacggatgga   9960
aggctacaag cggcctttgt cgtgtcgcgg gcgatcaaag gcacgcgcat cggcggtgag  10020
gttgccgagg cgctggccgg gtacgagctg cccattcttg agtcccgtat cacgcagcgc  10080
gtgagctacc caggcactgc cgccgccggc acaaccgttc ttgaatcaga acccgagggc  10140
gacgctgccc gcgaggtcca ggcgctggcc gctgaaatta aatcaaaact catttgagtt  10200
aatgaggtaa agagaaaatg agcaaaagca caaacacgct aagtgccggc cgtccgagcg  10260
cacgcagcag caaggctgca acgttggcca gcctggcaga cacgccagcc atgaagcggg  10320
tcaactttca gttgccggcg gaggatcaca ccaagctgaa gatgtacgcg gtacgccaag  10380
gcaagaccat taccgagctg ctatctgaat acatcgcgca gctaccagag taaatgagca  10440
aatgaataaa tgagtagatg aattttagcg gctaaaggag gcggcatgga aaatcaagaa  10500
caaccaggca ccgacgccgt ggaatgcccc atgtgtggag gaacgggcgg ttggccaggc  10560
gtaagcggct gggttgtctg ccggccctgc aatggcactg gaacccccaa gcccgaggaa  10620
tcggcgtgac ggtcgcaaac catccggccc ggtacaaatc ggcgcggcgc tgggtgatga  10680
cctggtggag aagttgaagg ccgcgcaggc cgcccagcgg caacgcatcg aggcagaagc  10740
acgccccggt gaatcgtggc aagcggccgc tgatcgaatc cgcaaagaat cccggcaacc  10800
gccggcagcc ggtgcgccgt cgattaggaa gccgcccaag ggcgacgagc aaccagattt  10860
tttcgttccg atgctctatg acgtgggcac ccgcgatagt cgcagcatca tggacgtggc  10920
cgttttccgt ctgtcgaagc gtgaccgacg agctggcgag gtgatccgct acgagcttcc  10980
agacgggcac gtagaggttt ccgcagggcc ggccggcatg gccagtgtgt gggattacga  11040
cctggtactg atggcggttt cccatctaac cgaatccatg aaccgatacc gggaagggaa  11100
gggagacaag cccggccgcg tgttccgtcc acacgttgcg gacgtactca agttctgccg  11160
gcgagccgat ggcggaaagc agaaagacga cctggtagaa acctgcattc ggttaaacac  11220
cacgcacgtt gccatgcagc gtacgaagaa ggccaagaac ggccgcctgg tgacggtatc  11280
cgagggtgaa gccttgatta gccgctacaa gatcgtaaag agcgaaaccg ggcggccgga  11340
gtacatcgag atcgagctag ctgattggat gtaccgcgag atcacagaag gcaagaaccc  11400
ggacgtgctg acggttcacc ccgattactt tttgatcgat cccggcatcg gccgttttct  11460
ctaccgcctg gcacgccgcg ccgcaggcaa ggcagaagcc agatggttgt tcaagacgat  11520
ctacgaacgc agtggcagcg ccggagagtt caagaagttc tgtttcaccg tgcgcaagct  11580
gatcgggtca aatgacctgc cggagtacga tttgaaggag gaggcggggc aggctggccc  11640
gatcctagtc atgcgctacc gcaacctgat cgagggcgaa gcatccgccg gttcctaatg  11700
tacggagcag atgctagggc aaattgccct agcaggggaa aaaggtcgaa aaggtctctt  11760
tcctgtggat agcacgtaca ttgggaaccc aaagccgtac attgggaacc ggaacccgta  11820
cattgggaac ccaaagccgt acattgggaa ccggtcacac atgtaagtga ctgatataaa  11880
agagaaaaaa ggcgattttt ccgcctaaaa ctctttaaaa cttattaaaa ctcttaaaac  11940
ccgcctggcc tgtgcataac tgtctggcca gcgcacagcc gaagagctgc aaaaagcgcc  12000
```

-continued

```
taccettcgg tcgctgcgct ccctacgccc cgccgcttcg cgtcggccta tcgcggccgc  12060

tggccgctca aaaatggctg gcctacggcc aggcaatcta ccagggcgcg gacaagccgc  12120

gccgtcgcca ctcgaccgcc ggcgcccaca tcaaggcacc ctgcctcgcg cgtttcggtg  12180

atgacggtga aaacctctga cacatgcagc tcccggagac ggtcacagct tgtctgtaag  12240

cggatgccgg gagcagacaa gcccgtcagg gcgcgtcagc gggtgttggc gggtgtcggg  12300

gcgcagccat gacccagtca cgtagcgata gcggagtgta tactggctta actatgcggc  12360

atcagagcag attgtactga gagtgcacca tatgcggtgt gaaataccgc acagatgcgt  12420

aaggagaaaa taccgcatca ggcgctcttc cgcttcctcg ctcactgact cgctgcgctc  12480

ggtcgttcgg ctgcggcgag cggtatcagc tcactcaaag gcggtaatac ggttatccac  12540

agaatcaggg gataacgcag gaaagaacat gtgagcaaaa ggccagcaaa aggccaggaa  12600

ccgtaaaaag gccgcgttgc tggcgttttt ccataggctc cgcccccctg acgagcatca  12660

caaaaatcga cgctcaagtc agaggtggcg aaacccgaca ggactataaa gataccaggc  12720

gtttccccct ggaagctccc tcgtgcgctc tcctgttccg accctgccgc ttaccggata  12780

cctgtccgcc tttctccctt cgggaagcgt ggcgctttct catagctcac gctgtaggta  12840

tctcagttcg gtgtaggtcg ttcgctccaa gctgggctgt gtgcacgaac cccccgttca  12900

gcccgaccgc tgcgccttat ccggtaacta tcgtcttgag tccaacccgg taagacacga  12960

cttatcgcca ctggcagcag ccactggtaa caggattagc agagcgaggt atgtaggcgg  13020

tgctacagag ttcttgaagt ggtggcctaa ctacggctac actagaagga cagtatttgg  13080

tatctgcgct ctgctgaagc cagttacctt cggaaaaaga gttggtagct cttgatccgg  13140

caaacaaacc accgctggta gcggtggttt ttttgtttgc aagcagcaga ttacgcgcag  13200

aaaaaaagga tctcaagaag atccggaaaa cgcaagcgca aagagaaagc aggtagcttg  13260

cagtgggctt acatggcgat agctagactg ggcggtttta tggacagcaa gcgaaccgga  13320

attgcc                                                             13326
```